United States Patent
Haji Reza et al.

(10) Patent No.: US 11,122,978 B1
(45) Date of Patent: Sep. 21, 2021

(54) PARS IMAGING METHODS

(71) Applicant: ILLUMISONICS INC., Edmonton (CA)

(72) Inventors: Parsin Haji Reza, Edmonton (CA); Zohreh Hosseinaee, Edmonton (CA); Kevan Bell, Edmonton (CA); Saad Abbasi, Edmonton (CA); Ben Eccelstone, Edmonton (CA)

(73) Assignee: illumiSonics Inc.

( * ) Notice: Subject to any disclaimer, the term of this patent is extended or adjusted under 35 U.S.C. 154(b) by 0 days.

(21) Appl. No.: 17/010,500

(22) Filed: Sep. 2, 2020

Related U.S. Application Data

(60) Provisional application No. 63/040,866, filed on Jun. 18, 2020.

(51) Int. Cl.
| | |
|---|---|
| *A61B 5/00* | (2006.01) |
| *G01B 9/02* | (2006.01) |
| *G01N 29/24* | (2006.01) |
| *G01N 21/17* | (2006.01) |

(52) U.S. Cl.
CPC .......... *A61B 5/0066* (2013.01); *A61B 5/0035* (2013.01); *G01B 9/02091* (2013.01); *G01N 21/1702* (2013.01); *G01N 29/2418* (2013.01); *A61B 5/0095* (2013.01); *G01N 2291/02475* (2013.01)

(58) Field of Classification Search
CPC ... A61B 5/0066; A61B 5/0035; A61B 5/0095; G01N 21/1702; G01N 29/2418; G01N 29/24; G01N 2291/02475; G01B 9/02091
See application file for complete search history.

(56) References Cited

U.S. PATENT DOCUMENTS

| | | | |
|---|---|---|---|
| 5,070,733 | A | 12/1991 | Nagata et al. |
| 5,479,259 | A | 12/1995 | Nakata et al. |
| 5,615,675 | A | 4/1997 | O'Donnell et al. |
| 5,991,479 | A | 11/1999 | Kleinerman |
| 6,016,202 | A | 1/2000 | Fuchs et al. |
| 6,078,397 | A | 6/2000 | Monchalin et al. |

(Continued)

FOREIGN PATENT DOCUMENTS

| | | |
|---|---|---|
| CN | 101526483 A | 9/2009 |
| CN | 103048271 A | 4/2013 |

(Continued)

OTHER PUBLICATIONS

Beard, Paul. "Biomedical Photoacoustic Imaging." Interface Focus 1.4 (2011): 602-631. PMC. Web. Dec. 12, 2017.

(Continued)

*Primary Examiner* — Amelie R Davis
*Assistant Examiner* — John Denny Li
(74) *Attorney, Agent, or Firm* — Bookoff McAndrews, PLLC

(57) ABSTRACT

A dual-modality photoacoustic remote sensing combined with optical coherence tomography (PARS-OCT) system for visualizing details in a sample, the system comprising one or more light sources configured to generate (1) one or more excitation beams configured to generate signals in the sample at one or more first locations below a surface of the sample; (2) one or more interrogation beams incident on the sample at one or more second locations; (3) a sample beam; and (4) a reference beam.

20 Claims, 43 Drawing Sheets

(56) References Cited

U.S. PATENT DOCUMENTS

| | | | |
|---|---|---|---|
| 6,256,100 | B1 | 7/2001 | Banet et al. |
| 6,973,830 | B2 | 12/2005 | Pepper et al. |
| 6,992,829 | B1 | 1/2006 | Jennings et al. |
| 7,068,842 | B2 | 6/2006 | Liang et al. |
| 8,004,689 | B2 | 8/2011 | Monchalin et al. |
| 8,180,134 | B2 | 5/2012 | Wang |
| 8,454,512 | B2 | 6/2013 | Wang et al. |
| 8,692,155 | B2 | 4/2014 | Bischoff et al. |
| 9,153,931 | B2 | 10/2015 | Ichihara et al. |
| 9,999,354 | B2 | 6/2018 | Rousseau et al. |
| 2006/0184042 | A1 | 8/2006 | Wang et al. |
| 2006/0262316 | A1 | 11/2006 | Baney |
| 2008/0123083 | A1 | 5/2008 | Wang et al. |
| 2008/0194929 | A1 | 8/2008 | Pesach et al. |
| 2009/0170149 | A1 | 7/2009 | Viator et al. |
| 2010/0268042 | A1 | 10/2010 | Wang et al. |
| 2012/0200845 | A1 | 8/2012 | Rousseau et al. |
| 2012/0320368 | A1 | 12/2012 | Jiao et al. |
| 2013/0281889 | A1* | 10/2013 | Gertner ............... A61B 5/4839 601/2 |
| 2014/0009808 | A1 | 1/2014 | Wang et al. |
| 2014/0118749 | A1 | 5/2014 | Nakajima et al. |
| 2014/0185055 | A1* | 7/2014 | Wang ................ A61B 5/7203 356/479 |
| 2014/0247456 | A1 | 9/2014 | Horstmann et al. |
| 2015/0031990 | A1* | 1/2015 | Boctor ................ A61B 8/5261 600/424 |
| 2015/0077819 | A1 | 3/2015 | Schnell et al. |
| 2015/0148655 | A1 | 5/2015 | Haupt et al. |
| 2015/0150465 | A1 | 6/2015 | Irisawa et al. |
| 2015/0153269 | A1 | 6/2015 | Nakatsuka |
| 2015/0164337 | A1 | 6/2015 | Kim et al. |
| 2015/0185187 | A1 | 7/2015 | Wang et al. |
| 2015/0221081 | A1 | 8/2015 | Chang et al. |
| 2015/0265156 | A1 | 9/2015 | Tanaka |
| 2016/0113507 | A1* | 4/2016 | Reza ................... G01N 21/1702 356/477 |
| 2016/0156148 | A1* | 6/2016 | Thomsen ........... G01B 9/02091 356/72 |
| 2016/0249812 | A1* | 9/2016 | Wang ................. A61B 5/14542 600/407 |
| 2017/0215738 | A1 | 8/2017 | Haji Reza et al. |
| 2018/0275046 | A1* | 9/2018 | Haji Reza ............ A61B 5/0095 |
| 2019/0104944 | A1* | 4/2019 | Reza .................. G01N 21/1702 |
| 2020/0237228 | A1* | 7/2020 | Bhawalkar .......... A61B 5/0064 |

FOREIGN PATENT DOCUMENTS

| | | |
|---|---|---|
| CN | 109363639 A | 2/2019 |
| DE | 10 2010 012 809 A1 | 9/2011 |
| WO | 2009055705 A2 | 4/2009 |
| WO | 2009055705 A3 | 6/2009 |
| WO | 2013023210 A1 | 2/2013 |
| WO | 2013166044 A1 | 11/2013 |
| WO | 2014027316 A2 | 2/2014 |
| WO | 2014036405 A2 | 3/2014 |
| WO | 2014062529 A1 | 4/2014 |
| WO | 2014160116 A1 | 10/2014 |
| WO | 2014168930 A1 | 10/2014 |

OTHER PUBLICATIONS

International Search Report and Written Opinion dated Dec. 19, 2018 in International Application No. PCT/IB2018/057585 (25 pages).

Kevan L. Bell et al., "Coherence-gated photoacoustic remote sensing microscopy", Optics Express, vol. 26, No. 18, Sep. 3, 2018, 16 pp.

Zhihua Ding et al., "Real-time phase-resolved optical coherence tomography and optical Doppler tomography", Optics Express, vol. 10, No. 5, Mar. 11, 2002, 10 pages.

Cedric Blatter et al., "Intrasweep phase-sensitive optical coherence tomography for noncontact optical photoacoustic imaging", Optics Letters, vol. 37, No. 21, Nov. 1, 2012, 4 pp.

* cited by examiner

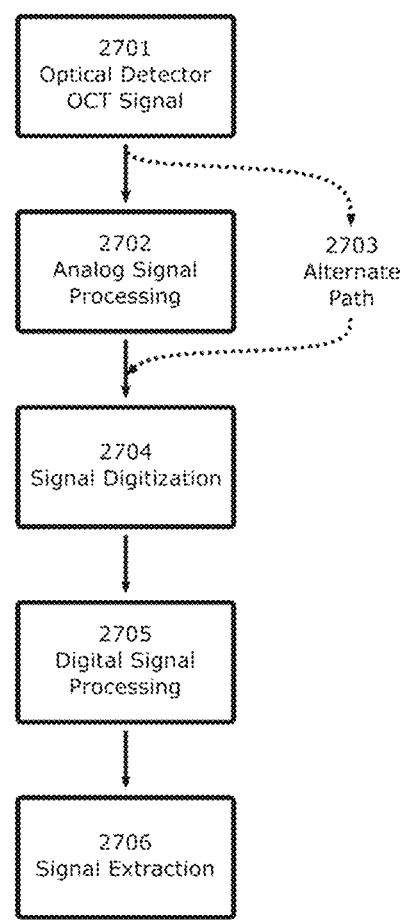

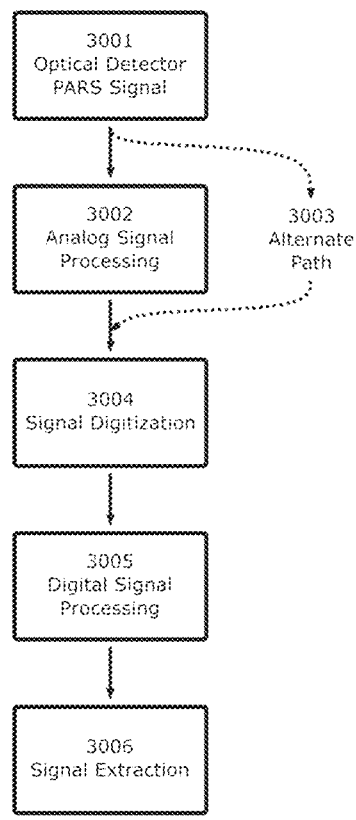

PARS IMAGING METHODS

CROSS-REFERENCE TO RELATED APPLICATIONS

This application claims priority to U.S. Provisional Patent Application No. 63/040,866, filed on Jun. 18, 2020, the entirety of which is incorporated herein by reference.

FIELD

This relates to the field of optical imaging and, in particular, to a laser-based method and system for non-contact imaging of samples such as industrial materials or biological tissue in vivo, ex vivo, or in vitro.

BACKGROUND

Photoacoustic imaging techniques represent a powerful family of modalities which are capable of visualizing intrinsic endogenous optical absorption contrast within optically scattering media. In common photoacoustic architectures, nanosecond or picosecond laser pulses are directed into a sample causing the generation of thermo-elastic induced acoustic waves, which are then observed and reconstructed to form images of the optical absorption distribution. By carefully selecting the wavelength of the excitation source, absorption contrast of specific biomolecules can be targeted. For example, 532 nm is a widely used wavelength for targeting hemoglobin. These systems have proven to be efficacious in recovering clinically relevant biological structure from within biological tissues. Some examples include vascular structures from macro vessels to micro vessels, cellular structure, and lipid rich plaques along with functional imaging including visualization of blood oxygen saturation.

Photoacoustic imaging can be split into two main categories: Photoacoustic tomography (PAT) uses reconstruction-based image formation, while photoacoustic microscopy (PAM) uses focused-based image formation. In PAT, an unfocused optical beam excites the region of interest, and an array of transducers measures the generated ultrasound waves in multiple positions. PAM employs raster-scanning of optical and acoustic foci and forms images directly from recorded depth-resolved signals. PAM can be further classified into optical-resolution PAM (OR-PAM), where the optical focusing is much tighter than acoustic focusing, and acoustic-resolution PAM (AR-PAM), where the acoustic focusing is tighter. In all three embodiments, the acoustic signal is typically collected through an acoustically coupled transducer or other acoustic- or acousto-optic resonator. In all cases the photoacoustic signals (which are commonly associated with generation of pressure and temperature within the sample) can be recorded to form an image representing the optical absorption in the sample at the excitation wavelength in which the amplitude of the various recorded peaks implies the local optical absorption.

However, since conventional photoacoustic techniques require physical coupling to the sample, they are inappropriate for a wide variety of clinical applications such as ophthalmic imaging, intraoperative imaging, monitoring of wound healing, and many endoscopic procedures.

A recently reported photoacoustic technology known as photoacoustic remote sensing (PARS) microscopy (US 2016/0113507, and US 2017/0215738) has solved many of these sensitivity issues through a novel detection mechanism. Rather than detecting acoustic pressures at an outer surface once they have propagated away from their source, PARS enables direct detection of excited photoacoustic regions. This is accomplished by monitoring changes in material optical properties that coincide with the photoacoustic excitation. These changes then encode various salient material properties such as the optical absorption, physical target dimensions, and constituent chromophores to name a few.

SUMMARY

According to an aspect, there is provided a thermally enhanced photoacoustic remote sensing (TE-PARS) system for imaging a subsurface structure in the sample which provides absorption contrast within the sample.

The TE-PARS system comprises an excitation beam or collection of beams configured to generate PARS signals in the sample at an excitation location or collection of locations; a signal enhancement beam or collection of beams configured to modify the observation or generation of temperature and pressure signals, incident on the sample at the excitation or interrogation location or collection of locations; an interrogation beam or collection of beams incident on the sample at an interrogation location or collection of locations; an optical system or collection of systems that focuses or directs the excitation beam or collection of beams at a first focal point or collection of focal points, the signal enhancement beams at a second focal point or collection of focal points and the interrogation beams at a third focal point or collection of focal points, the first, second and third focal points or collection of focal points being below the surface of the sample; a portion of the interrogation and or signal enhancement beam or collection of beams returning from the sample that is indicative of the generated PARS signals; an optical detector or collection of optical detectors to detect the returning portion or portions of the interrogation and or signal enhancement beams; and a processing unit for interpreting collected results.

Embodiments of TE-PARS may comprise several collections of PARS signal enhancement pathways, which may also function as detection pathways.

According to another aspect, there is provided a temperature sensing photoacoustic remote sensing (TS-PARS) system for detecting the temperature of a subsurface structure within a sample.

The TS-PARS system comprises an excitation beam or collection of beams configured to generate PARS signals in the sample at an excitation location or collection of locations; an interrogation beam or collection of beams incident on the sample at an interrogation location or collection of locations; an optical system or collection of systems that focuses or directs the excitation beam or collection of beams at a first focal point or collection of focal points and the interrogation beams at a second focal point or collection of focal points, the first and second focal points or collection of focal points being below the surface of the sample; a portion of the interrogation beam or collection of beams returning from the sample that is indicative of the generated PARS signals; an optical detector or collection of optical detectors to detect the returning portion or portions of the interrogation and or signal enhancement beams; and a temperature processing unit for interpreting collected results.

According to another aspect, there is provided a super-resolution photoacoustic remote sensing (SR-PARS) system for imaging a subsurface structure in the sample with resolution greater than that defined by the optical diffraction limit by leveraging optical absorption contrast within the sample.

The SR-PARS system comprises an excitation beam or collection of beams configured to generate PARS signals in the sample at an excitation location or collection of locations; an interrogation beam or collection of beams incident on the sample at an interrogation location or collection of locations; an optical system or collection of systems that focuses or directs the excitation beam or collection of beams at a first focal point or collection of focal points and the interrogation beams at a second focal point or collection of focal points, the first and second focal points or collection of focal points being below the surface of the sample; a portion of the interrogation beam or collection of beams returning from the sample that is indicative of the generated PARS signals; an optical detector or collection of optical detectors to detect the returning portion or portions of the interrogation beams; and a super-resolution processing unit for interpreting collected results.

According to another aspect, there is provided a spectrally-enhanced photoacoustic remote sensing (SE-PARS) system for imaging a subsurface structure in the sample which leverages chromatic effects and spatial filtering methods to encode spatial information within the sample.

The SE-PARS system comprises an excitation beam or collection of beams configured to generate PARS signals in the sample at an excitation location or collection of locations; an interrogation beam or collection of beams incident on the sample at an interrogation location or collection of locations; an optical system or collection of optical systems which disburses the interrogation beams based on their wavelength or spatial positioning; an optical system or collection of systems that focuses or directs the excitation beam or collection of beams at a first focal point or collection of focal points and the interrogation beams at a second focal point or collection of focal points, the first and second focal points or collection of focal points being below the surface of the sample; a portion of the interrogation beam or collection of beams returning from the sample that is indicative of the generated PARS signals; an optical system or collection of optical systems which recombines the interrogation beams based on their wavelength or spatial positioning; an optical detector or collection of optical detectors to detect the returning portion or portions of the interrogation beams; and a processing unit for interpreting collected results.

According to another aspect, there is provided a smart-detection photoacoustic remote sensing (SD-PARS) system for imaging a subsurface structure in the sample which leverages wavelength-specific absorption to encode or suppress spatial information within the sample.

The SD-PARS system comprises an excitation beam or collection of beams configured to generate PARS signals in the sample at an excitation location or collection of locations; an interrogation beam or collection of beams incident on the sample at an interrogation location or collection of locations; an optical system or collection of systems that focuses or directs the excitation beam or collection of beams at a first focal point or collection of focal points and the interrogation beam at a second focal point or collection of focal points, the first and second focal points or collection of focal points being below the surface of the sample; a portion of the interrogation beam or collection of beams returning from the sample that is indicative of the generated PARS signals; and a processing unit for interpreting collected results. What sets SD-PARS apart from standard PARS devices is that the detection wavelength maybe purposefully selected such that it suppresses generated photoacoustic or PARS signals from a particular region. For example, if a desired target is positioned next to a large blood vessel which might otherwise overwhelm the signal from the desired target, the detection wavelength may be selected as to suppress signal from the blood vessel by populating absorption energy levels prior to detection.

Embodiments of TE-PARS, TS-PARS, SE-PARS, SD-PARS and SR-PARS may comprise several collections of PARS, TE-PARS, SE-PARS, SD-PARS, TS-PARS, and SR-PARS detection pathways.

PARS pathways may comprise of but are not limited to conventional PARS as described in U.S. Pat. No. 10,117,583, non-interferometric PARS as described in U.S. Pat. No. 10,327,646, camera-based PARS as described in U.S. Pat. No. 10,627,338, coherence-gated PARS as described in International Publication No. WO2019/145764, single-source PARS as described in International Patent Application No. PCT/IB2020/051804, filed on Mar. 3, 2020, and the PARS extensions described in International Patent Application No. PCT/IB2019/061131, filed on Dec. 19, 2019, the entireties of each of which is incorporated by reference herein.

According to another aspect, there is provided a dual-modality photoacoustic remote sensing combined with optical coherence tomography (PARS-OCT) system for imaging a subsurface structure in the sample which provides absorption and scattering contrast of the tissue.

The PARS subsystem of the PARS-OCT comprises an excitation beam or collection of beams configured to generate pressure and temperature signals in the sample at an excitation location or collection of locations; an interrogation beam or collection of beams incident on the sample at an interrogation location or collection of locations; an optical system or collection of systems that focuses or directs the excitation beam or collection of beams at a first focal point or collection of focal points and the interrogation beam at a second focal point or collection of focal points, the first and second focal points or collection of focal points being below the surface of the sample; a portion of the interrogation beam or collection of interrogation beams returning from the sample that is indicative of the generated pressure and temperature signals; an optical detector or collection of optical detectors to detect the returning portion or portions of the interrogation, and a processing unit for interpreting collected results.

The OCT subsystem of the PARS-OCT comprises a light source or collection of light sources; an interferometer or collection of interferometers each with a single or multiple of a sample arm and a reference arm where the sample arm directs the sample portion of the beam or collection of beams to a third focal point and the reference arm directs the reference portion of the beam or collection of beams into a path of known length; a portion of the light returning from the sample arm that is indicative of the scattering collected by the sample arm; a portion of the light returning from the reference arm that is indicative of the scattering collected by the reference arm; an optical detector or collection of optical detectors to detect the returning portions from the sample arm or arms and reference arm or arms, and the processing unit for interpreting collected results.

According to another aspect, there is provided an endoscopic photoacoustic remote sensing combined with optical coherence tomography (EPARS-OCT) device which provides absorption and scattering information of the sample.

The PARS subsystem of the EPARS-OCT comprises an excitation beam or collection of beams configured to generate pressure and temperature signals in the sample at an excitation location or collection of locations; an interrogation beam or collection of beams incident on the sample at an interrogation location or collection of locations; a fiber optic cable or collection of cables having an input end and a detection end; an optical system or collection of systems that focuses or directs the excitation beam or collection of beams at a first focal point or collection of focal points and the interrogation beam at a second focal point or collection of focal points, the first and second focal points or collection of focal points being below the surface of the sample; a portion of the interrogation beam or collection of interrogation beams returning from the sample that is indicative of the generated pressure and temperature signals; an optical detector or collection of optical detectors to detect the returning portion or portions of the interrogation, and a processing unit for interpreting collected results.

The OCT subsystem of the EPARS-OCT comprises a light source or collection of light sources; an interferometer or collection of interferometers each with a single or multiple of a sample arm and a reference arm where the sample arm directs the sample portion of the beam or collection of beams to a third focal point through a fiber optic cable or collection of cables having an input end and a detection end and the reference arm directs the reference portion of the beam or collection of beams into a path of known length; a portion of the light returning from the sample arm that is indicative of the scattering collected by the sample arm; a portion of the light returning from the reference arm that is indicative of the scattering collected by the reference arm; an optical detector or collection of optical detectors to detect the returning portions from the sample arm or arms and reference arm or arms, and the processing unit for interpreting collected results.

Embodiments of PARS-OCT may comprise several collections of PARS detection pathways and OCT detection pathways.

Embodiments of EPARS-OCT may comprise several collections of PARS detection pathways and OCT detection pathways.

PARS detection pathways may comprise of but are not limited to conventional PARS as described in [APP1], non-interferometric PARS as described in [APP2], camera-based PARS as described in [APP3], coherence-gated PARS as described in [APP4], single-source PARS as described in [APP5], the PARS extensions described in [APP6], TE-PARS, TS-PARS, SR-PARS, SE-PARS and SD-PARS.

OCT detection pathways may comprise of but are not limited to known implementations of TD-OCT, SS-OCT, SD-OCT, or other OCT embodiments. For example, a TD-OCT system with a broadband light source, scanning reference path delay and a photodetector. For another example, a SS-OCT system with tuning narrow band source, stationary reference path delay and a photodetector. For yet another example, a SD-OCT system with broadband light source, stationary reference path delay and a spectrometer.

Any combinations of the above listed PARS or OCT pathways may be envisioned such as the specified PARS-OCT. However, any such combinations or obvious extensions may also be produced.

Novel PARS signal extraction algorithms may leverage a variety of absorption-induced modulation effects including but not limited to modulation of material reflectivity, scattering, polarization, phase accumulation, nonlinear absorption, nonlinear scattering, etc. These may be used for multiplex acquisitions to unmix constituent chromophores from within a sample by using a variety of excitation and detection beam properties including but not limited to variations in wavelength, pulse width, power, energy, coherence length, repetition rate, exposure times, etc. These properties may take on any value appropriate for the task. Common ranges may include: wavelengths (nanometers to microns), pulse widths (attoseconds to milliseconds), powers (attowatts to watts), pulse energies (attojoules to joules), coherence lengths (nanometers to kilometers), and repetition rates (continuous-wave to gigahertz).

Other novel PARS signal extraction algorithms may leverage time-domain behavior to improve signal fidelity, enhance image contrast and to recover information on the sample shape, size and dimensions, or for performing multiplexed/functional imaging. Processing techniques may include but are not limited to lock-in amplification (both software and hardware-based implementations), machine learning methods, and frequency content-based feature extraction and signal processing methods.

PARS may be used to unmix the composition of targets based on their absorption, temperature, polarization, frequency, phase, nonlinear absorption, fluorescence, nonlinear scattering and scattering content.

It may also be used to unmix the size, shape, feature, and dimensions of targets based on their absorption, temperature, polarization, frequency, phase, nonlinear absorption, nonlinear scattering and scattering content.

The PARS signals may be used for unmixing targets using their absorption contents, scattering contents, fluorescence, polarization contents, frequency contents, phase contents by taking advantage of different wavelengths, different pulse widths, different coherence lengths, repetition rates, lasers exposure time, laser fluence.

PARS signals may be dominated by generated pressure and analyzed based on their, amplitude/intensity, frequency content, content related to polarization changes, fluorescence, second harmonic generation, and phase variations to provide information PARS signals may be dominated by generated temperature and analyzed based on their, amplitude/intensity, fluorescence, frequency content, second harmonic generation, content related to polarization changes, and phase variations to provide information Other aspects will be apparent from the description and claims below.

BRIEF DESCRIPTION OF THE DRAWINGS

In this patent document, the word "comprising" is used in its non-limiting sense to mean that items following the word are included, but items not specifically mentioned are not excluded. A reference to an element by the indefinite article "a" does not require that there be one and only one of the elements.

The scope of the following claims should not be limited by the preferred embodiments set forth in the examples above and in the drawings but should be given the broadest interpretation consistent with the description as a whole.

FIG. 27 Shows an overview of OCT signal data processing pathway.

FIG. 30 Shows an overview of PARS signal data processing pathways.

DETAILED DESCRIPTION

Figure 1:
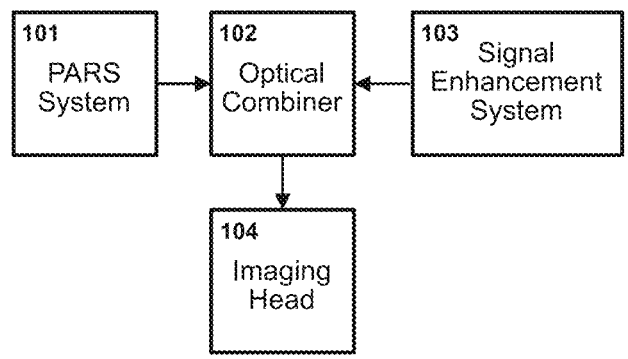
FIG. 1 An overview of the TE-PARS system.

Reference will now be made in detail to examples of the present disclosure, which are illustrated in the accompanying drawings. Wherever possible, the same reference numbers will be used throughout the drawings to refer to the same or like parts. In the discussion that follows, relative terms such as "about," "substantially," "approximately," etc. are used to indicate a possible variation in a stated numeric value.

Since PARS devices utilized two optical beams which may be in a confocal arrangement, spatial resolution of the imaging technique may be defined as excitation-defined (ED) or interrogation-defined (ID) depending on which of the beams provide a tighter focus at the sample. This aspect also may facilitate imaging deeper targets, beyond the limits of conventional contact-based OR-PAM devices. This may be accomplished by leveraging a deeply-penetrating (long transport mean-free-path) detection wavelength such as a short-wave infrared (like 1310 nm or 1700 nm) which may provide spatial resolution to a depth superior to that provided by a given excitation (such as 532 nm) within highly scattering media such as biological tissues. It is worth mentioning, that if more than two beams are used such that a system consists of more than two foci at the sample, then obvious extensions of these components would be expected. For example, if an additional beam which amplifies the signal within its focal region is added, it may also contribute towards defining the expected resolution of the system.

The PARS systems described herein are fundamentally different from the previously described PARS systems. These devices take advantage of novel physical discoveries to substantially improve on the capabilities of previous reports. Included are PARS systems which take advantage of material temperature dependencies to enhance the absorption contrast and sensitivity available to PARS acquisitions. Material saturation effects are leveraged to surpass resolution capabilities provided solely by diffraction-limited optics. Modern spatial-spectral encoding techniques are integrated which may improve acquisition efficiency and imaging rate. As well, we describe novel processing techniques for use in multiplex acquisitions such as separating chromophores using various beam properties (wavelength, pulse width, power, coherence length, repetition rates, exposure times, signal frequency content, and optical saturation, scattering, polarization, and phase effects to name a few), and processing techniques for extracting additional information from time-domain signals.

Possible mechanisms include a pressure-induced refractive-index modulation, thermally-induced refractive index modulation, surface oscillations, and scatterer position modulation due to confined thermal expansion.

Refractive index changes due to temperature and pressure rises may in turn affect the scattering of light. In some cases, the detected PARS signals may be dominated by the generated pressure and or temperature.

Since many of these novel aspects take advantage of fundamentally different physical effects, these additions are highlighted. First, within a highly simplified abstraction, the pressure generated $p_0$ by a sufficiently short optical pulse of fluence $\phi$ may be defined by the following relationship $$p_0 = \Gamma \mu_\alpha \phi$$

where $\mu_\alpha$ represents the optical absorption within the sample and $\Gamma$ is known as the Grüneisen parameter which describes the ratio of material properties. However, coincident with this rise in pressure will be a rise in temperature brought on by exposure to the multitude of beams within the PARS system. This will in turn affect pressure generation by modifying both the Grüneisen parameter $\Gamma$ and the optical absorption $\mu_\alpha$. This then implies that the efficiency of pressure generation may be modified through temperature T. In PARS devices the pressure rise $p_0$ is commonly measured as a change in scattering or reflectivity from the excitation region. This change in optical scattering may result from the elasto-optic effect in which the pressure $p_0$ modulates the local refractive index by an amount $\delta n_{eo}$ following the relationship for a given detection wavelength $\lambda$ as $$\delta n_{eo}(\mu_a, \phi, \lambda, T) = \frac{\epsilon n_s^3 p_0}{2\rho v_s^2}$$

where $\epsilon$ is the elasto-optic coefficient, $n_s$ is the unperturbed refractive index of the sample, $\rho$ is the density, and $v_s$ is the acoustic propagation velocity. Likewise, the rise in temperature T will also generate a modulation in the local refractive index by some amount $\delta n_T(\lambda, T)$. These effects then compound upon each other and will partially defined the measured PARS signal $S_{PARS}$ following $$S_{PARS}(\mu_\alpha, \phi, \lambda, T) \propto \delta n_{eo} + \delta n_T$$

Therefore, the intensity-modulated PARS signals hold dependence on not only optical absorption and incident excitation fluence, but also on detection laser wavelength, fluence and the temperature of the sample. PARS signals may also arise from other effects such as scatterer position modulation and surface oscillations. A similar analog may exist for PARS devices which take advantage of other modulating optical properties such as intensity, polarization, frequency, phase, fluorescence, non-linear scattering, non-linear absorption, etc.

As material properties are dependent on ambient temperature, there is a corresponding temperature dependence in the PARS signal. These temperature dependencies may facilitate temperature sensing with PARS systems.

Temperature dependencies may also facilitate thermally enhanced photoacoustic remote sensing (TE-PARS) techniques. The TE-PARS systems may use a signal enhancement source in addition to the PARS excitation and detection sources. The signal enhancement source may deposit optical energy which modifies the local material properties, and therefore the induced pressure modulations.

At some intensity levels additional saturation effects may also be leveraged. For example, the optical absorption $\mu_\alpha$ will experience saturation at intensity levels $I_0$ approaching a characteristic saturation intensity $I_{sat}$ following $$\mu_a = \frac{\mu_{a0}}{1 + I_0/I_{sat}}$$

where $\mu_{\alpha 0}$ is the optical absorption of the material prior to saturation. This produces a nonlinear spatial distribution of signal for a given linear input of excitation intensity. In much the same way that nonlinear fluorescent effects are leveraged in super resolution fluorescent microscopes, PARS may likewise leverage this nonlinear saturation to surpass the $\lambda/2$ diffraction resolution limit.

The above mechanisms point to significant sources of scattering position or scattering cross-section modulation that could be readily measurable when the probe beam is focused to sense the confined excitation volume. However, these large local signals are not the only potential source of PARS signal. Acoustic signals propagating to the surface of the sample could also result in changes in PARS signal. These acoustic signals can generate surface oscillation as well which result in phase modulation of the PARS signals.

These generated signals may be intentionally controlled or effected by secondary physical effects such as vibration, temperature, stress, surface roughness, mechanical bending among others. For example, temperature may be introduced to the sample which may augment the generated PARS signals as compared to those which would be generated without having introduced this additional temperature. Another example may involve introducing mechanical stress to the sample (such as bending) which may in turn effects the density of the sample and thereby perturbing with the generated PARS signals as compared to those which would have been generated without having introduced this mechanical stress.

Additional contrast agents may be added to the sample to boost the generated PARS signals, this includes but not limited to dyes, proteins, specially designed cells, liquids and optical agents or windows. The target may be altered optically to provide optimized results.

Another aspect which is leveraged by these new disclosures revolves around the scattering, polarization, frequency and phase contents of generated PARS signals. Excitation events occur over short time periods, for example less than 100 ns, in which time, the monitored modulations in detection signal contain a wealth of information. For example, older PARS techniques which simply monitored intensity back reflection, may extract the amplitude of these time-domain signals. However, additional information may be extracted from the time-varying aspects of the signals. For example, some of the scattering, polarization, frequency, and phase content with a PARS signal may be attributed to the size, shape, features, and dimensions of the region which generated that signal. This may encode unique/orthogonal additional information with utility towards improving final image fidelity, classifying sample regions, sizing constituent chromophores and classifying constituent chromophores to name a few. As such techniques may generate independent datasets for the same interrogated region they may be combined or compared with each other. For example, frequency information may describe the microscopic structures within the sample, this may be combined with conventional PARS which uses scattering modulation to highlight regions which are both absorbing and of a specific size.

A final aspect for disclosure in this document revolves around the combination of a PARS device alongside an optical coherence tomography (OCT). OCT is a complementary imaging modality to PARS devices. Whereas PARS techniques provide visualization of optical absorption contrast, OCT imaging devices provide visualization of optical scattering contrast. Each approach captures an independent set of information about the sample. For example, PARS may yield high contrast blood vessel information with high specificity, and OCT may yield high contrast information of the surrounding tissue such as nearby dermal layers.

OCT measurements can be performed using various approaches, either in the time domain optical coherence tomography (TD-OCT) or in frequency domain optical coherence tomography (FD-OCT) as described in [US 2010/0265511 and US2014/0125952].

In TD-OCT a laser is passed through an interferometer where one arm (the reference arm) is incident on a movable mirror and the other arm (the sample arm) is incident on the sample. Scattering information is typically extracted by scanning a reference path length and recording the resulting interferogram pattern on an optical detector such as a photodiode as a function of that length. The envelope of this pattern represents a map of the reflectivity within the sample versus depth, generally called an A-scan, with depth resolution given by the coherence length of the source laser.

FD-OCT is likewise commonly implemented with an interferometer, a sample arm, and a reference arm. It is generally separated into two distinct methods. The first, spectral-domain optical coherence tomography (SD-OCT) or spectrometer-based OCT, uses a continuous-wave broadband light source and achieves spectral discrimination with a dispersive spectrometer in the detector arm. The second, termed swept-source optical coherence tomography (SS-OCT), time-encodes wavenumber reflectivity by rapidly tuning a narrowband source through a broad optical bandwidth. Both techniques may allow for a dramatic improvement in SNR of up to 15.0-20.0 dB over TD-OCT.

In OCT systems, multiple A-scans are typically acquired while the sample beam is scanned laterally across the tissue surface, building up a two-dimensional map of reflectivity versus depth and lateral extent typically called a B-scan. The lateral resolution of the B-scan is approximated by the confocal resolving power of the sample arm optical system, which is usually given by the size of the focused optical spot in the tissue.

There has been a great body of work within the OCT field towards providing quantitative optical absorption measurement. This is of particular interest within the ophthalmic imaging community which requires oxygen saturation measurement about the fundus of the eye. There have been several notable works on this topic, however the current approach is still incapable of direct optical absorption measurement (unlike PARS modalities). Rather, optical absorption must be inferred through the use of a visible probe source which can greatly limit the penetration depth into the sample. It would be highly beneficial to the biomedical imaging community to offer an improved optical absorption modality.

Given these complementary properties between PARS and OCT, there would be a clear benefit towards augmenting PARS with OCT. Here, novel technical details of a dual-modality PARS OCT system are discussed.

FIG. 1 shows a high-level diagram of a TE-PARS system. This consists of a PARS system (101), an optical combiner (102), a signal enhancement system (103) and an imaging head (104). The optical combiner is used to combine the beams from the PARS system (101) and the Signal Enhancement System (103).

Figure 2:
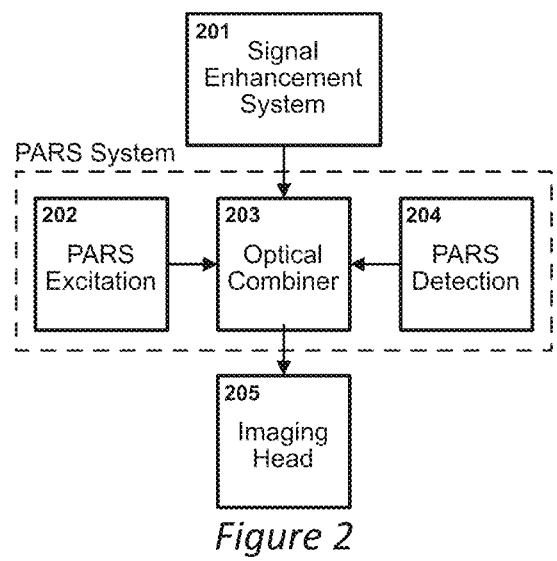
FIG. 2 An overview of the TE-PARS system with PARS Excitation and PARS Detection.

FIG. 2 shows a high-level diagram with the PARS Excitation (202), PARS Detection (204) and Optical Combiner (203) delineated. These are combined with a Signal Enhancement System (201) and Imaging Head (205).

Figure 3:
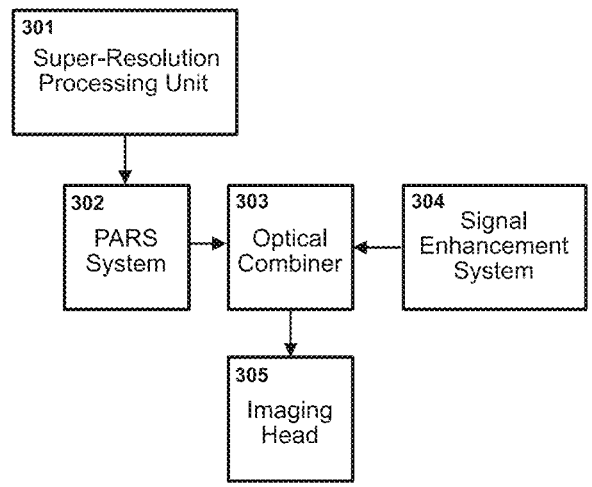
FIG. 3 An overview of a SR-TE-PARS system.

FIG. 3 shows a high-level diagram of a SR-PARS system. This consists of a Super-Resolution Processing Unit (301), a PARS system (302), an optical combiner (303), a signal enhancement system (304) and an imaging head (305).

Figure 4:
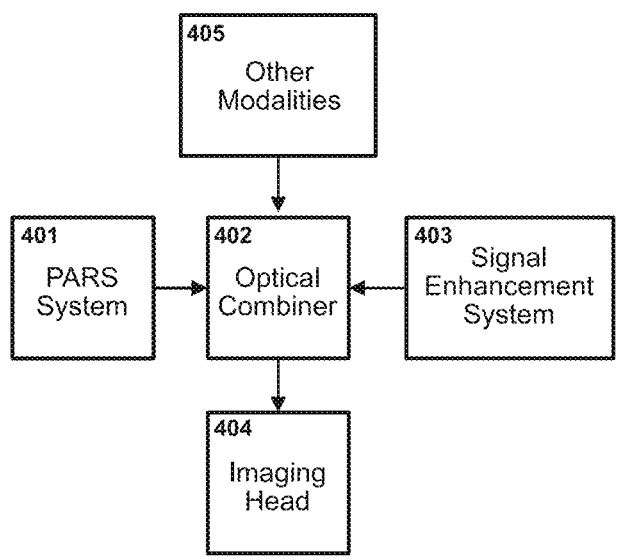
FIG. 4 Shows a possible implementation of TE-PARS being combined with other modalities.

FIG. 4 shows a high-level embodiment of a TE-PARS system combined with other modalities (405). This consists of a PARS system (401), optical combiner (402), signal enhancement system (403), an imaging head (404). These can be combined with a variety of other modalities such as a bright-field microscopy, scanning laser ophthalmoscope, ultrasound imaging, stimulated Raman microscopy, fluorescence microscopy, two-photon and confocal fluorescence microscopy, Coherent-Anti-Raman-Stokes microscopy, Raman microscopy, other PARS, photoacoustic and ultrasound systems, among others.

Figure 5:
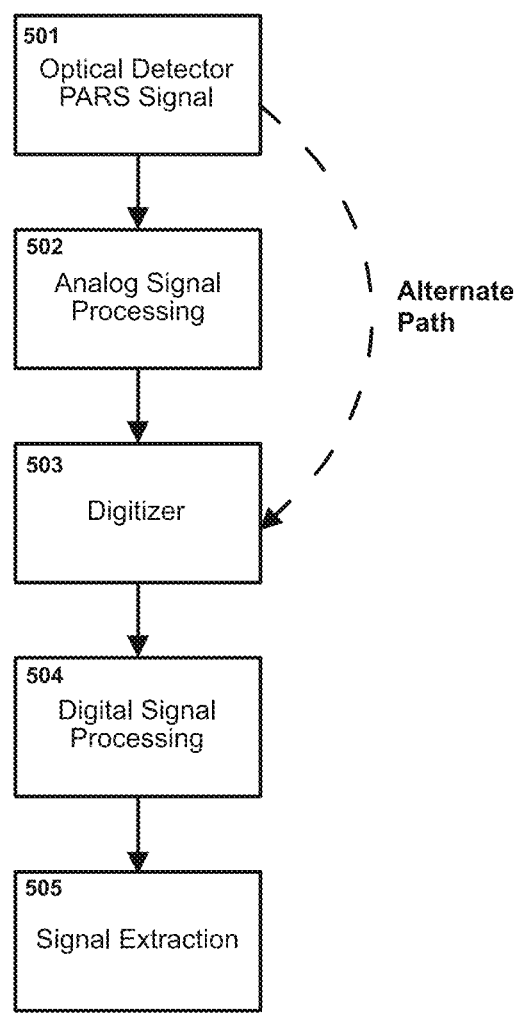
FIG. 5 Shows a signal processing pathway of TE-PARS signals.

FIG. 5 shows the signal processing pathway. This consists of an optical detector (501), a signal processing unit (502), a digitizer (503), a digital signal processing unit (504) and a signal extraction unit (505).

Figure 6:
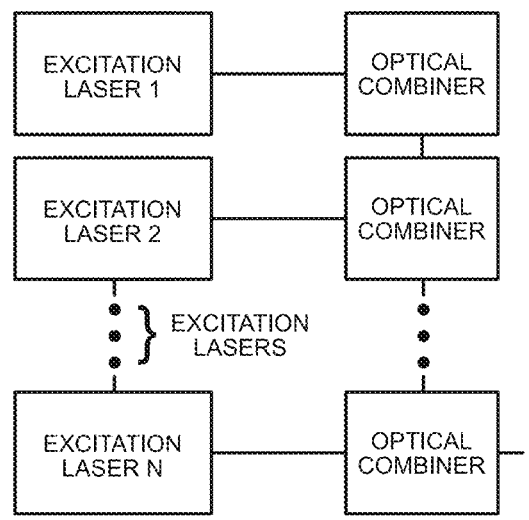
FIG. 6 Shows a implementation of multiple PARS excitation lasers.

FIG. 6 shows an embodiment of multiple excitation lasers combined with optical combiners.

Figure 7:
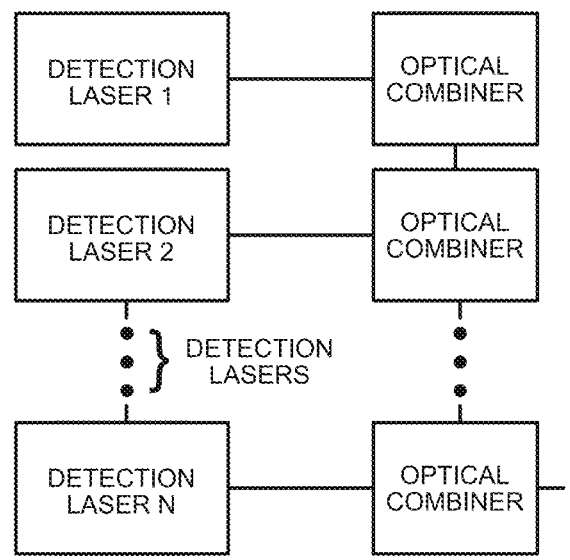
FIG. 7 Shows a implementation of multiple PARS detection lasers.

FIG. 7 shows an embodiment of multiple detection lasers combined with optical combiners.

Figure 8:
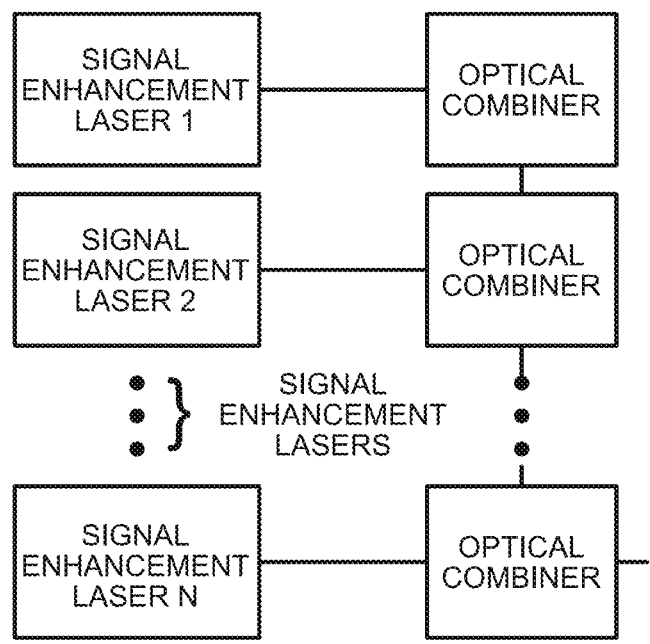
FIG. 8 Shows a implementation of multiple PARS signal enhancement lasers.

FIG. 8 shows an embodiment of multiple signal enhancement lasers combined with optical combiners.

Figure 9:
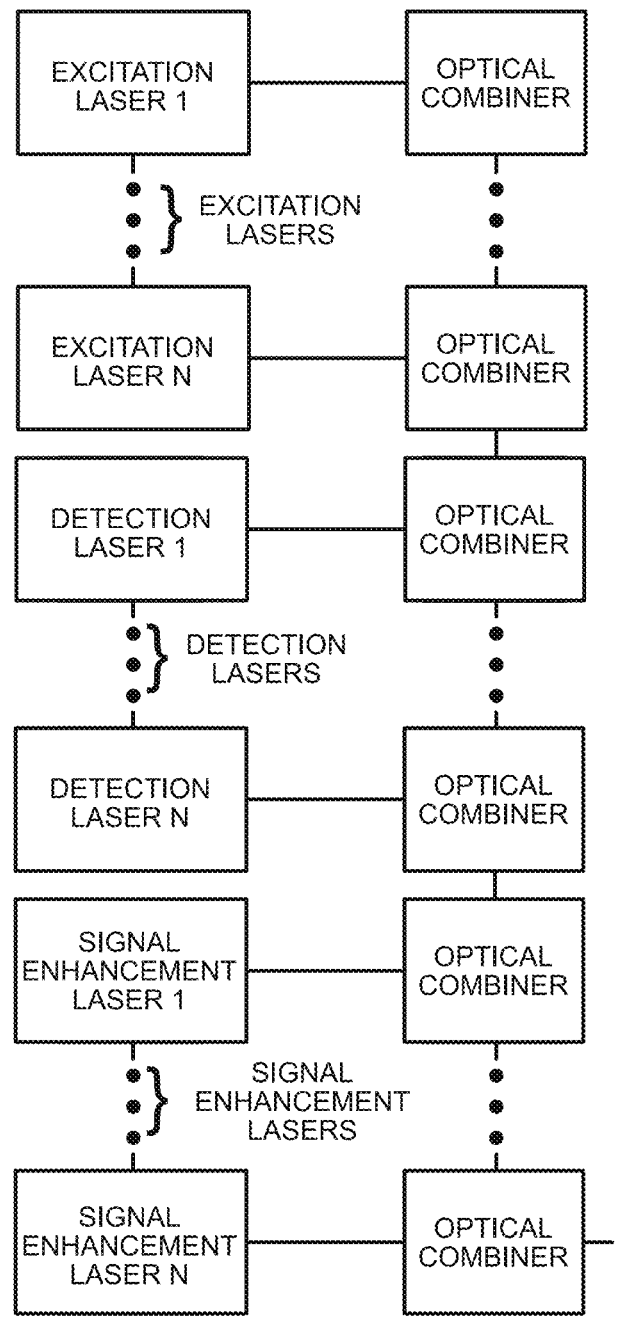
FIG. 9 Shows a implementation of multiple excitation lasers, multiple detection lasers and multiple signal enhancement lasers.

FIG. 9 shows an embodiment of multiple excitation lasers, multiple detection lasers and multiple signal enhancement lasers combined with optical combiners.

Figure 10:
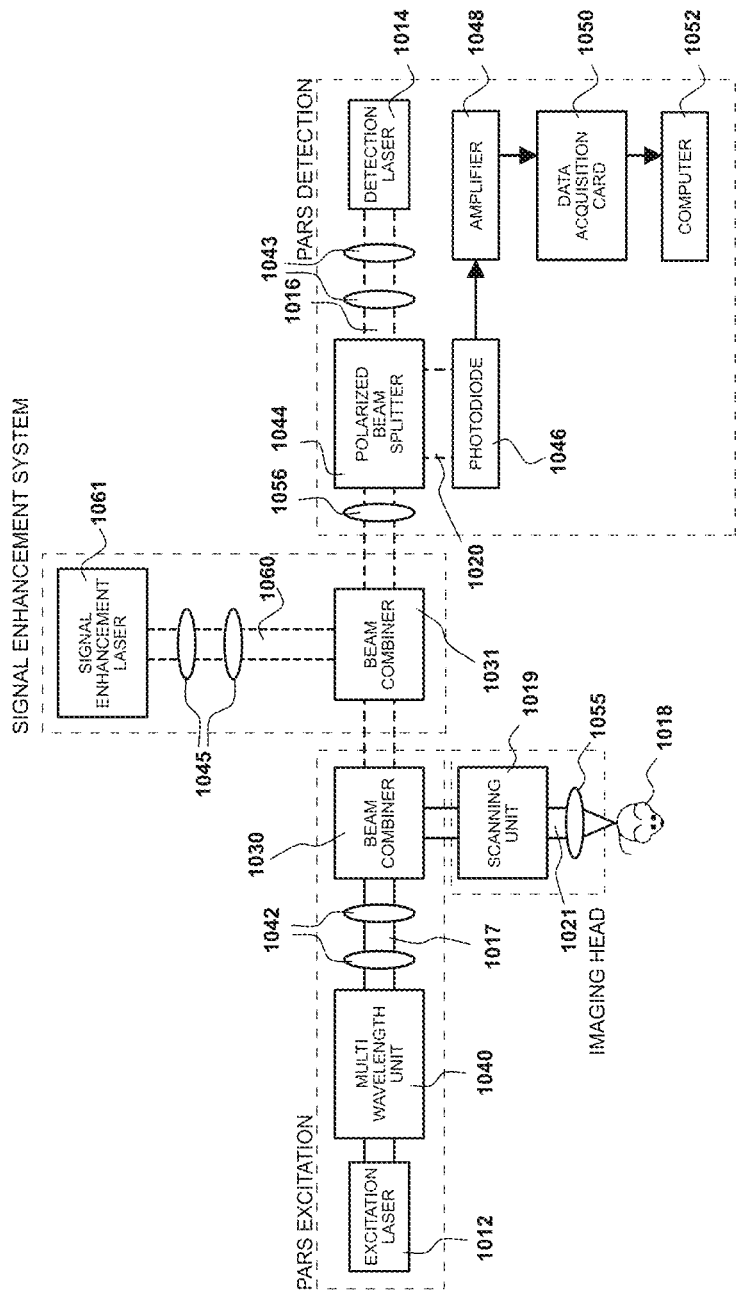
FIG. 10 Shows an example of a system layout for TE-PARS.

FIG. 10 shows one implementation of the TE-PARS. A multi-wavelength fiber excitation laser (1012) is used to generate PARS signals. An excitation beam (1017) passes through a multi-wavelength unit (1040) and a lens system (1042) to adjust its focus on the sample (1018). The optical subsystem used to adjust the focus may be constructed by components known to those skilled in the art including but not limited to beam expanders, adjustable beam expanders, adjustable collimators, adjustable reflective expanders, telescope systems, etc. The acoustic signatures are interrogated using either a short or long-coherence length probe beam (1016) from a detection laser (1014) that is co-focused and co-aligned with the excitation spots on the sample (1018). The interrogation/probe beam (1016) passes through a lens system (1043), polarizing beam splitter (1044) and quarter wave plate (1056) to guide the reflected light (1020) from the sample (1018) to the photodiode (1046). However, this architecture is not limited to including a polarizing beam splitter (1044) and quarter wave plate (1056). The aforementioned components may be substituted for fiber-based, equivalent components, e.g., a circulator, coupler, WDM, and/or double-clad fiber, that are non-reciprocal elements. Such elements may receive light from a first path, but then redirect said light to a second path. A signal enhancement laser (1061) is used to enhance the PARS signals using a signal enhancement beam (1060). The signal enhancement beam (1060) passes through a lens system (1045) to adjust its focus on the sample (1018). The signal enhancement beam (1060) is combined with the interrogation beam (1016) using a beam combiner (1031). The combined signal enhancement beam (1060) and interrogation beam (1016) are further combined with the excitation beam using another beam combiner (1030). The combined beam (1021) is scanned by a scanning unit (1019). This passes through an objective lens (1055) and is focused onto the sample (1018). The reflected beam (1020) returns along the same path and is reflected to the signal collection/analysis pathway by the polarized beam splitter (1044). The pathway consists of a photodiode (1046), amplifier (1048), fast data acquisition card (1050) and computer (1052). In some embodiments the signal enhancement beam may not be directed along the same pathway as the other beams as it does not necessarily need to be tightly focused on to the sample at the excitation location. The signal enhancement beam may include any one or more of the parameters of the interrogation beam of the excitation beam. The signal enhancement beam could be directed from any angle, using separate optics. The signal enhancement beam could be focused on unfocused. The signal enhancement beam can be pulsed, continuous and can be any wavelength depending on the sample.

Beam properties for the signal enhancement beam may be selected in order to provide the desired enhancement. Wavelength may be selected based on what would be appropriate for the desired contrast, within the same types of ranges as the excitation. Intensity would likely be comparably low compared to the other two beams, but again in similar types of ranges.

Figure 11:
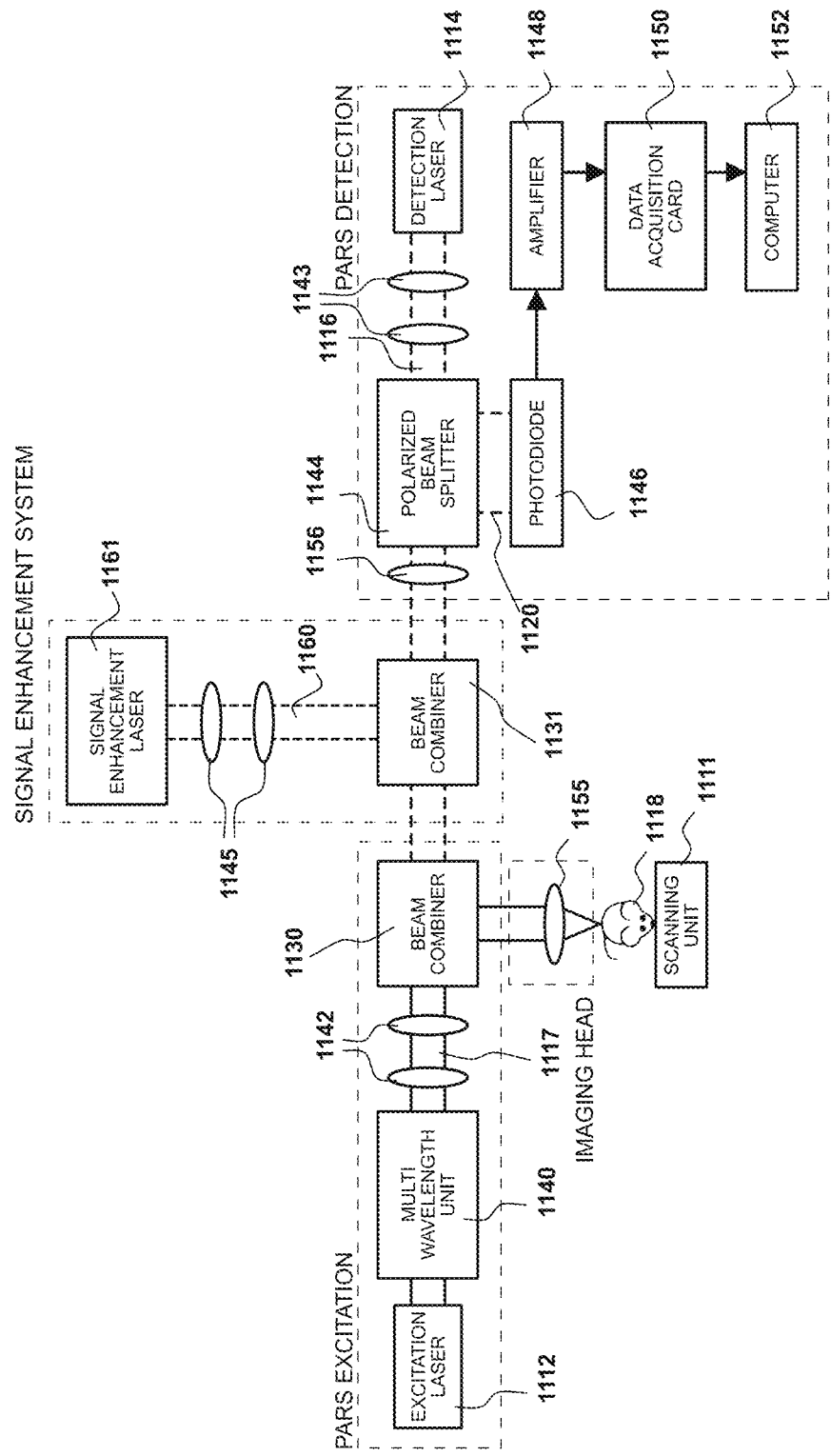
FIG. 11 Shows yet another example of a system layout for TE-PARS.

FIG. 11 shows another embodiment of TE-PARS. This implementation is similar to the one shown in FIG. 10 but uses a scanning unit (1111) to move the sample relative to the interrogation spot rather than scanning the interrogation spot about the sample. Components with similar labels to those in FIG. 10 serve similar purposes in this architecture.

Figure 12:
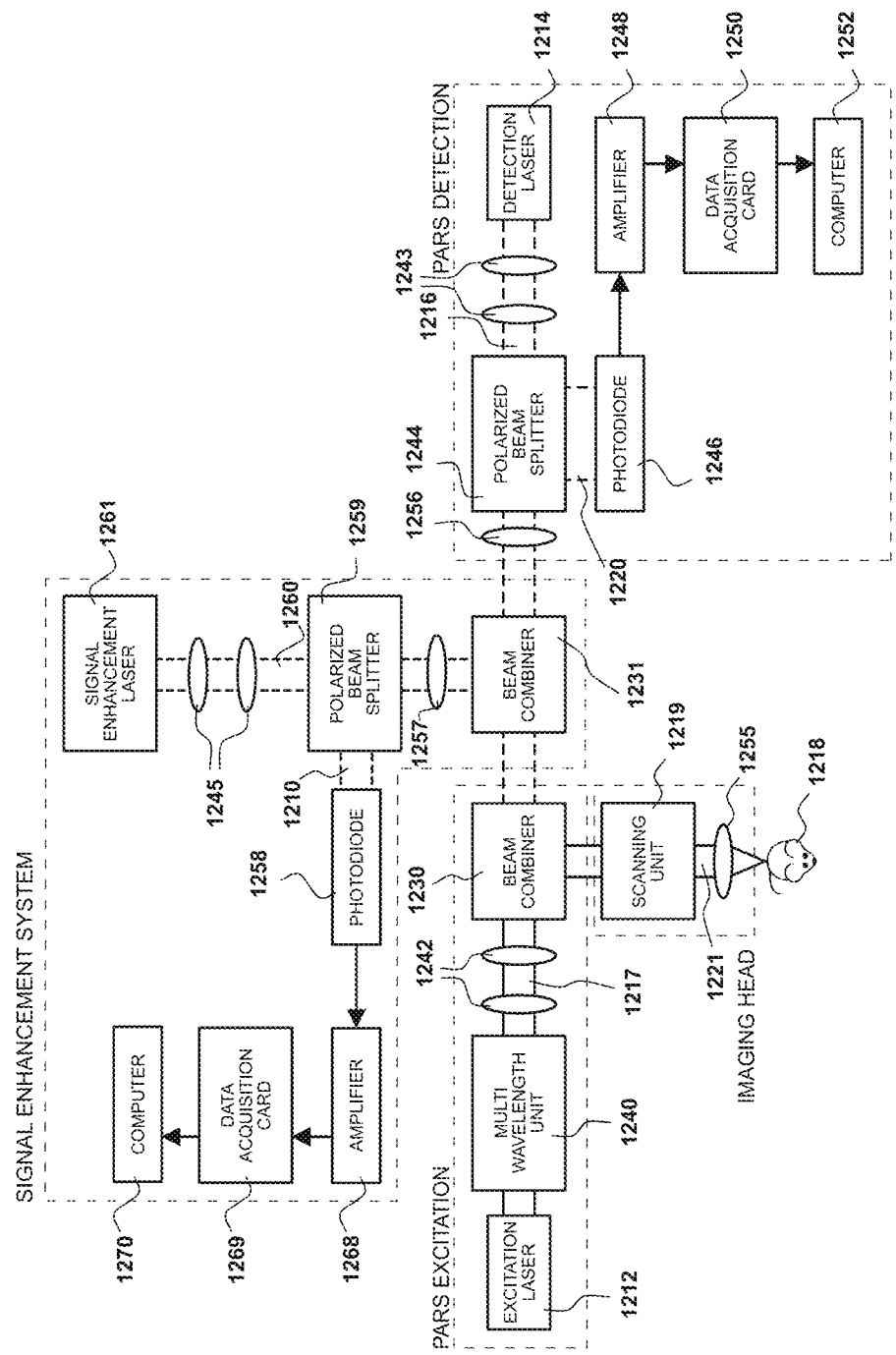
FIG. 12 Shows yet another example of a system layout for TE-PARS.

FIG. 12 shows yet another embodiment of TE-PARS. This implementation is similar to the one shown in FIG. 10 but adds components to collect and analyze the signal enhancement beam reflected from the sample (1210). The signal enhancement beam (1260) is passed through a lens system (1245), polarized beam splitter (1259) and quarter-wave plate (1257). The beam is co-focused with the interrogation beam (1216) and excitation beam (1217) on the sample. The reflected signal enhancement beam (1210) is reflected onto the signal collection pathway which consists of a photodiode (1258), amplifier (1268), data acquisition card (1269) and a computer (1270). Note that this particular example highlights a non-interferometric detection, however, signal enhancement detection may take the form of any previously recited PARS detection pathway including interferometric designs. Components with similar labels to those in FIG. 10 serve similar purposes in this architecture.

Figure 13:
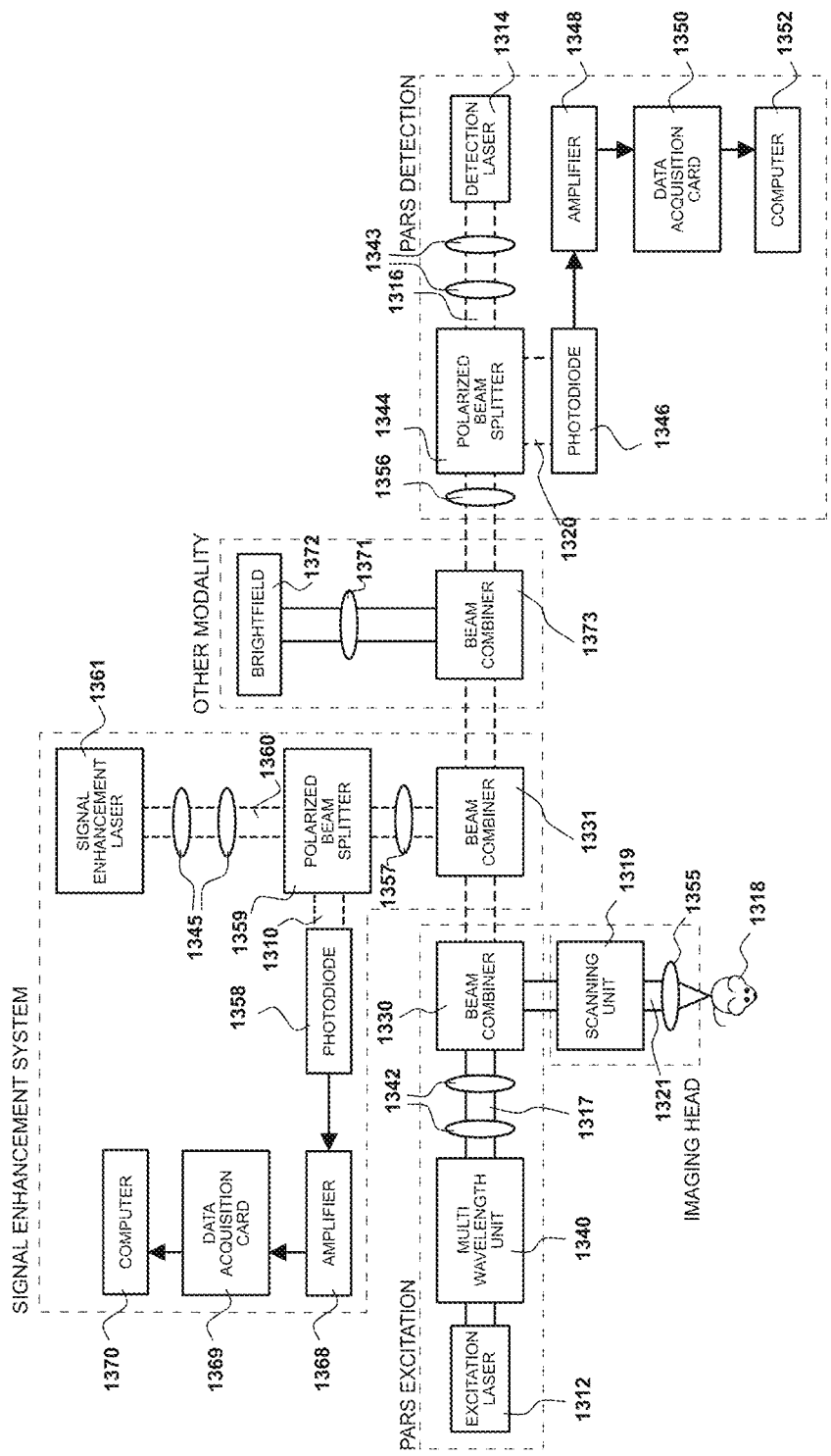
FIG. 13 Shows an example of combining TE-PARS with other modalities.

FIG. 13 shows yet another embodiment of a multi-modal TE-PARS system. This implementation is similar to FIG. 10 but adds bright-field detection in which a beam combiner (1373) directs light through a tube lens (1371) and onto a camera (1372). Additional modalities such as a bright-field microscopy, scanning laser ophthalmoscope, ultrasound imaging, stimulated Raman microscopy, fluorescence microscopy, two-photon and confocal fluorescence microscopy, Coherent-Anti-Raman-Stokes microscopy, Raman microscopy, other PARS, photoacoustic and ultrasound systems among others, maybe added in this manner. Components with similar labels to those in FIG. 10 serve similar purposes in this architecture. Such integrated additional pathways may need to operate on narrow wavelength bands which remain open on a unique paths towards the sample. This may involve careful selection of operating wavelengths between modalities. The potential benefit of such approaches is that a single contained device may be able to provide a wide complement of different modalities each with their own benefits. For example in FIG. 13, the addition of a camera allows for a traditional bright-field microscope which may provide different contrast and achieve a different imaging rates as opposed to the cointegrated PARS device.

Figure 14:
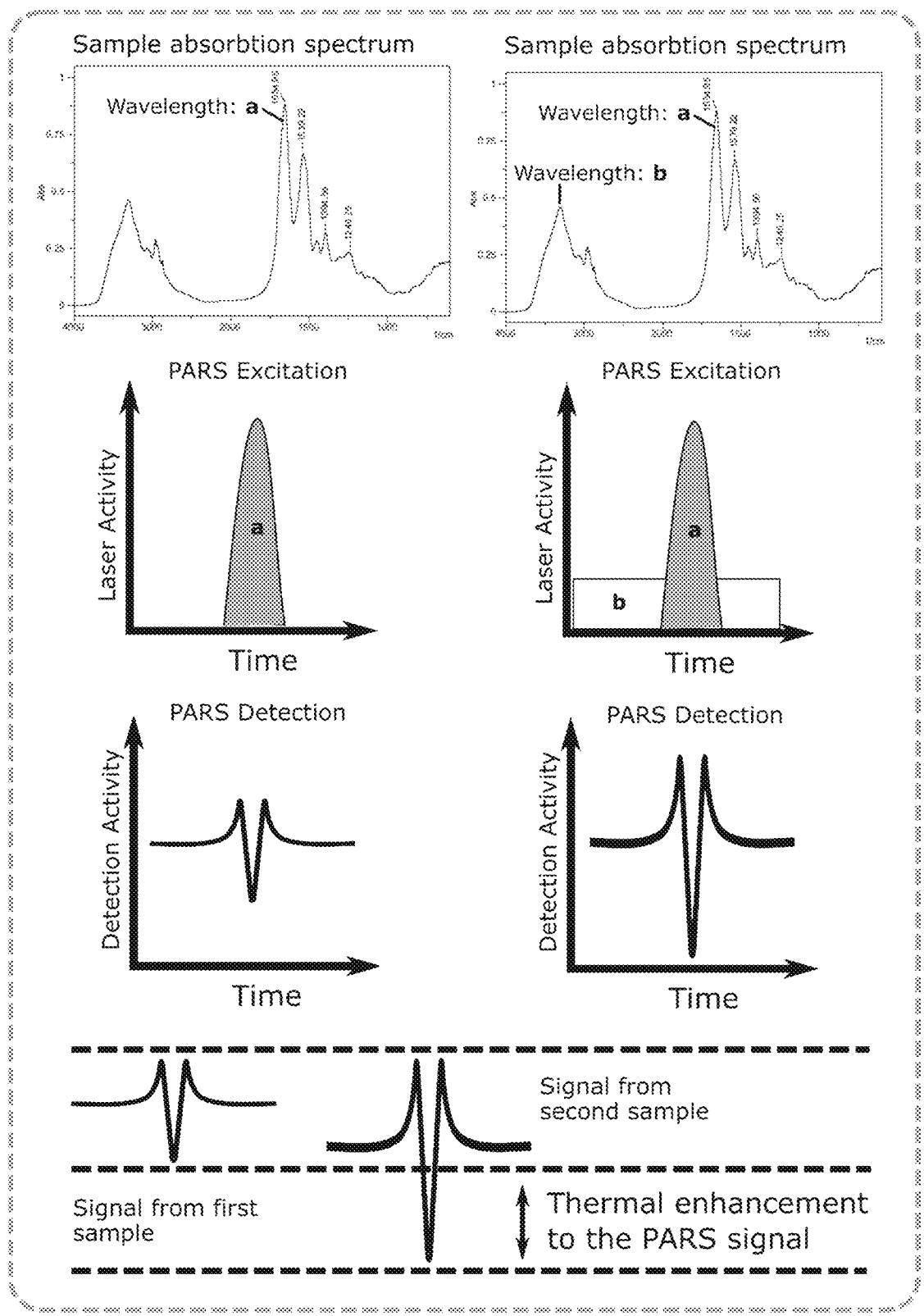
FIG. 14 Shows an example of a TE-PARS imaging method using continuous thermal enhancement.

FIG. 14 shows a comparison between a standard PARS acquisition (left) and a TE-PARS acquisition (right). The TE-PARS acquisition uses the additional heat (1 milliKelvin to 10 Kelvin, 20 Kelvin, 30 Kelvin, 40 Kelvin, 50 Kelvin, 60 Kelvin, 70 Kelvin, 80 Kelvin, 90 Kelvin, 100 Kelvin or more) generated by the signal enhancement laser to improve photoacoustic conversion efficiency resulting in larger modulations in the back reflected intensity from that region. This additional signal may be used to simply enhance overall fidelity, or to highlight contrast from a wavelength different from the excitation. In some examples, TE-PARS may enhance signal-to-noise ratio by at least 5 percent. In some examples, TE-PARS may achieve a photoacoustic conversion efficiency of up to 1000%. For example, here the excitation uses wavelength "a" to capture a baseline PARS signal. Then, another acquisition is taken with the same excitation wavelength but now using a signal enhancement laser emitting wavelength "b". The difference between these two signals can then be directly attributed to the absorption at the signal enhancement wavelength.

Figure 15:
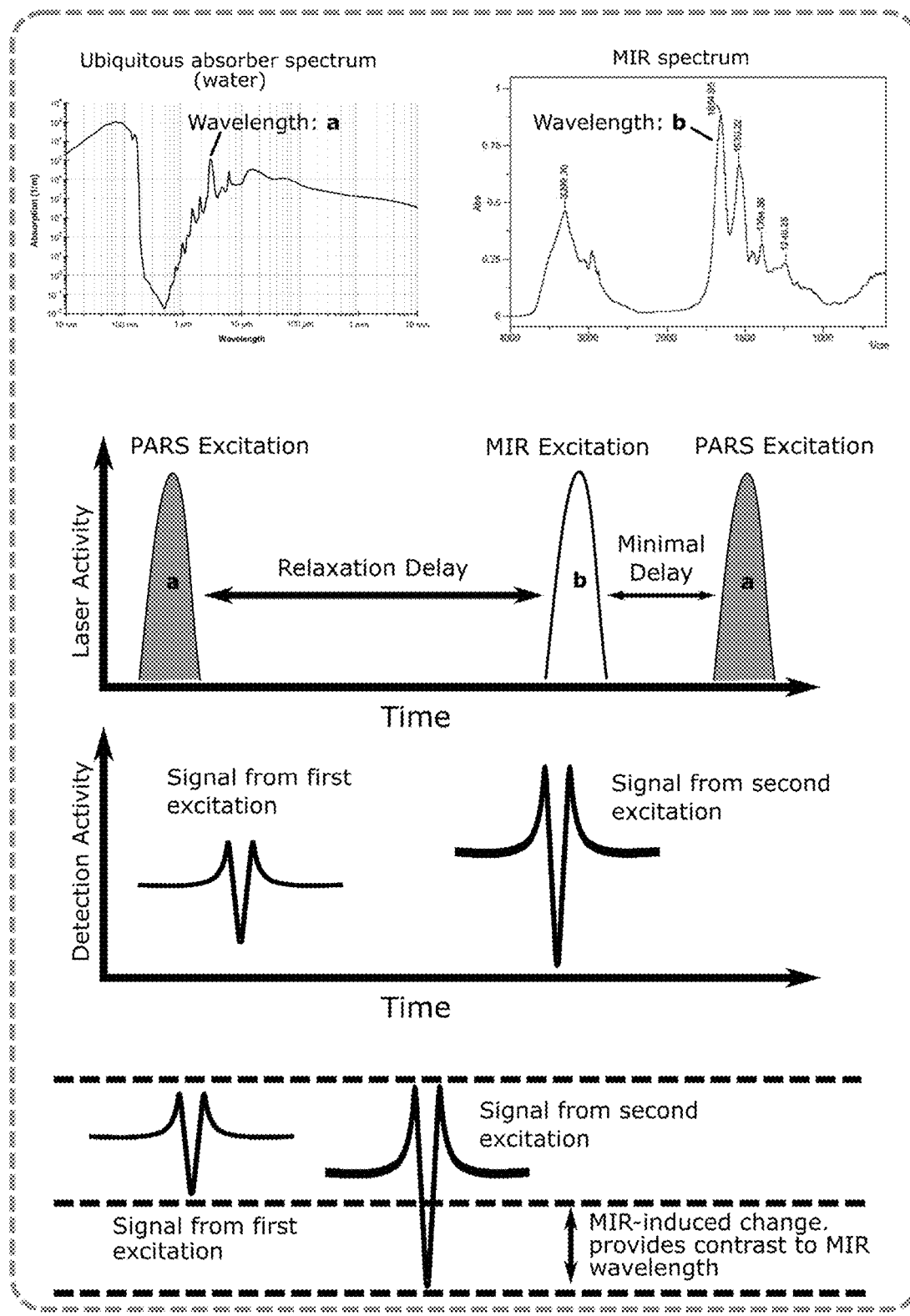
FIG. 15 Shows an example of a TE-PARS imaging method using pulsed thermal enhancement.

FIG. 15 shows an example of the signal acquisition process used by a TE-PARS with a pulsed signal enhancement beam. In this example, a mid-infrared (MIR) enhancement beam is used between two standard PARS acquisitions. One of these PARS acquisitions directly follows the MIR pulse such that it experiences additional PARS excitation brought on by a temperature rise introduced by the MIR excitation.

Figure 16:
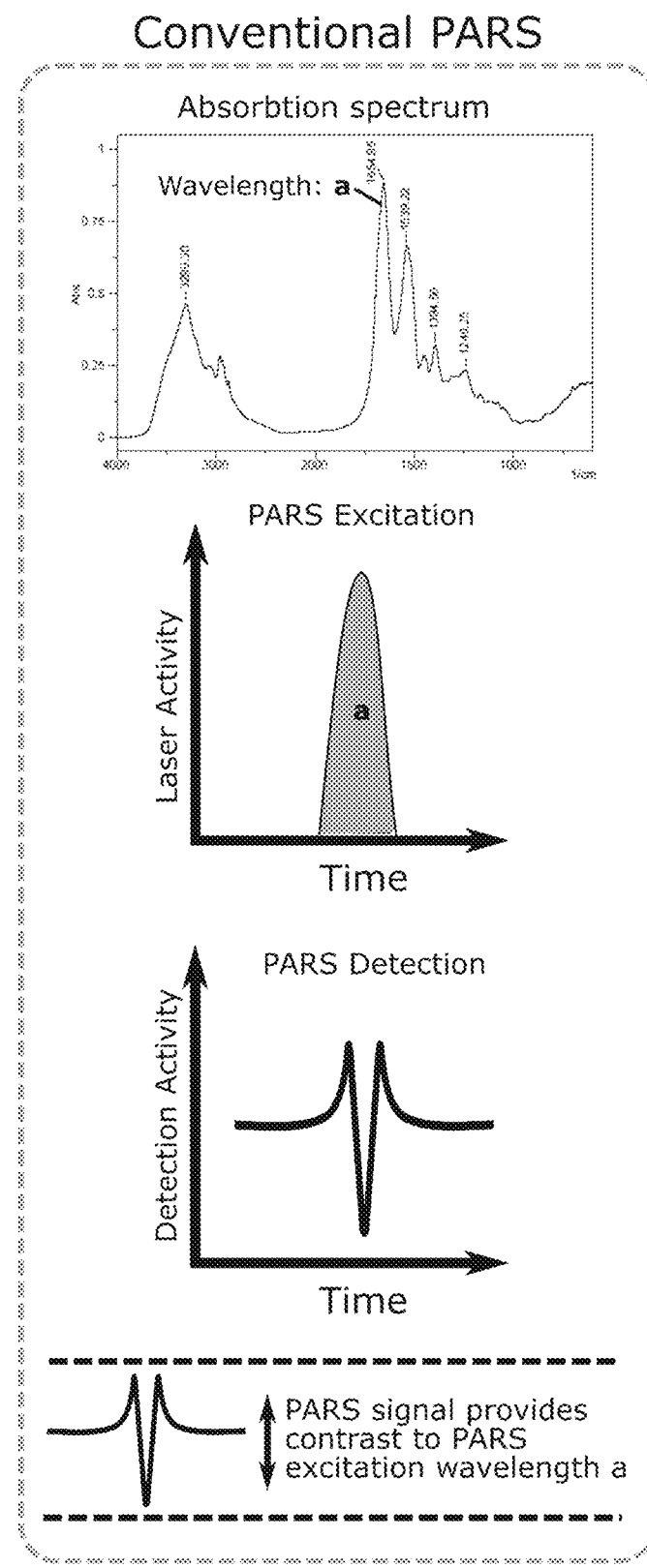
FIG. 16 Shows a diagram of the signal generation in a PARS system.

FIG. 16 shows an example of the signal acquisition process used by a standard PARS acquisition. Signal generation is solely based on absorption of the excitation pulse.

Figure 17:
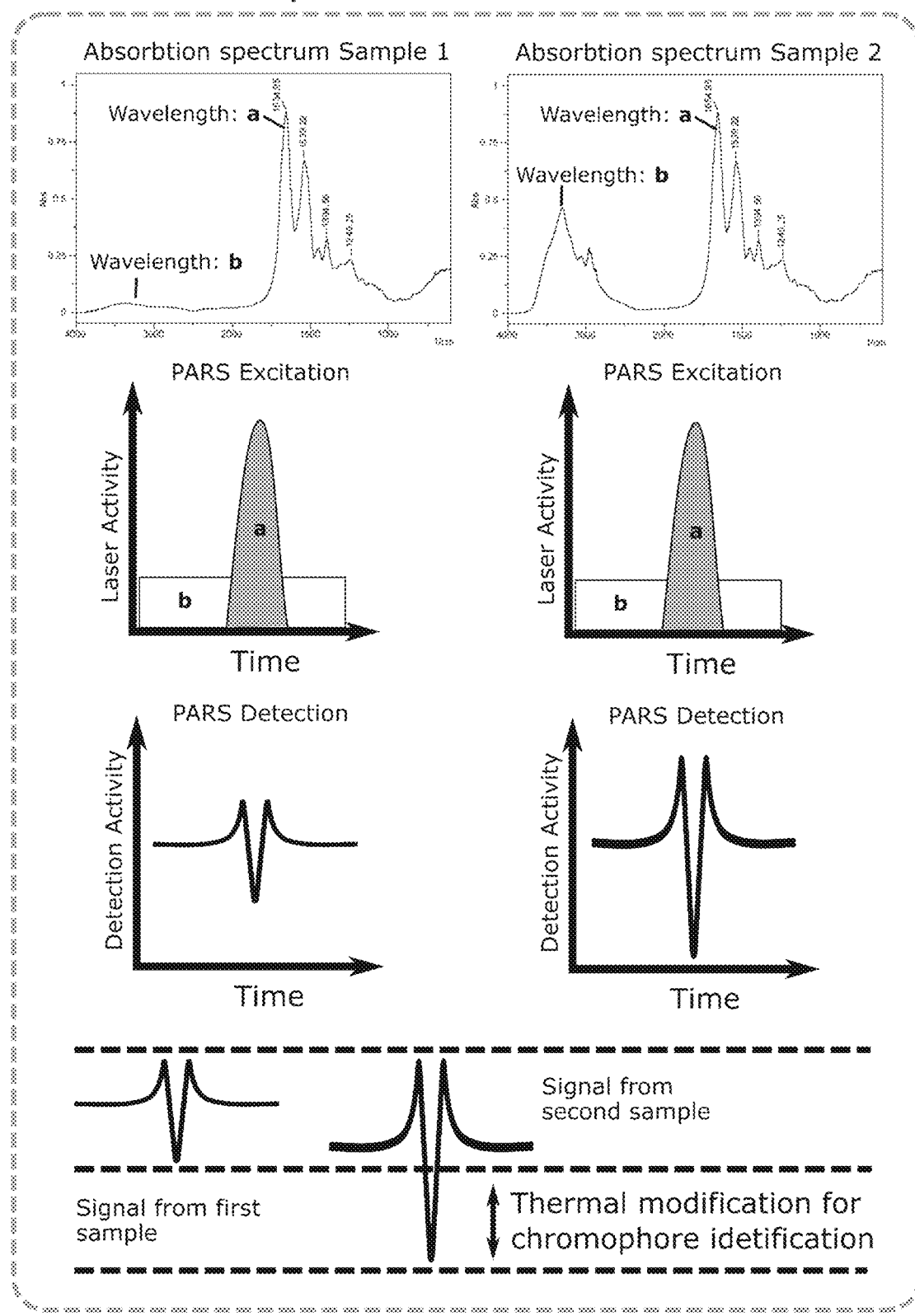
FIG. 17 Shows a diagram of a TE-PARS signal unmixing method.

FIG. 17 shows an example of the signal acquisition process used by a TE-PARS which is conducting a multiplex acquisition. In conventional photoacoustics, multiplex acquisitions are carried out by using multiple excitation wavelengths. However, a TE-PARS may use a single excitation wavelength alongside different signal enhancement wavelengths. As such, this approach may be used to separate multiple chromophores based on their optical absorption at the signal enhancement wavelengths. This could facilitate visualization of independent constituent components (such as chromophores) despite each individual original dataset providing a super position of these constituents. In some embodiments, the system may unmix different chromophores from each other (as they may be mixed in a complex tissue) such as hemoglobin, DNA and lipids. Then, they can be given different color maps and can be shown in one image. Furthermore, now the chromophores/targets can be easily distinguished by looking at the image.

Figure 18:
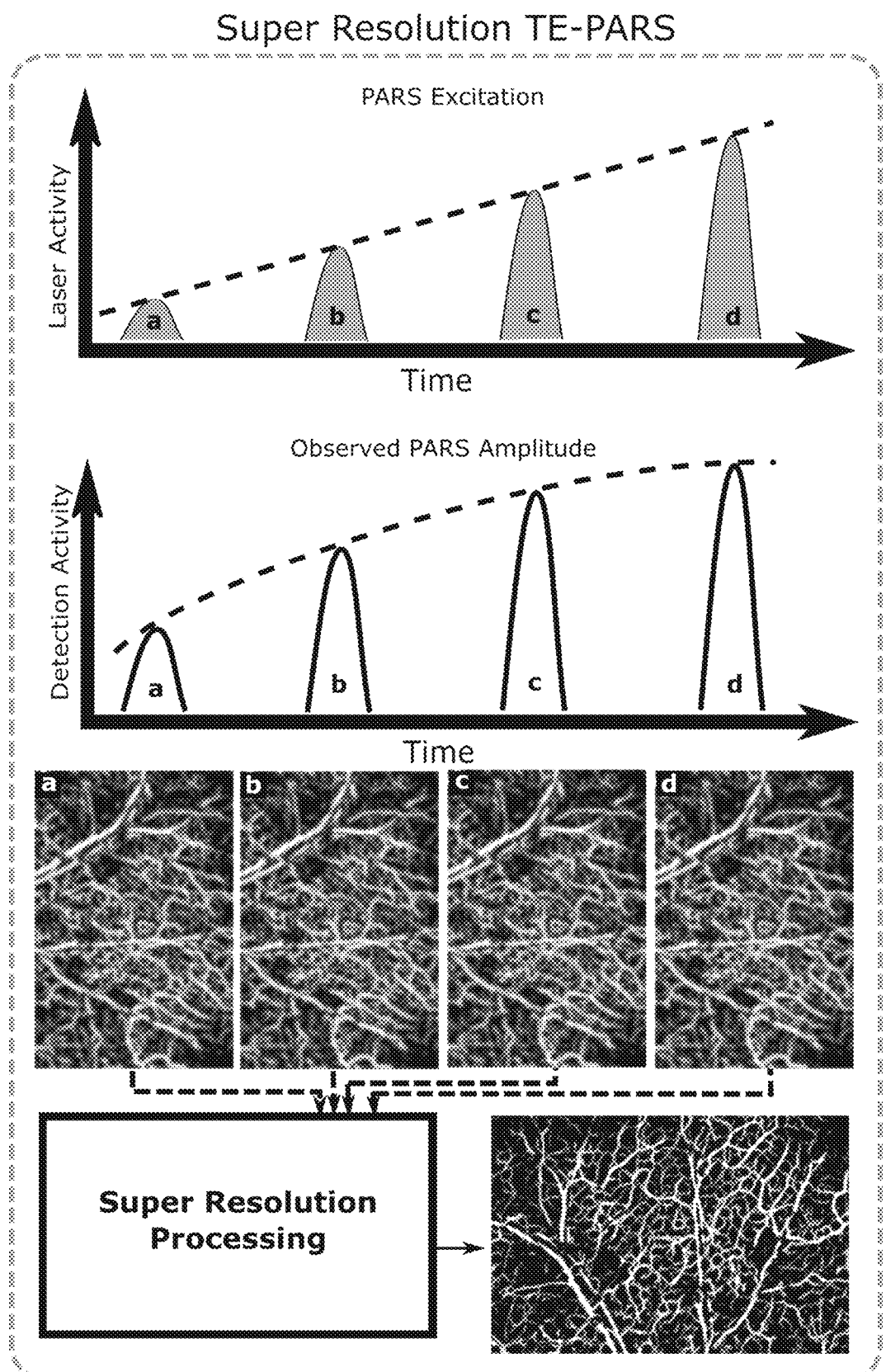
FIG. 18 Shows a signal flow for super-resolution imaging.

FIG. 18 shows an example of the signal acquisition process used by a SR-PARS. Multiple standard PARS acquisitions are performed at various known excitation energies. Due to saturation effects, the observed output PARS signals may in turn provide a non-linear relation to these excitation energies. Resolutions tighter than the optical diffraction limit may be achieved with such a system by leveraging nonlinear optical absorption contrast effects within the sample such as optical intensity-induced optical absorption attenuation (sometimes called photobleaching), and nonlinear thermal dependencies of material properties such as the thermal expansion coefficient. This algorithm may use as inputs several scans of a sample of such that non-linear PARS signal generation may occur across acquisitions allowing for the application of a Vandermonde matrix-based process for separating N'th order power relationships. These non-linear effects can be leveraged by PARS super-resolution processing algorithms to then extract higher order spatial frequencies resulting in improved resolution which may reach beyond the optical diffraction limit.

Figure 19:
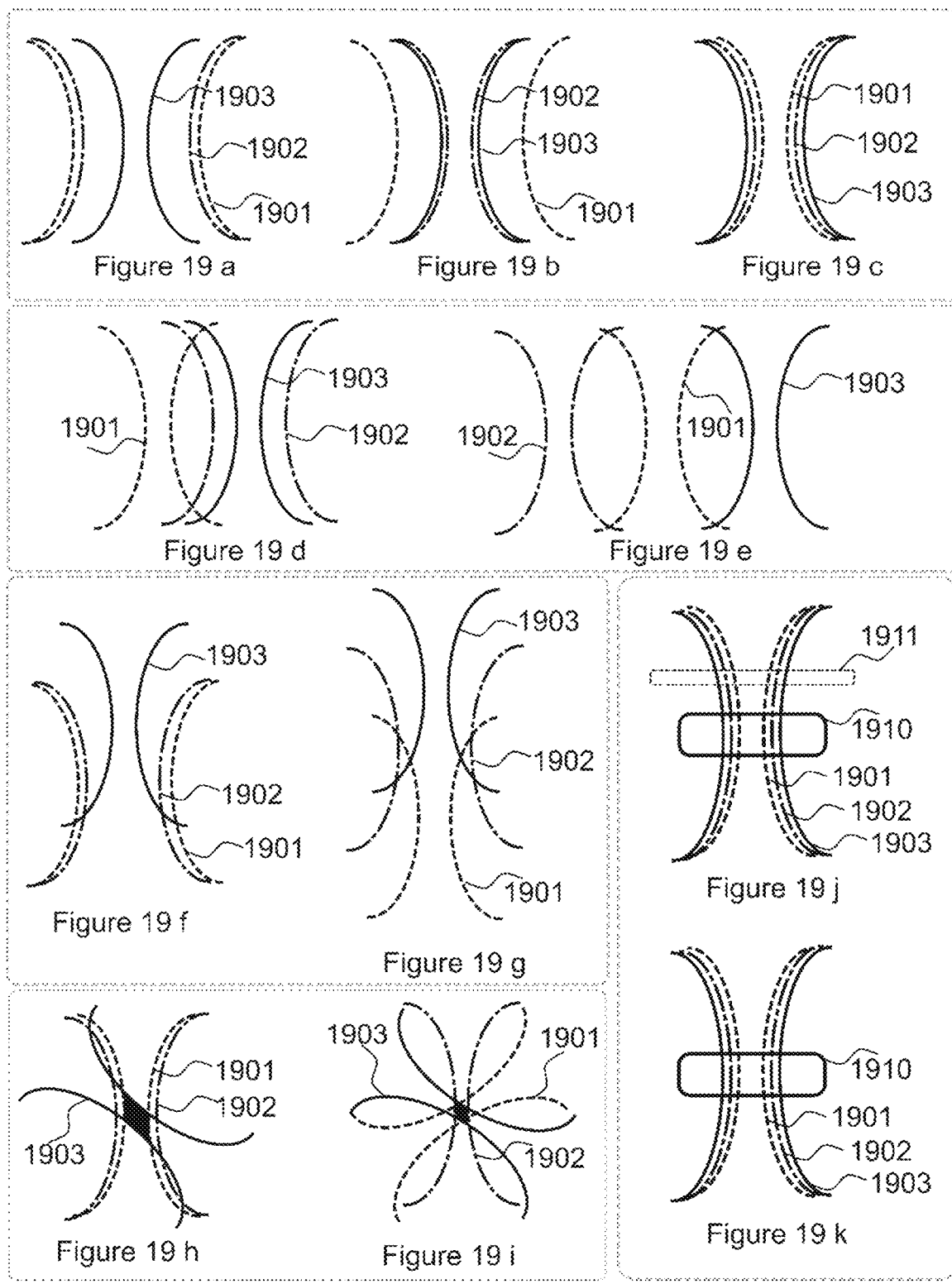
FIGS. 19A-K Show different spot arrangements.

FIG. 19 shows an example of several local spot positioning conditions. Each of the respective beams (1901), (1902), (1903) may represent any of the excitation, detection, or signal enhancement beams. FIG. 19a highlights an orientation where one of the excitation, detection, and signal enhancement beams forms a smaller focal spot as compared to the other two beams. Likewise, FIG. 19b highlights an alternate case wherein two of the excitation, detection, and signal enhancement beams form smaller focal spots than the third beam. FIG. 19c exemplifies a third case where in each of the excitation, detection and signal enhancement beams form nearly equivalent focal spots. FIGS. 19d and 19e, show focal conditions where in the spots of the constituent beams do not perfectly overlap at the focal spot but are displaced in the lateral direction. In the first case (FIG. 19d) a singular beam is displaced while the other two remain overlapped, in the second case (FIG. 19e) all three beams are displaced relative to each other. Similar to FIGS. 19d and 19e, FIGS. 19f and 19g, show focal conditions where the spots of the constituent beams do not overlap at the focal spot but are displaced in the axial direction. In the first case (FIG. 19f) a singular beam is displaced while the other two remain overlapped, in the second case (FIG. 19g) all three beams are displaced relative to each other. These displacements may be any reasonable value depending on the requirements of the imaging session. FIG. 19h and FIG. 19i highlight conditions where the central beam axes form an angle between themselves and between the sample, where this angle may commonly range between 5 and 90 degrees with the sample surface. FIG. 19h highlights the case where two of the beams remain co-aligned while the angle of the third beam is modified. FIG. 19i shows the case where each of the beams holds an independent angle relative to the others. Finally, FIG. 19j and FIG. 19k show two different cases for scanning a sample (1910). In FIG. 19k the sample is placed directly within the path of the beams, alternatively in FIG. 19j there is some scattering media or optical window (1911) located in the beam path prior to the sample, an example of a common media within the beam path before the sample would be a glass slide or cover slip to contain the sample. This diagram is not meant to be limiting and has obvious extensions where the system comprises more than three beams. These various conditions may be controlled by adjusting beam alignment into one or more focusing optics. For example, the excitation may be steered to one side relative to the other beams to produce a condition similar to FIG. 19d. Likewise, the excitation focus may be moved axially relative to the other two beams to produce a condition similar to FIG. 19f. It may be desirable to purposely misaligned these foci in some instances such as rapid optical scanning in which it may be desirable to, for example, have the interrogation point trail the excitation point to compensate for the rapid focal scanning. Angling the beams relative to each other (FIGS. 19h & 19i) may provide improvements to detection sensitivity and due to the higher prevalence of a lateral optical scattering as opposed to a back-optical scattering. Another benefit may come from utilizing the tight lateral focus of the one beam to compensate for the comparably poor axial focus of another beam by having them overlap each other at around 90 degrees.

Figure 20:
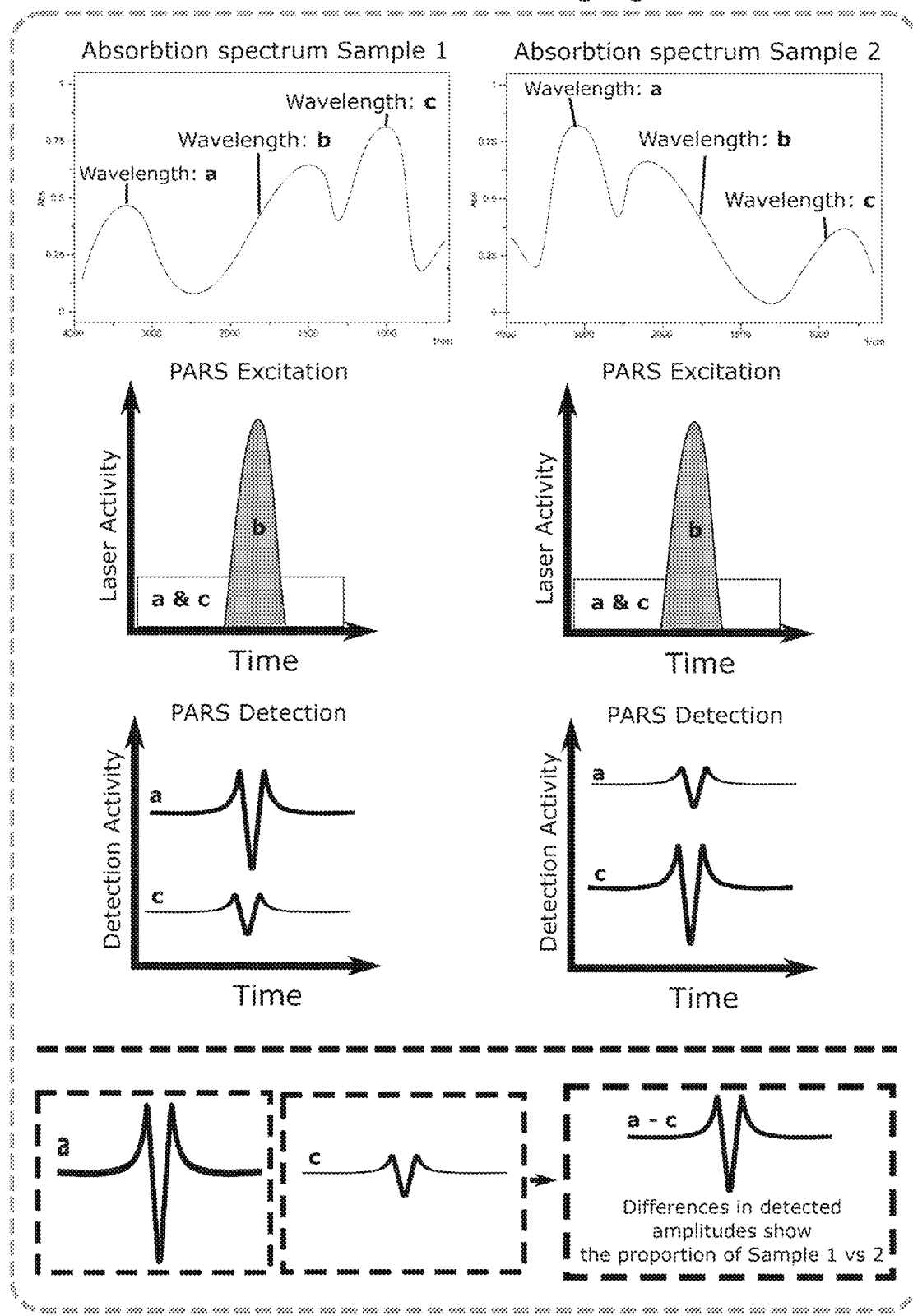
FIG. 20 Shows an example of a TE-PARS-based functional imaging method.

FIG. 20 shows another example of signal processing used by a TE-PARS to conduct multiplex acquisitions. Here, thermal effects are used to measure the proportion of two constituent chromophores. In one instance (sample 1), the absorption of detection wavelength "c" is higher than that of "a" resulting in a lower returned signal at wavelength "c" and a higher returned signal at wavelength "a". Likewise, in sample 2 the absorption of detection wavelength "a" is higher than that of "c" resulting in a higher returned signal at wavelength "c" and a lower returned signal at wavelength "a". These differences in returned amplitude are primarily attributed to the difference in the optical absorption of the target to each of the wavelengths "a" and "c". Moreover, the proportion of sample 1 and sample 2 may be determined based on the proportionality of returned signal at wavelength "a" compared to wavelength "c". By leveraging the thermal enhancement effects in this way, it is possible to perform chromophore unmixing utilizing only a single excitation source.

Figure 21:
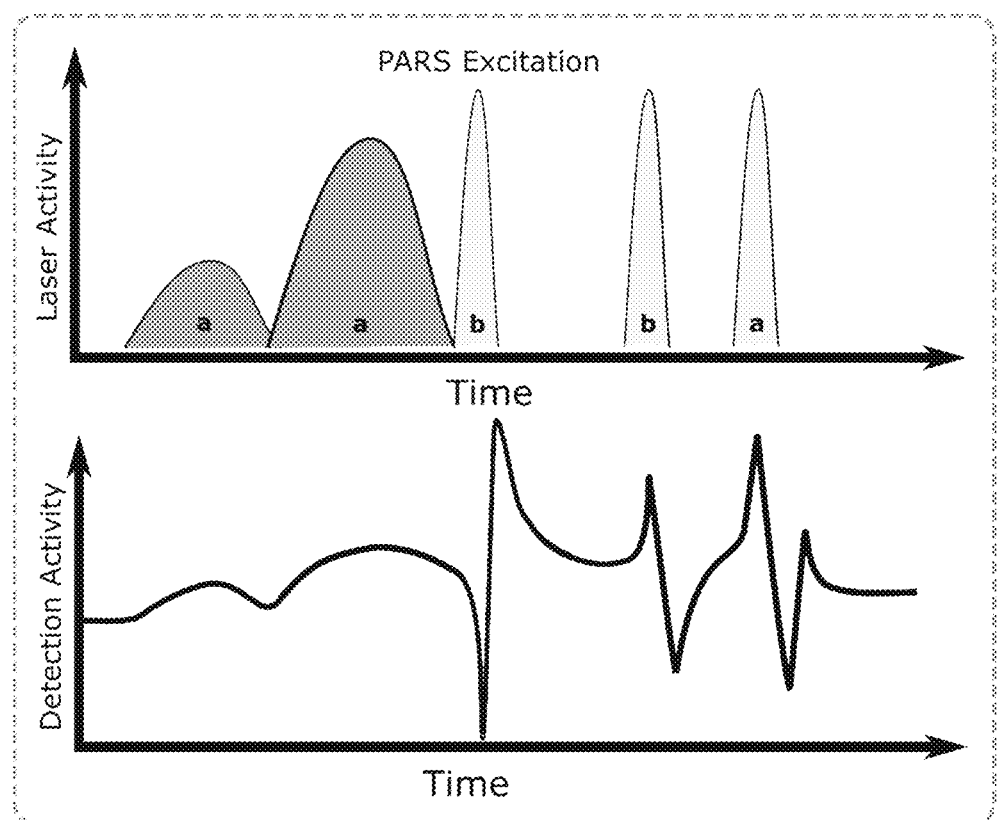
FIG. 21 Shows an example of a PARS excitation series and the resulting PARS signal.

FIG. 21 shows an example of a TE-PARS system which utilizes a customized excitation pulse train of varying pulse widths, energies, wavelengths, and pulse timing to induce specific thermal and pressure effects within the sample. These pulse trains can be used to shape and design specific customized PARS signals. Moreover, such excitation pulse trains may be leveraged to enhance signals from specific chromophores, suppress signals from specific chromophores, generate signals of a specific shape and frequency to aid in signal extraction, etc. For example, a secondary pulse may be timed relative to a first pulse such that the relaxation period of the first signal is coincident with the peak of the second signal as to further augment the overall signal amplitude.

Figure 22:
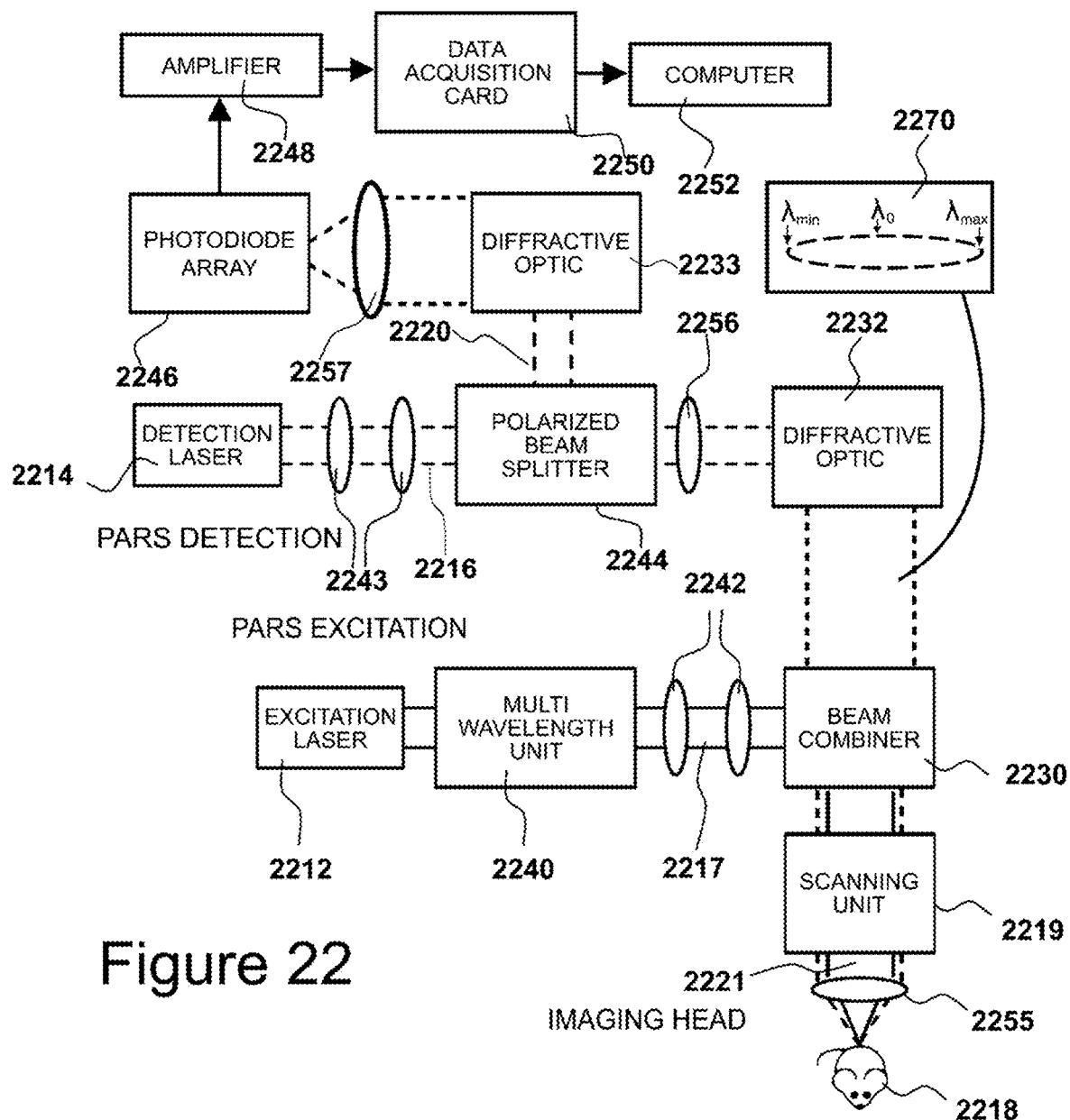
FIG. 22 Shows a implementation of the SE-PARS system.

FIG. 22 demonstrates implementations of the SE-PARS detection system. This implementation is utilizing a similar PARS excitation and delivery system as those shown in FIG. 10 through FIG. 13. but adds components to encode information relating to the spatial distribution of focal points in the focal plane within the spectral domain of the detection beam (2270). This may omit the requirement for optical or mechanical scanning for small field of views, and may facilitate encoding of spatial information through single fibers where the spatial distribution is encoded within the spectral distribution. The detection beam (2216) is passed through a lens system (2243), polarized beam splitter (2244) and quarter-wave plate (2256). The beam is then passed through a diffractive optic (2232) which laterally spreads the detection beam based on the light wavelength. The broadened beam is then co-focused with the excitation beam (2221) on the sample (2218) through the scanning unit (2219) and the objective lens (2255). The reflected signal detection beam (2220) is reflected onto the signal collection pathway which consists of another diffractive optic (2233) which laterally spreads the detection beam based on the light wavelength, a lens (2257) to focus the light onto the photodiode array, a photodiode array (2246), amplifier (2248), data acquisition card (2250) and a computer (2252). Components with similar labels to those in FIG. 10 serve similar purposes in this architecture.

A TE-PARS, TS-PARS, SE-PARS, SD-PARS or SR-PARS could also be envisioned which uses a single optical source for all constituent paths or collection of paths for the PARS excitation, PARS detection, signal enhancement pathways. In any of these modalities one or more of the beam pathways may be oriented in transmission mode meaning that collection optics are placed on the opposite side of the sample to optics directing light at the sample.

Figure 23:
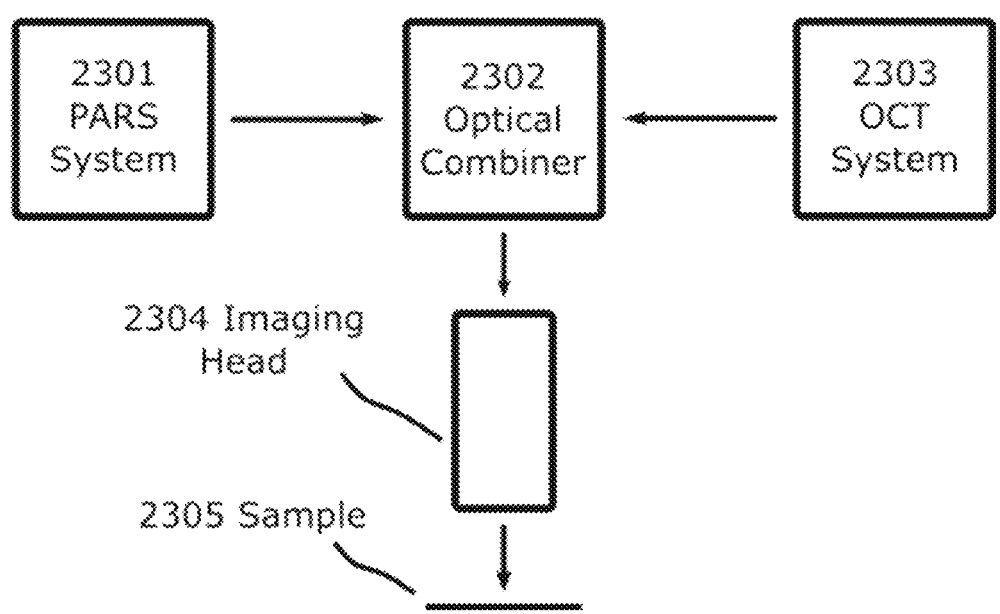
FIG. 23 Shows an overview of the PARS-OCT system.

FIG. 23 shows a high-level overview of a PARS-OCT system. This consists of a PARS imaging system (2301), an OCT imaging system (2303), an optical combiner (2302), and an imaging head (2304) which focuses beam paths onto the sample (2305).

Figures 24A, 24B:
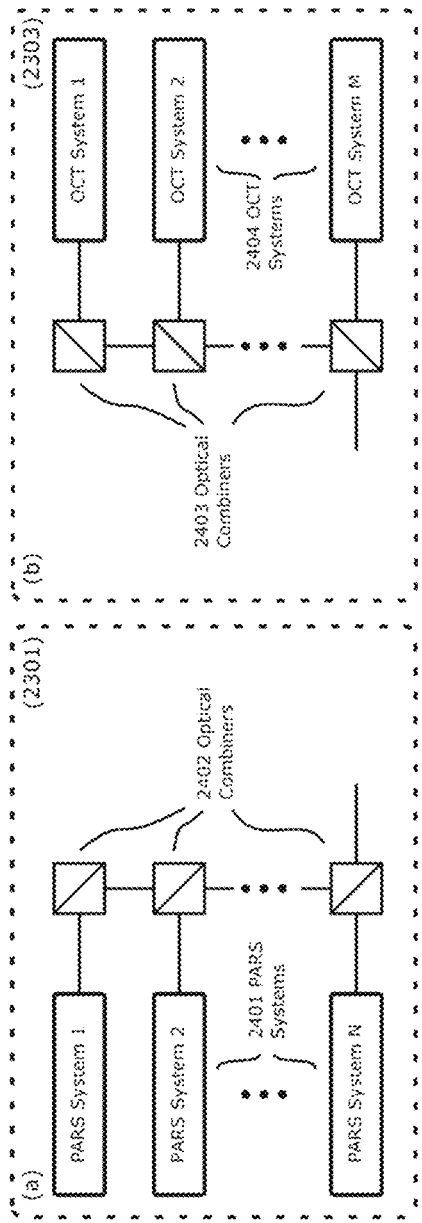
FIGS. 24a-b Show implementations of the PARS-OCT system imaging arms.

FIG. 24 demonstrates implementations of the PARS imaging subsystem (2301) and OCT imaging subsystem (2303). FIG. 24 (a) shows one implementation of the PARS subsystem (2301) which consists of one or more PARS systems (2401) of one or more PARS system configurations (1, 2, .

. . N) which may include, but is not limited to: single source, dual source, pulsed detection, etc. The output of which are then coupled through optical combiners (2402) which may be implemented with devices such as: free space beam combiners, free space dichroic mirrors, fiber-based interferometers, fiber-based couplers, etc. FIG. 24 (*b*) shows one implementation of the OCT subsystem (2303) which consists of one or more OCT systems (2404) of one or more OCT system configurations (1, 2, . . . , M) which may include, but is not limited to: spectral-domain OCT (SD-OCT), swept-source OCT (SS-OCT), time-domain OCT (TD-OCT), full-field OCT (FF-OCT), line-field OCT (LF-OCT), polarization-sensitive OCT (PS-OCT), Gabor-domain OCT (GD-OCT), etc. The output of which are then coupled through optical combiners (2403) which may be implemented with devices such as: free space beam combiners, free space dichroic mirrors, fiber-based interferometers, fiber-based couplers, etc.

Figure 25:
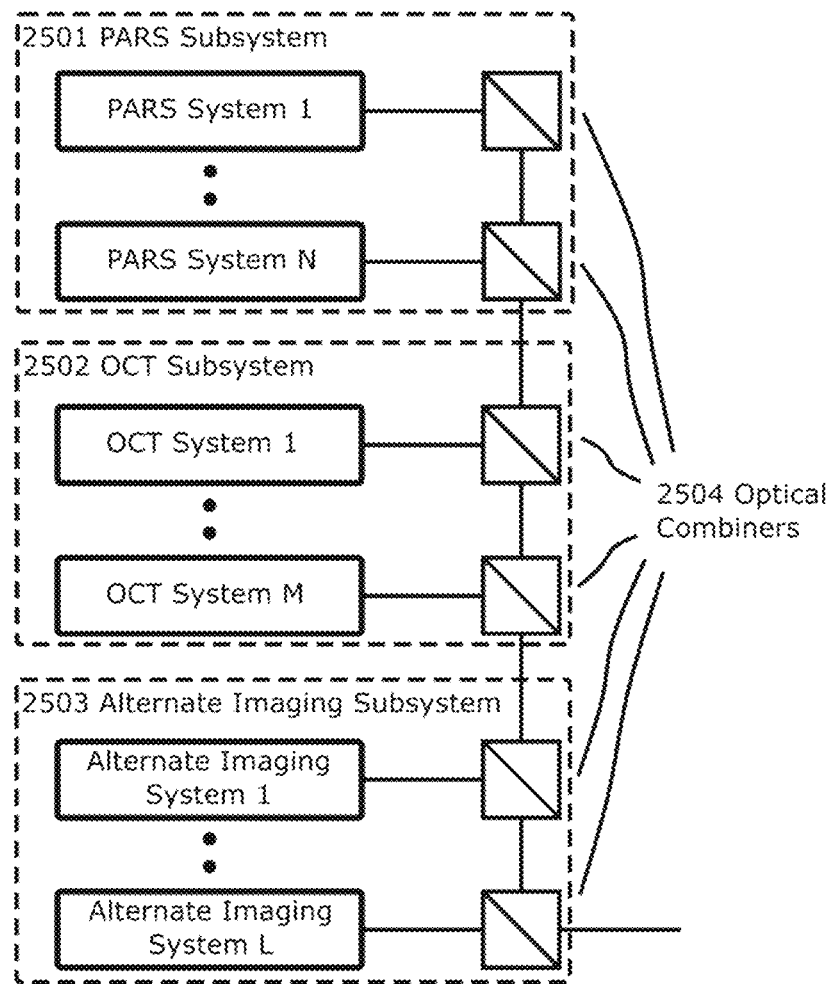
FIG. 25 Shows implementations of the PARS-OCT system.

FIG. 25 demonstrates the combination of a PARS subsystem (2501), an OCT subsystem (2502), as described in FIG. 24 with an additional alternate imaging subsystem (2503). The alternate imaging subsystem may be, but is not limited to: bright-field microscopy, scanning laser ophthalmoscope, ultrasound imaging, stimulated Raman microscopy, fluorescence microscopy, two-photon and confocal fluorescence microscopy, Coherent-Anti-Raman-Stokes microscopy, Raman microscopy, other PARS, photoacoustic and ultrasound systems, etc. These subsystems (2501, 2502, 2503) are then combined through optical combiners (2504) which may be implemented with devices such as: free space beam combiners, free space dichroic mirrors, fiber-based interferometers, fiber-based couplers, etc.

Figure 26A:
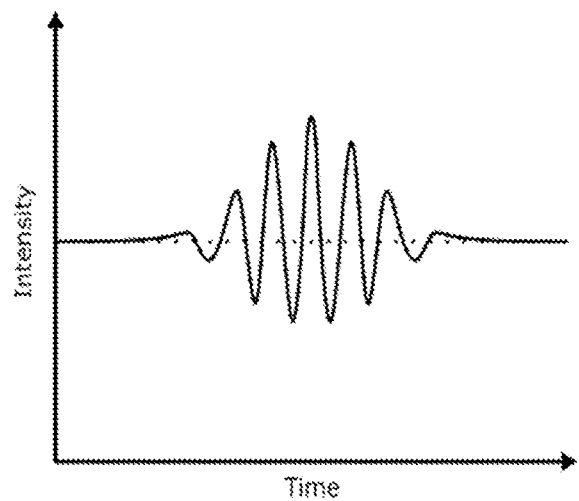
FIGS. 26a-c Shows mechanisms of OCT imaging systems.
Figure 26B:
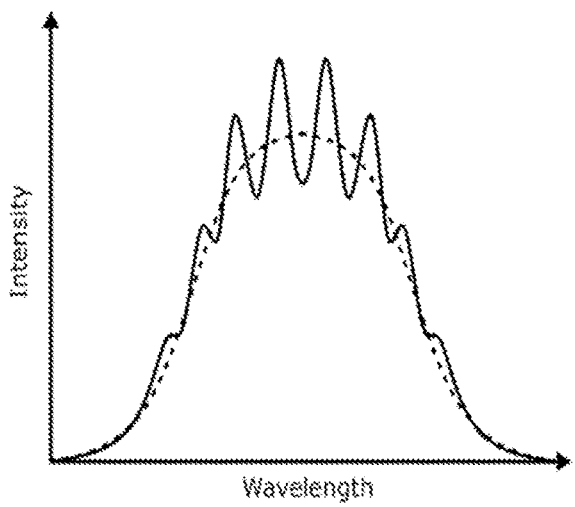
Figure 26C:
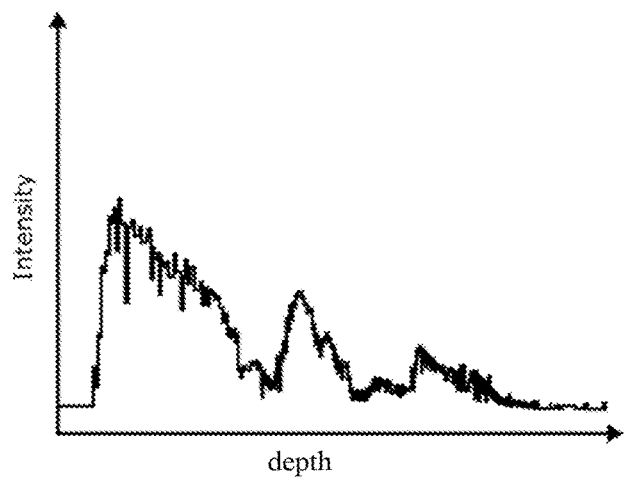

FIG. 26 describes the mechanism through which OCT signals are generated and captured. FIG. 26 (*a*) shows a representative example of a time domain interferogram for a specific depth. FIG. 26 (*b*) shows a representative example of a Fourier domain interferogram for an OCT system. FIG. 26 (*c*) shows a representative example of an A-scan for an OCT system which attempts to capture scattering contrast in depth.

FIG. 27 describes the signal processing pathway for an example OCT system. The OCT optical detector signal (2701) may be captured with devices including, but not limited to: photodiodes, avalanche photodiodes, phototubes, photomultipliers, CMOS cameras, CCD cameras (including EM-CCD, intensified-CCDs, back-thinned and cooled CCDs), spectrometers, etc. This signal may then undergo analog signal processing (2702), which may include, but is not limited to low-pass filtration, high-pass filtration, amplification, attenuation, etc. Additionally, the signal may also be fed through an alternate path (2703) to highlight different signal characteristics, leveraging alternate analog processing or lack thereof. The processed or/and unprocessed OCT signal then undergoes signal digitization (2704). This digital signal then undergoes digital signal processing (2705), which may include, but is not limited to low-pass filtration, high-pass filtration, Hilbert transformation, Fourier transforms, etc. From this fully processed signal, in some embodiments, key features may be extracted (2706) to produce an OCT image, which may include, but is not limited to techniques such as: absolute maximum projection, etc.

Figure 28:
FIG. 28 Shows an example OCT image of the human retina (B-scan).

FIG. 28 depicts a representative OCT image (B-scan) of the human retina. This image was captured with a SS-OCT system, and demonstrates significant scattering contrast allowing for detailed analysis of retina physiology.

Figure 29A:
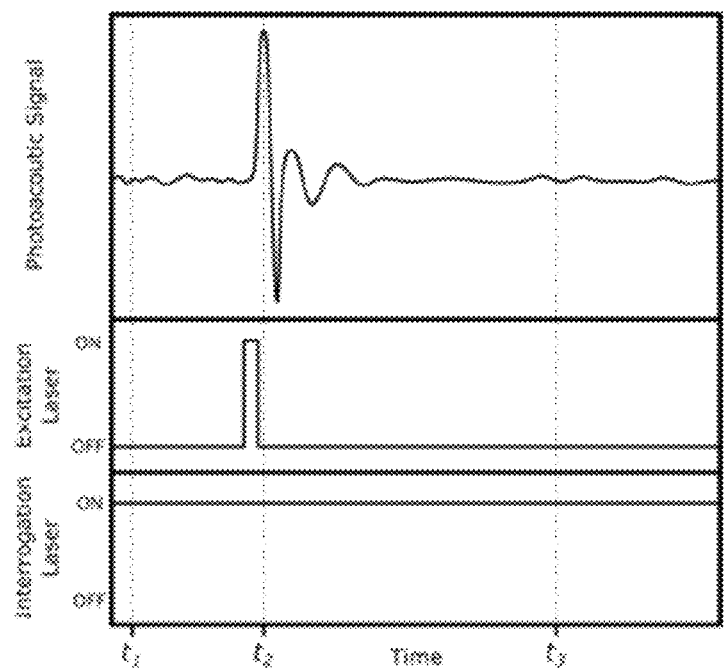
FIGS. 29a-c Show mechanisms of PARS imaging systems.
Figure 29B:
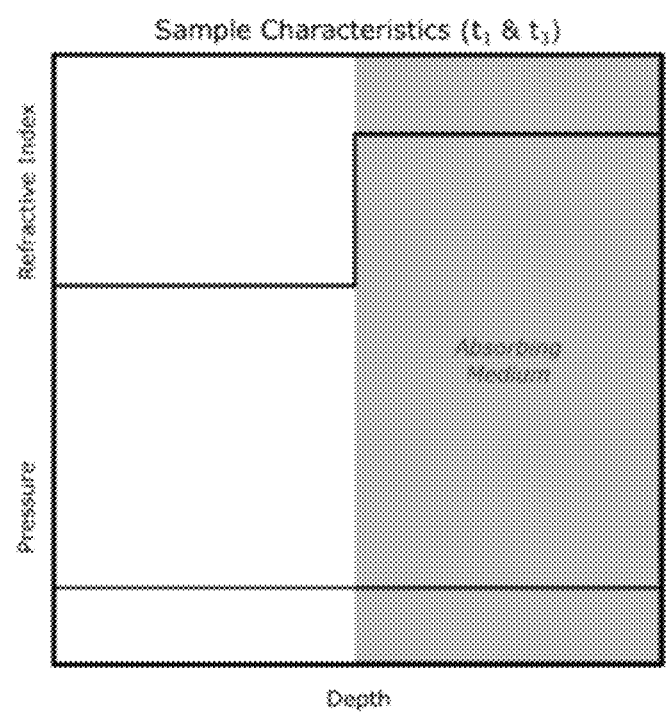
Figure 29C:
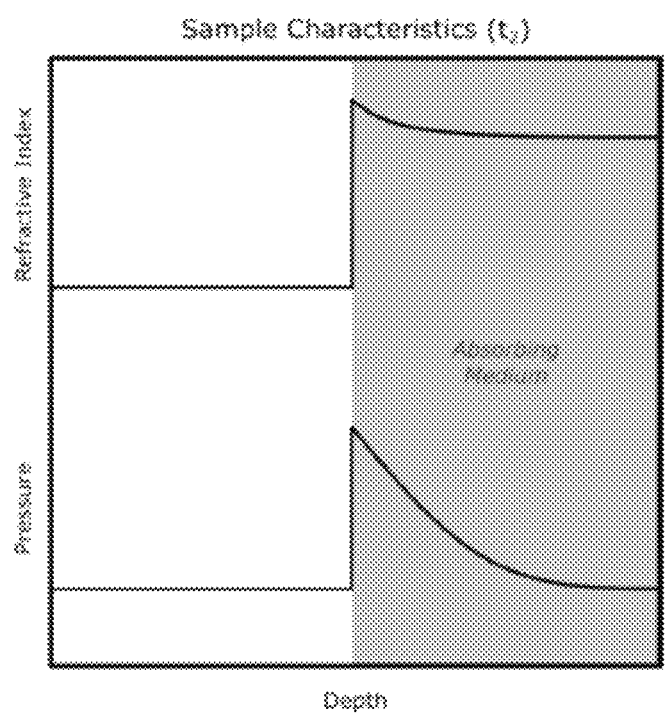

FIG. 29 describes the mechanism through which PARS signals are generated and captured. FIG. 29 (*a*) shows a representative example of a PARS signal, excitation laser activation signal, and an interrogation laser activation signal across time during an example imaging session. In this case, the example PARS system is implemented with a CW interrogation laser, and a pulsed excitation laser. In FIG. 29(*a*) several time points are highlighted to help demonstrate the functionality of this PARS system. Here, the interrogation beam is active across all time points. At time point $t_1$ the excitation laser is inactive, and the measured PARS signal remains at rest with a constant (DC) offset. At time point $t_2$ the excitation laser has just delivered a short pulse and as the sample has now been excited a measurable AC waveform can be seen in the photothermal and photoacoustic signal. At time point $t_3$ the PARS signal has now returned to rest as enough time has passed since the excitation pulse. FIG. 29 (*b*) demonstrates pressure change and refractive index change across a boundary layer transition in depth, moving from a non-absorbing medium to an absorbing medium. This represents the sample characteristics at time point $t_1$ and $t_3$ of FIG. 29 (*a*). In this example there is a constant increase in refractive index once entering the absorbing medium, and as the sample is at rest there is no pressure change when entering the absorbing medium. FIG. 29 (*c*) demonstrates the sample pressure gradient and refractive index across a boundary layer transition in depth, moving from a non-absorbing medium to an absorbing medium. This represents the sample characteristics at time point $t_2$ of FIG. 29 (*a*). At this timepoint, the sample has just been delivered a pulse from the excitation laser which causes a large pressure gradient in depth in the absorbing medium. This large increase in pressure causes a change in the refractive index of the sample, which causes a measurable change in the returning light intensity of the interrogation laser. This can be seen demonstrated as an AC waveform in the PARS signal in FIG. 29 (*a*).

FIG. 30 describes the signal processing pathway for an example PARS system. The PARS optical detector signal (3001) may be captured with devices including, but not limited to: photodiodes, avalanche photodiodes, phototubes, photomultipliers, CMOS cameras, CCD cameras (including EM-CCD, intensified-CCDs, back-thinned and cooled CCDs), spectrometers, etc. This signal may then undergo analog signal processing (3002), which may include, but is not limited to low-pass filtration, high-pass filtration, amplification, attenuation, etc. Additionally, the signal may also be fed through an alternate path (3003) to highlight different signal characteristics. The processed or/and unprocessed PARS signal then undergoes signal digitization (3004). This digital signal then may undergo digital signal processing (3005), which may include, but is not limited to low-pass filtration, high-pass filtration, Hilbert transformation, Fourier transforms, PARS signal identification methods, extracting polarization, phase and frequency content, etc. From this fully processed signal, in some embodiments, key features can be extracted (3006) to produce a PARS image, which may include, but is not limited to techniques such as: absolute maximum projection, peak frequency, etc.

Figure 31B:
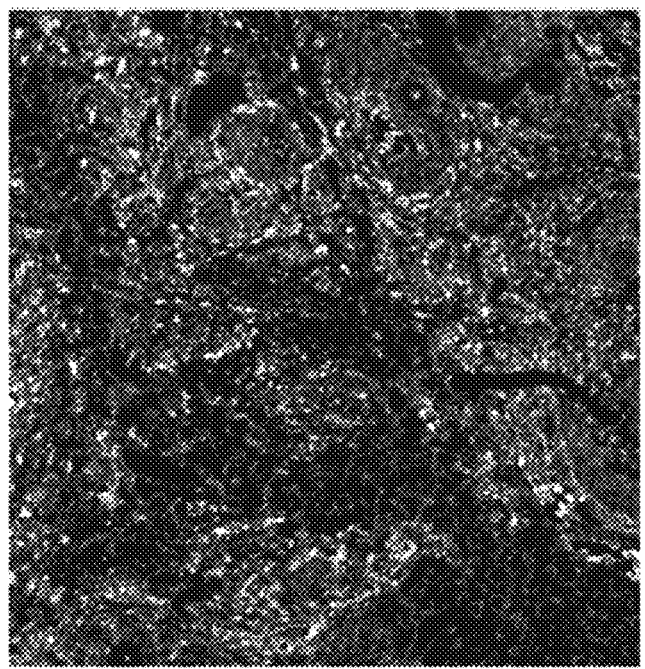
FIGS. 31a-b Shows example PARS images.
Figure 31A:
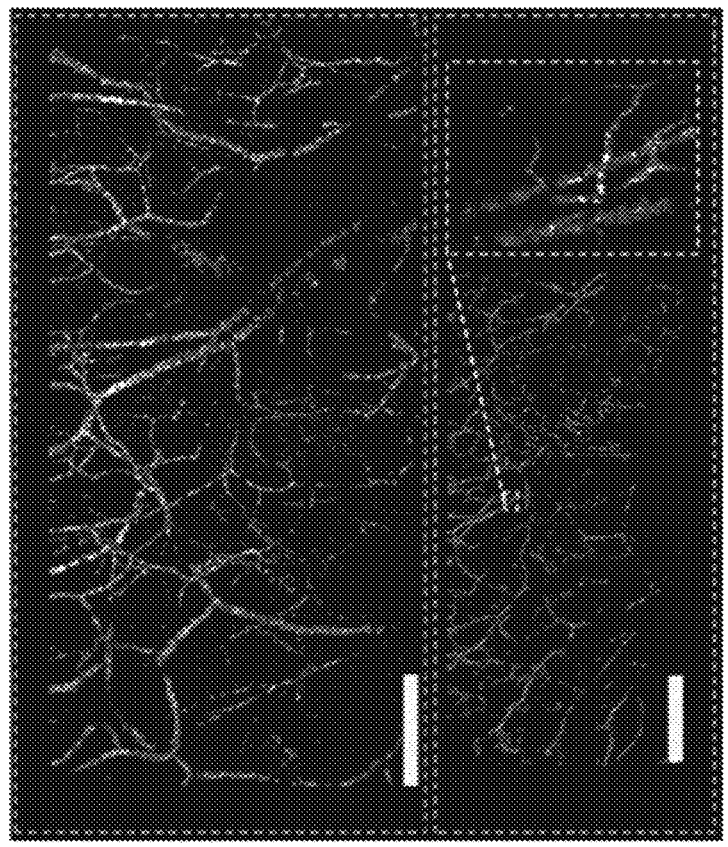

FIG. 31 depicts two PARS images which implemented different excitation wavelengths to target specific absorbers. FIG. 31 (*a*) depicts an in vivo PARS image of vasculature in a mouse ear leveraging green light (532 nm) absorption contrast to target hemoglobin. FIG. 31 (*b*) depicts an ex vivo PARS image of human tissue leveraging ultraviolet light (266 nm) absorption contrast to target DNA.

Figure 32:
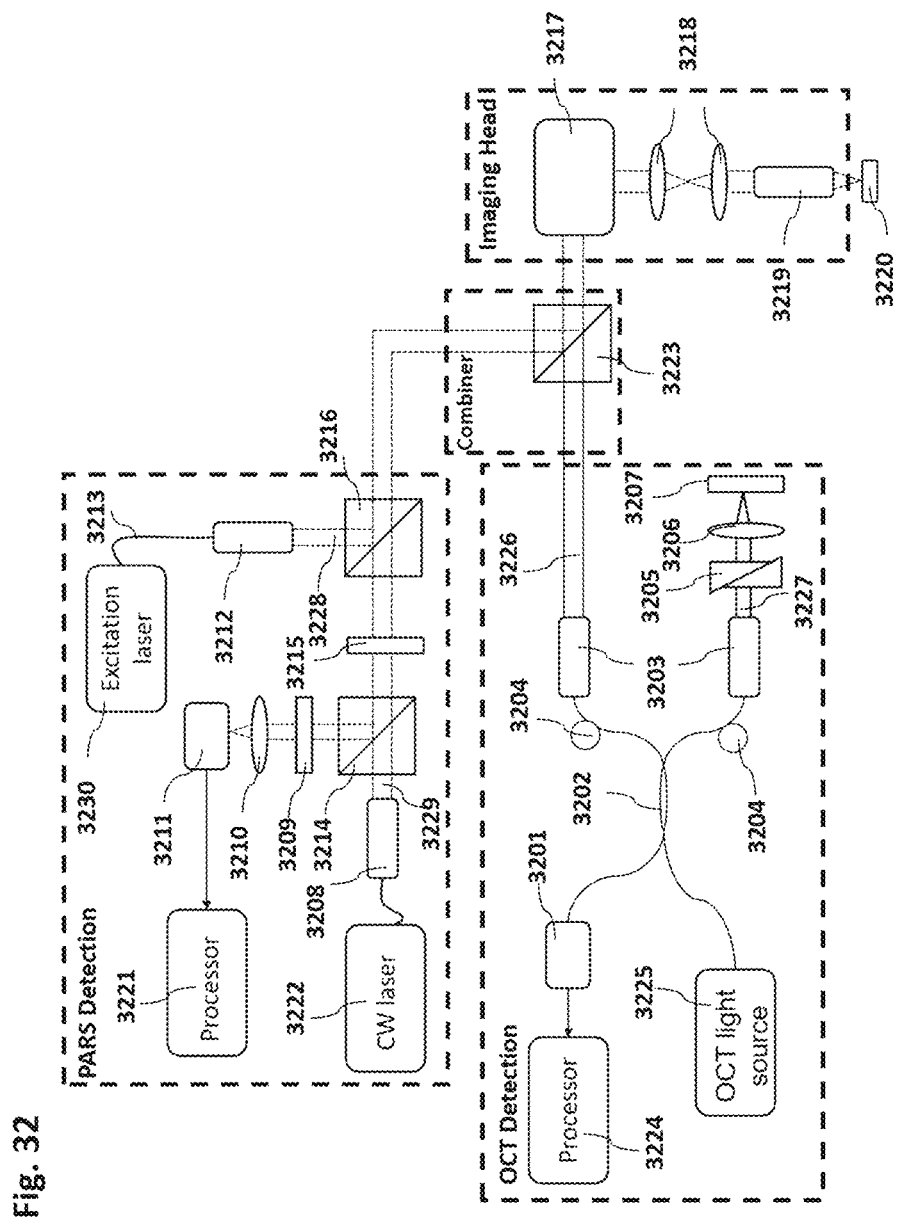
FIG. 32 Shows an example system layout for a PARS-OCT.

FIG. 32 highlights one implementation of PARS-OCT. In this example the beam coming from an interrogation source (3222) passes through an appropriate collimator (3208) and is directed into a polarized beam-splitter (3214), quarter-wave-plate (3215), and is directed toward an appropriate dichroic mirror (3216); together with the excitation beam (3228) coming from the pulsed-laser (3230) and appropriate collimator (3212) and toward the sample path. In the OCT subsystem, the beam coming from the broadband light source (3225) is directed into a free-space/fiber-coupler beam splitter (3202) with an appropriate split ratio, and is divided into a reference beam (3227) and a sample beam (3226). These systems may require beams which can provide a wide spectrum of illumination such as broadband CW sources, or swept sources. Polarization controllers (3204) might be used to maximize interference efficiency. The reference beam is collimated by an appropriate collimator (3203) and goes through a dispersion compensation unit (3205) and using an appropriate lens (3206) focuses on the reference mirror (3207). The sample beam is directed toward an appropriate dichroic mirror (3223) and is combined with the PARS excitation (3228) and interrogation (3229) beams. All the beams are then directed toward the sample (3220). In this case galvo-scanner mirrors (3217) are used along with a pair of telecentric lenses (3218) and objective lens (3219). The returning beams are directed toward the dichroic mirror (3223) and separated into OCT and PARS interrogation beams. The OCT sample beam interferes with the reference beam, the mixing is detected by the appropriate detector (3201), and the signal is directed toward the corresponding processor (3224). The PARS interrogation beam is directed toward an appropriate filter (3209) to filter out the interrogation beam spectral range, and using an appropriate lens (3210) is focused onto the detector (3211), the signal is post processed in the corresponding processor (3221).

Figure 33:
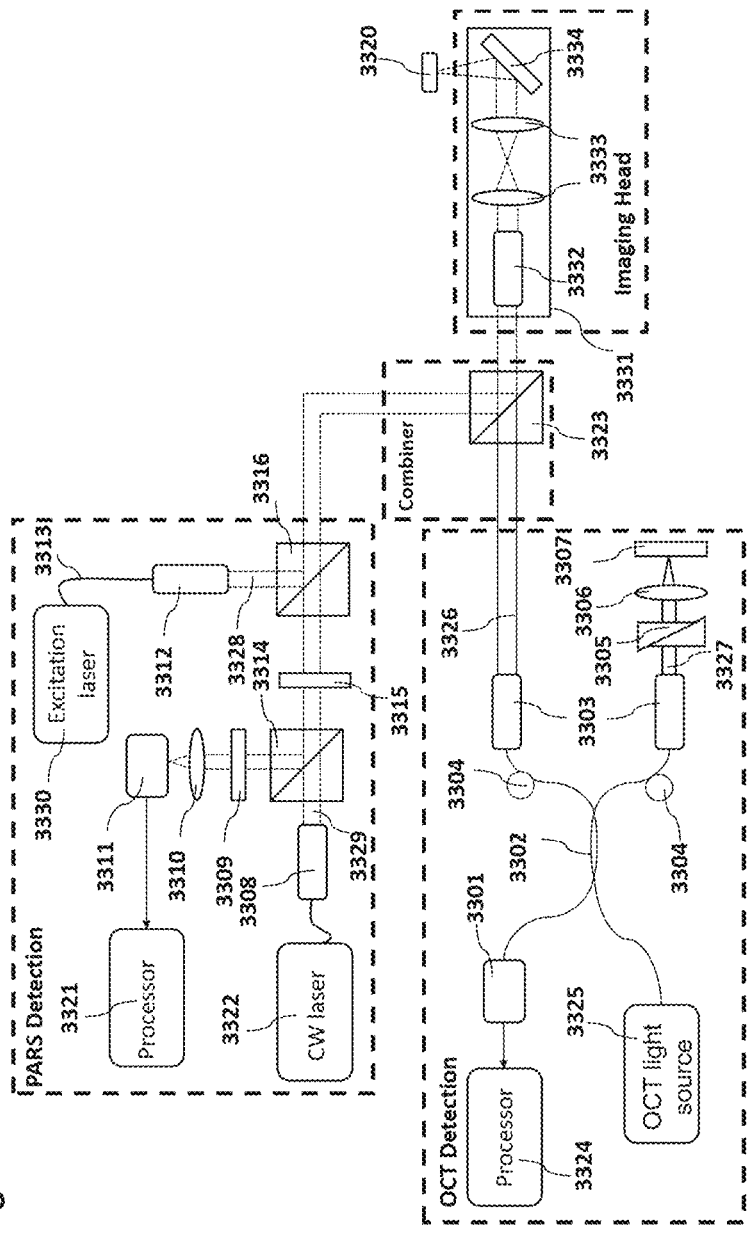
FIG. 33 Shows another example system layout for an EPARS-OCT.

FIG. 33 highlights an implementation of EPARS-OCT. This implementation is similar to that from FIG. 32 except the combination of the beams are delivered to the sample through an endoscope (3331), which comprises but is not limited to a collimator (3332) along with appropriate imaging optics (3333 & 3334).

Figure 34:
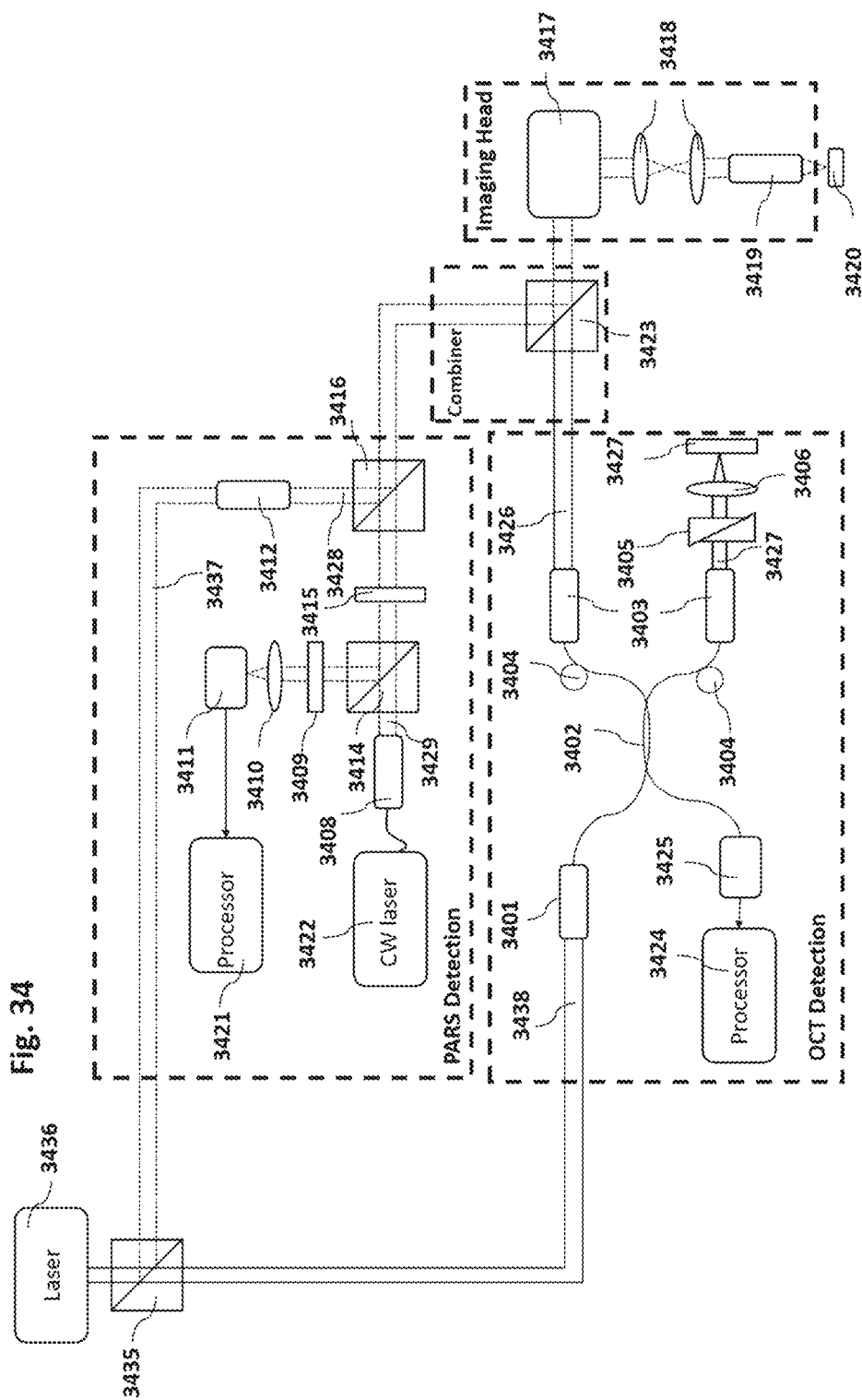
FIG. 34 Shows yet another example system layout for a PARS-OCT.

FIG. 34 highlights another novel implementation of PARS-OCT where the PARS excitation and OCT light source is shared (3436) where the light source may be but is not limited to a nanosecond-pulsed supercontinuum laser, directed toward the appropriate dichroic mirror (3435) to separate PARS excitation (3437) and OCT illumination (3438) beams. If the light source (3436) is shared in this way between multiple paths it may require broadband output which can be filtered down into required subsections (PARS, OCT, etc.) or tunable such that it may field each requirement individually. Outside of the broadband nature, it may not require any special properties beyond those particular to the individual beam sources of other system. Such a device layout may provide significant advantages over architectures which use individual sources for each pathway. Some of these advantages may include overall device cost, size, ease of maintenance (including items like alignment), etc. For example, system alignment may be made easier since multiple pathways may share the same wavelength reducing undesired chromatic effects. In this example the rest of the system embodiment is similar to that from FIG. 32.

Figure 35:
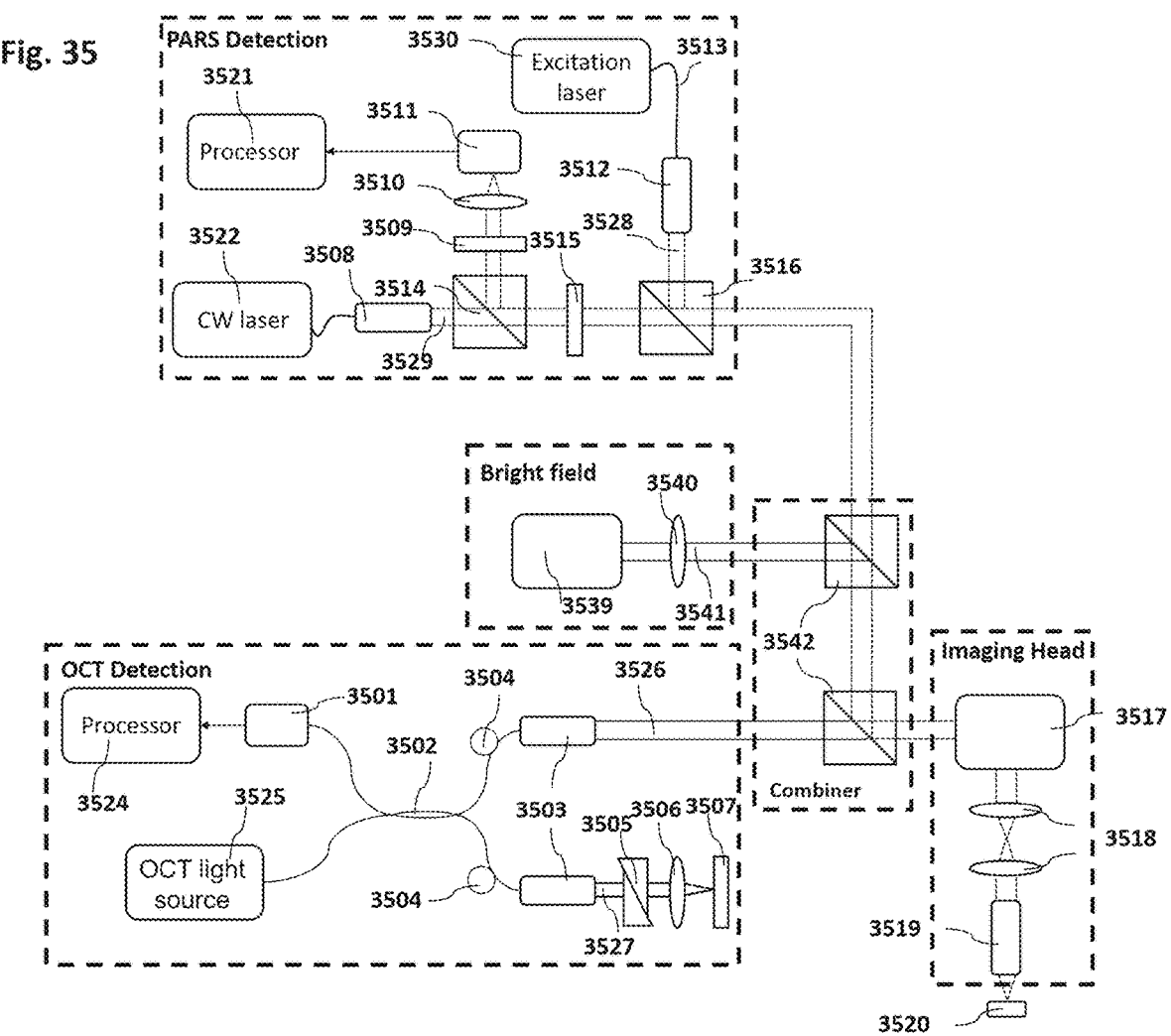
FIG. 35 Shows an example system layout for multimodal PARS-OCT.

FIG. 35 highlights yet another implementation of a multi-modal PARS-OCT system. This implementation is similar to that from FIG. 32. However, rather than a single combiner, two beam combiners (3542) are used to combine the PARS beams, OCT beam and a bright-field microscope beam (3541). Here the bright-field detection is implemented as a tube lens (3540) and a camera (3539). Additional modalities may be added in this manner such as fluorescence microscope, scanning laser ophthalmoscope, ultrasound imaging, etc.

Figure 36:
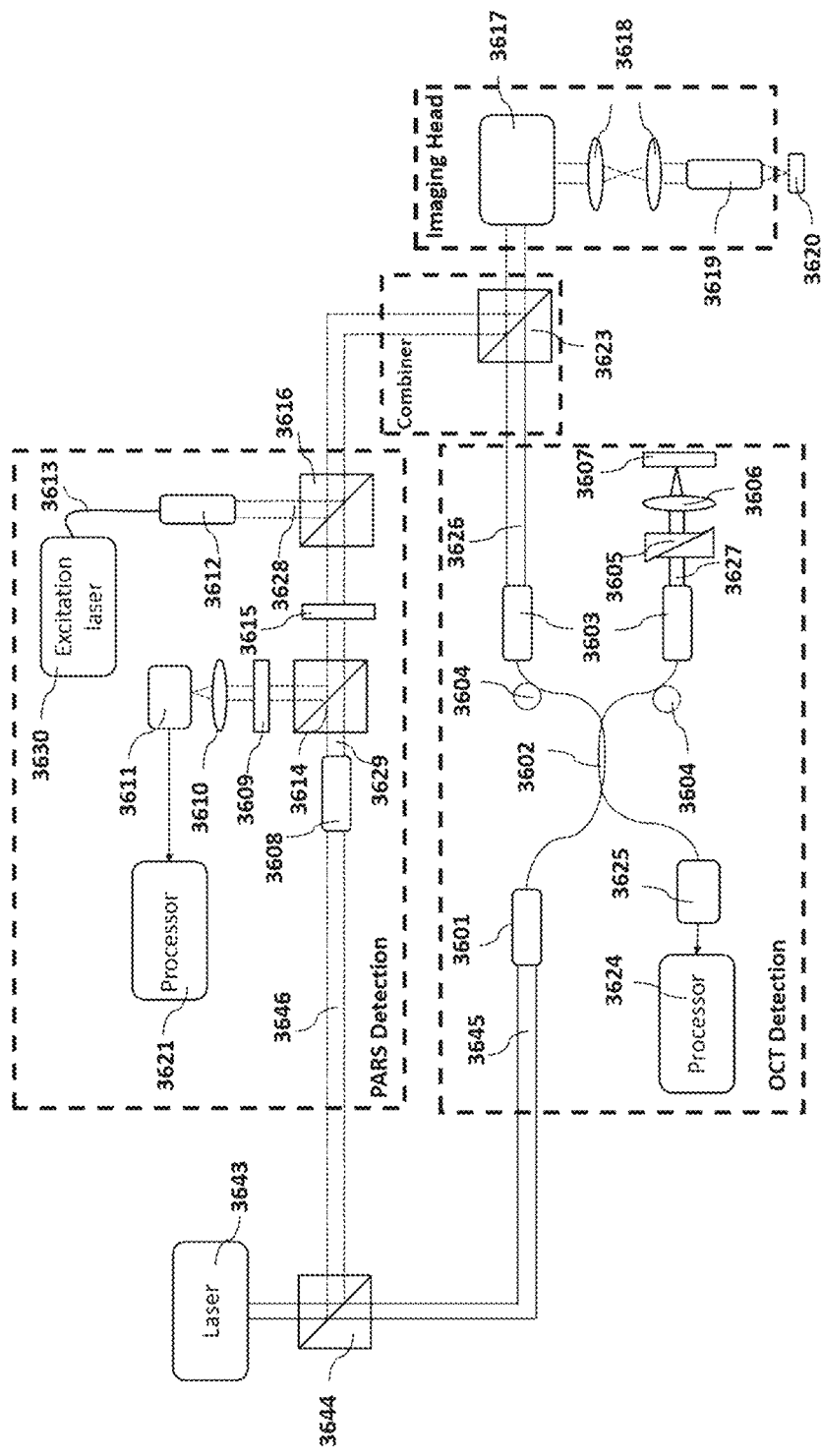
FIG. 36 Shows yet another example system layout for a PARS-OCT.

FIG. 36 highlights another novel implementation of PARS-OCT where the PARS interrogation and OCT light source is shared (3643) where the light source may be but is not limited to a continuous wave laser, directed toward the appropriate beam combiner (3644) to separate PARS interrogation (3646) and OCT illumination (3645) beams. Such a device layout may provide significant advantages over architectures which use individual sources for each pathway. Some of these advantages may include overall device cost, size, ease of maintenance (including items like alignment), etc. For example, system alignment may be made easier since multiple pathways may share the same wavelength reducing undesired chromatic effects. In this example the rest of the system embodiment is similar to that from FIG. 32.

Likewise, similar combinations of system can be envisioned which use a single (i.e., exactly and only one) laser source for all three of the PARS excitation, PARS interrogation, and OCT beams.

Figure 37:
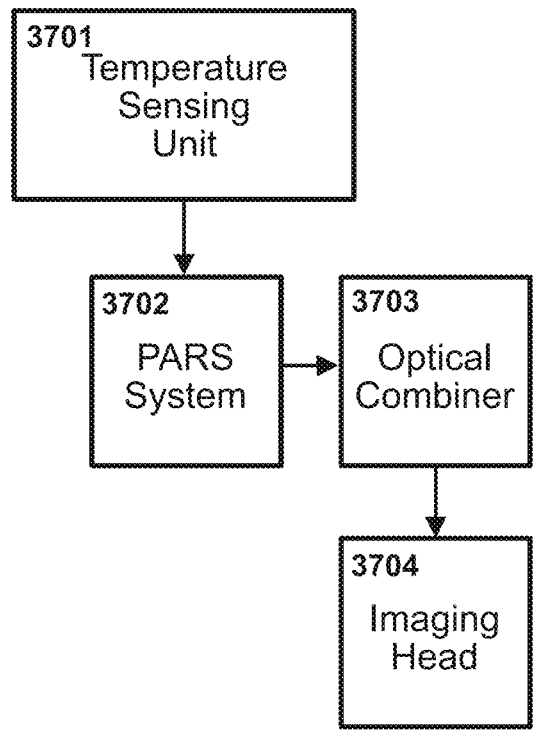
FIG. 37 Shows an overview of a TS-PARS.

FIG. 37 highlights a block diagram for a TS-PARS system. This may be implemented as a conventional PARS system (3702) that is combined (3703) and is directed onto the sample through an imaging head (3704). At least one notable difference here, involves the addition of a temperature sensing unit (3701) which can decode the information contained within the PARS signal and interpret it to produce an absolute, or relative temperature measurement of the sample. Individual PARS measurements may be compared against known signals for a given sample at a given temperature. Likewise, multiple PARS measurements may be compared against each other for a given sample to produce a relative change in temperature between these multiple measurements. The sensing unit and/or controller then converts these relative changes in PARS signals into relative or absolute temperature measurements.

Figure 38:
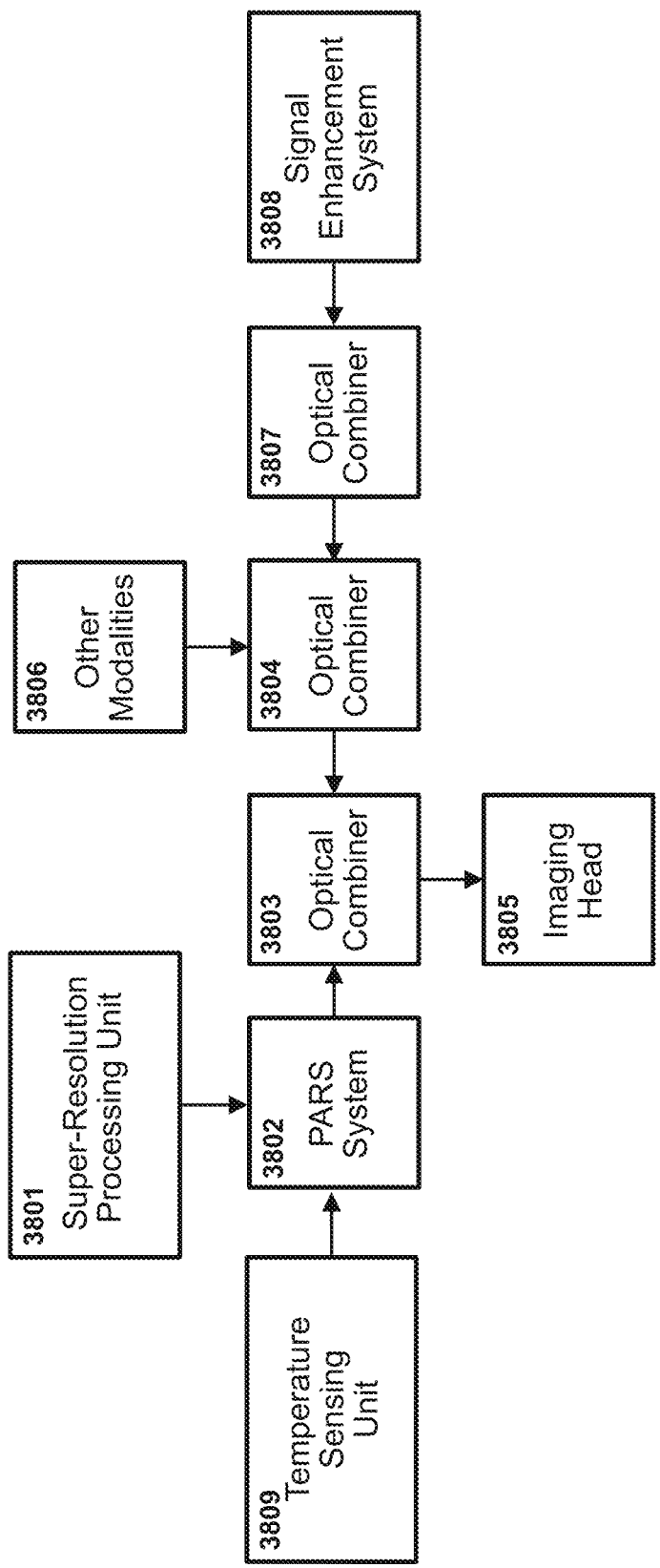
FIG. 38 Shows an example combination between a TE-PARS, TS-PARS, SR-PARS and other modalities.

FIG. 38 highlights a block diagram for a combination between multiple of the described systems, in this case between a TS-PARS (3809), SR-PARS (3801), TE-PARS (3808) and a collection of other modalities (3806). These individual systems are combined (3802, 3803, 3804, 3807) and directed into a singular imaging head (3805) before being directed onto the sample. Other combinations of systems described herein may be similarly combined.

Figure 39:
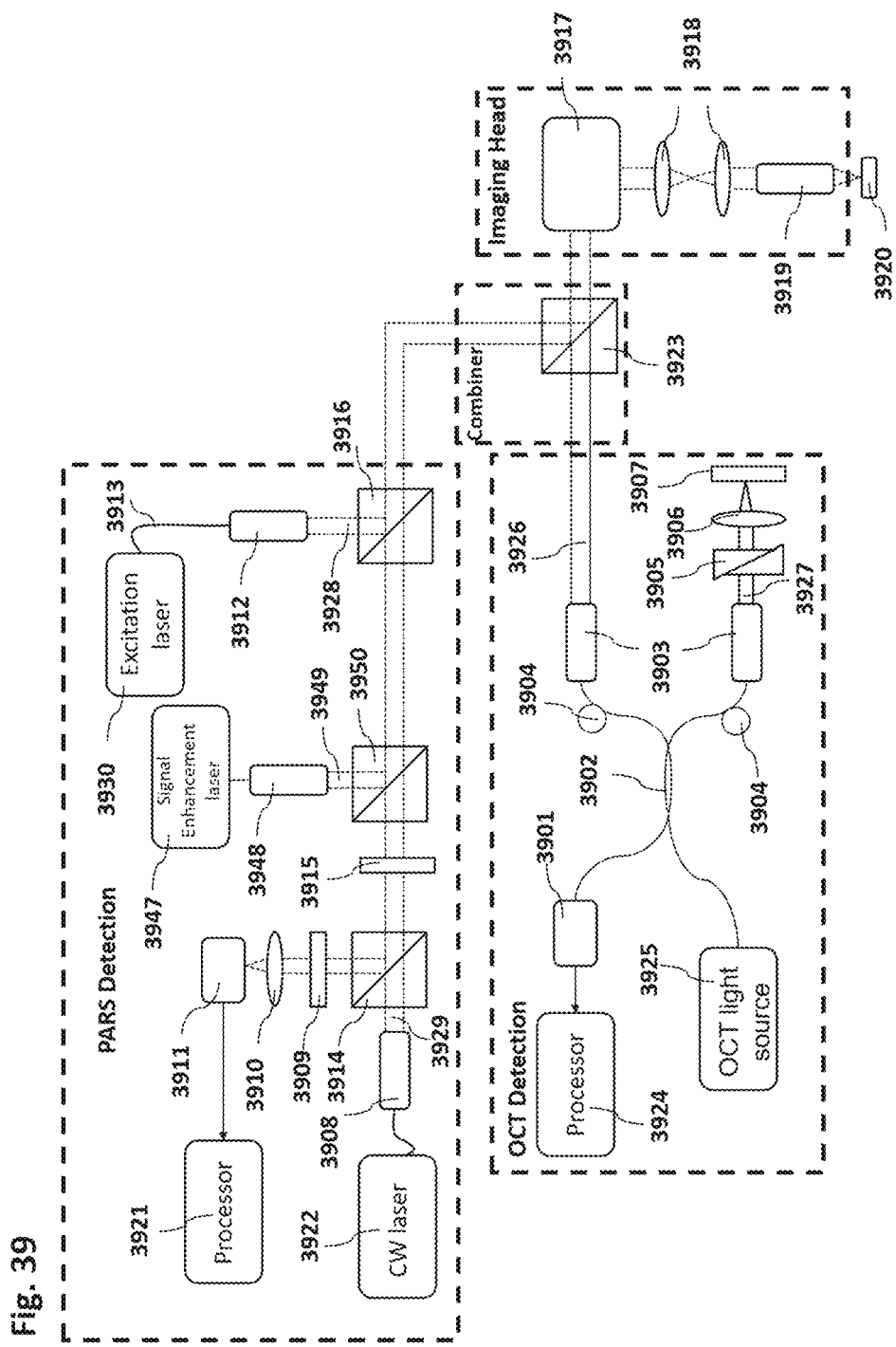
FIG. 39 Shows a PARS-OCT which features a thermal enhancement source.

FIG. 39 highlights yet another PARS-OCT implementation which features a thermal enhancement source. A signal enhancement laser (3947) is used to enhance the PARS signals using a signal enhancement beam (3949). The enhancement beam coming from the laser passes through an appropriate collimator (3948), and is combined with the PARS interrogation beam (3929) using an appropriate beam combiner (3950). In this example the rest of the system embodiment is similar to that from FIG. 32.

Figure 40:
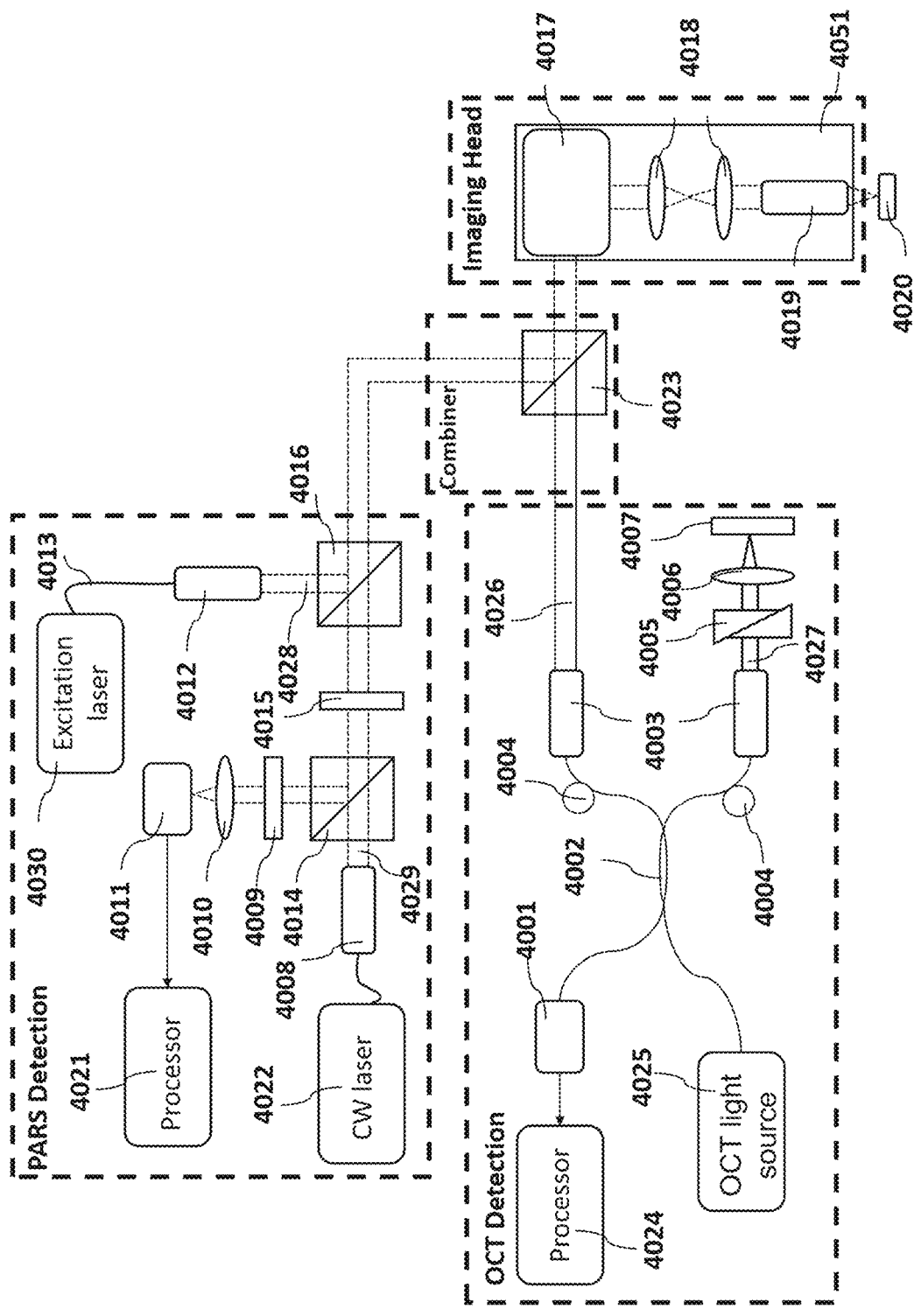
FIG. 40 Shows a PARS system wherein the optical subsystems are scanned mechanically about the sample.

FIG. 40 highlights another PARS-OCT implementation wherein the optical subsystems are scanned mechanically about the sample. In this example, the imaging head is mounted on a mechanical scan stage (4051) unit which enables lateral, axial and rotational scans. In this example the rest of the system embodiment is similar to that from FIG. 32.

Figure 41:
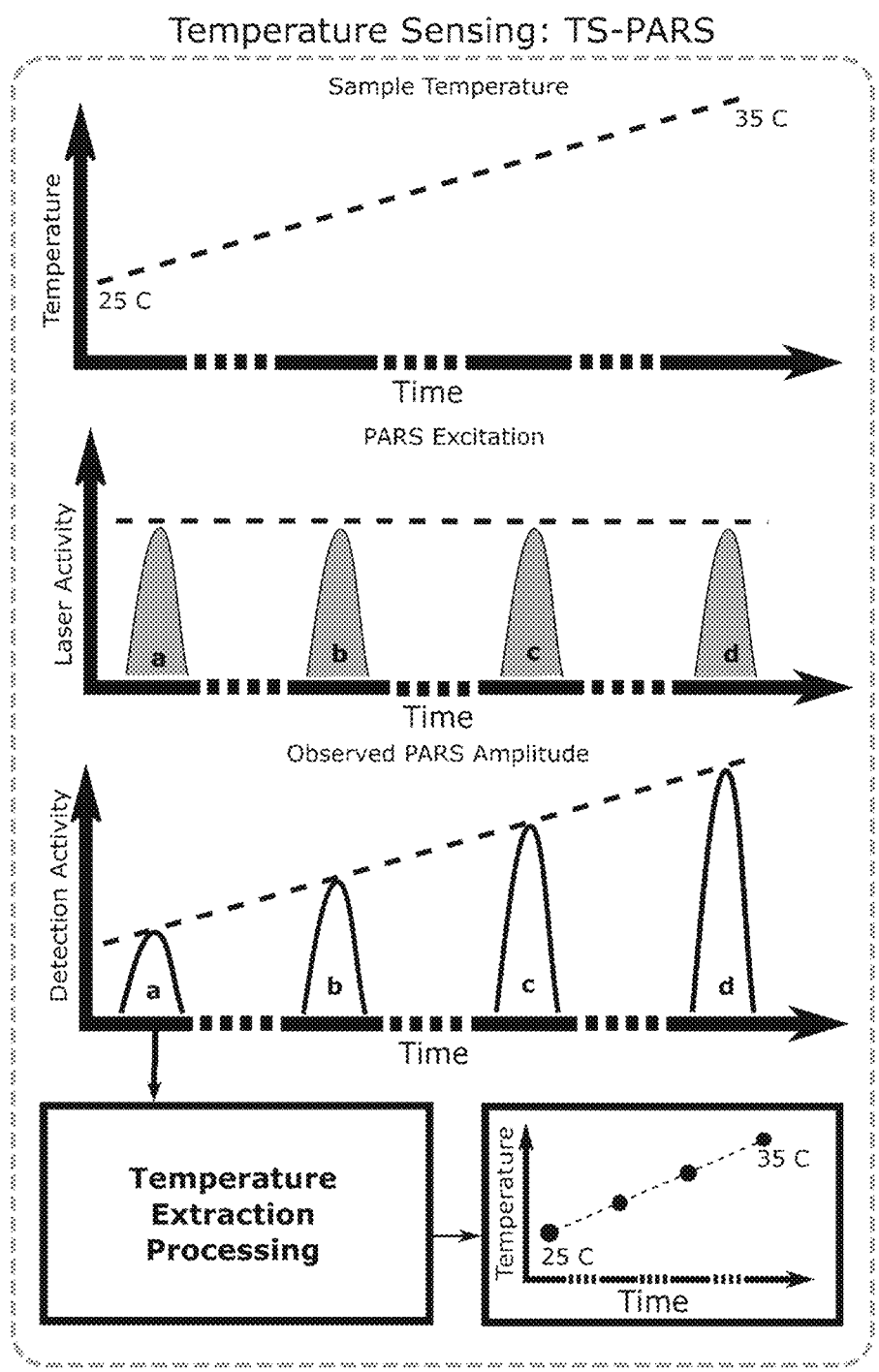
FIG. 41 Shows an example of the TS-PARS detection process.

FIG. 41 provides a high-level description of the temperature-sensing processing which may be present in TS-PARS. As sample temperature changes (in this case from 25° to 35°) the efficiency of photoacoustic pressure generation also changes. In this case, for a constant excitation energy level (pulses a, b, c, d), the output signal increases with rise in temperature. These temperature modulations can then be recorded and fit to expected temperature-dependent models to extract relative or absolute changes in temperature within the sample.

Figure 42:
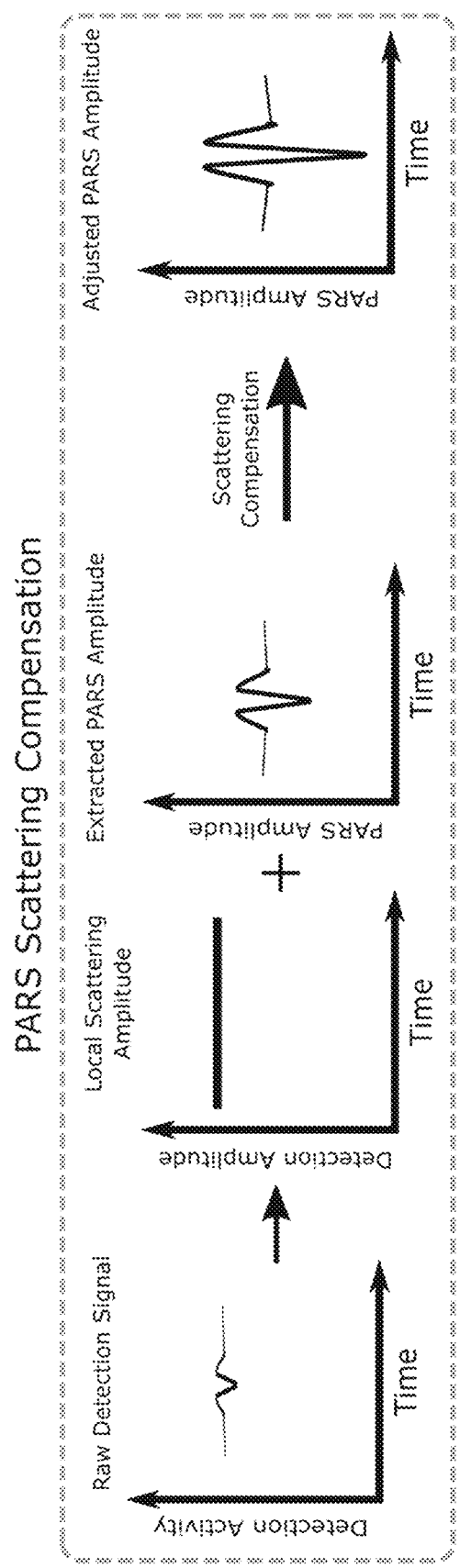
FIG. 42 Shows a scattering subtraction processing pathway.

FIG. 42 shows a high-level overview of the scattering compensation method. The PARS signal has a strong dependence on the unperturbed back-scattered light and therefore local scattering efficiency of a sample. To decouple the PARS signal amplitude from the local scattering efficiency the back-scatter amplitude is extracted and removed from the PARS signals using a unique controller for the task, which may be the same controller as any of the aforementioned or later mentioned controllers, or a different controller. The controller subtracts collected scattering contrast from the PARS signal which serves to reduce the background noise from randomly scattered photons and amplifies the signal to noise ratio.

Figure 43:
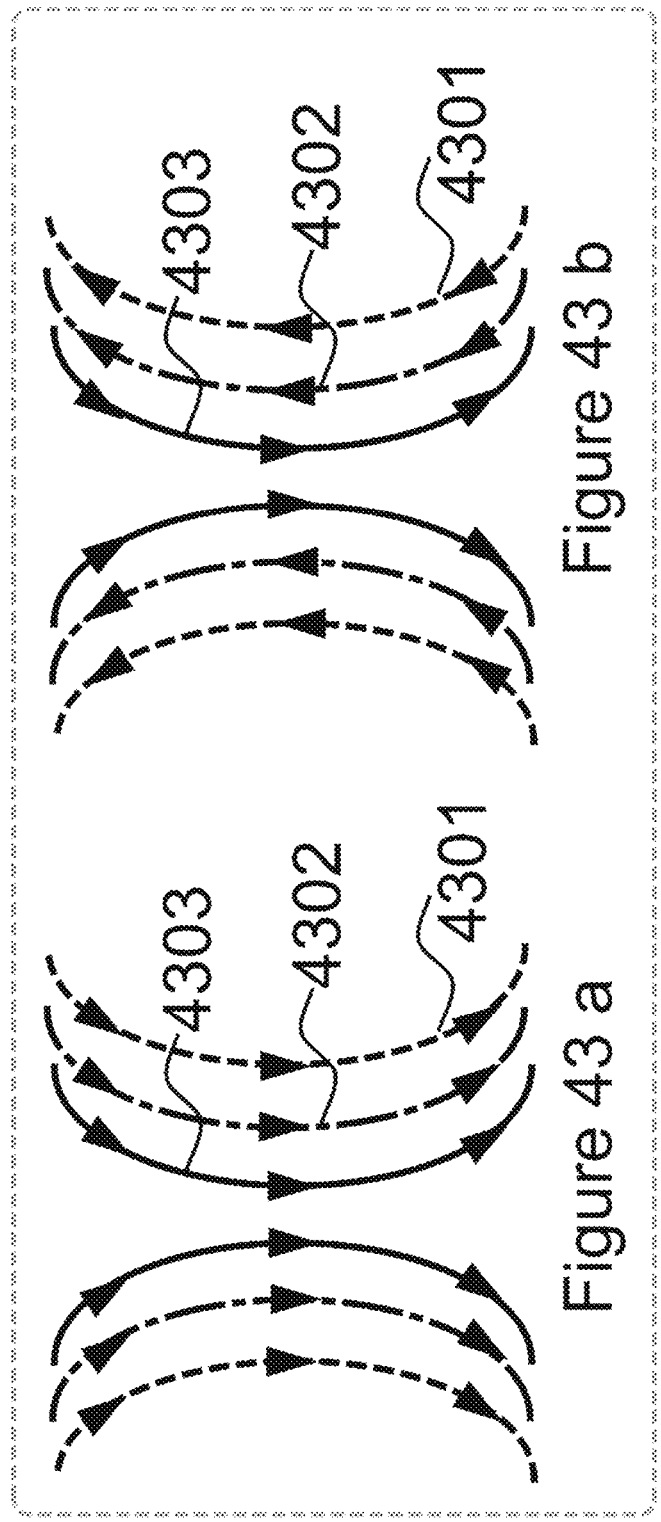
FIGS. 43a-b Show examples of various constituent optical beams demonstrating that some pathways may be implemented in transmission mode.

In any of the TE-PARS, TS-PARS, SE-PARS, SD-PARS, SR-PARS, PARS or OCT-PARS modalities one or more of the beam pathways may be oriented in transmission mode meaning that beam collection optics are placed on the opposite side of the sample to those optics which are directing light at the sample. FIG. 43 exemplifies this case, in the example of a TE-PARS system, here the beams (4301), (4302), (4303) each represent any one of the TE-PARS excitation, detection and signal enhancement beams. In each case, one or more of these beams may be oriented in the same or opposite direction as the other beams. Moreover, these directionalities are not intended to be limiting and may be applied to any of the exemplified beam overlap conditions shown in FIG. 21, or any other logical beam positioning. Some potential advantages of this may result when thin samples (<1 mm) are imaged as forward scattering tends to be more significant as compared to back scattering. As well such implementations may help support the use of multiple modalities at the same time by not requiring all modalities to arrive at the sample via the same objective lens, greatly improving multiplexing capabilities.

Figure 44:
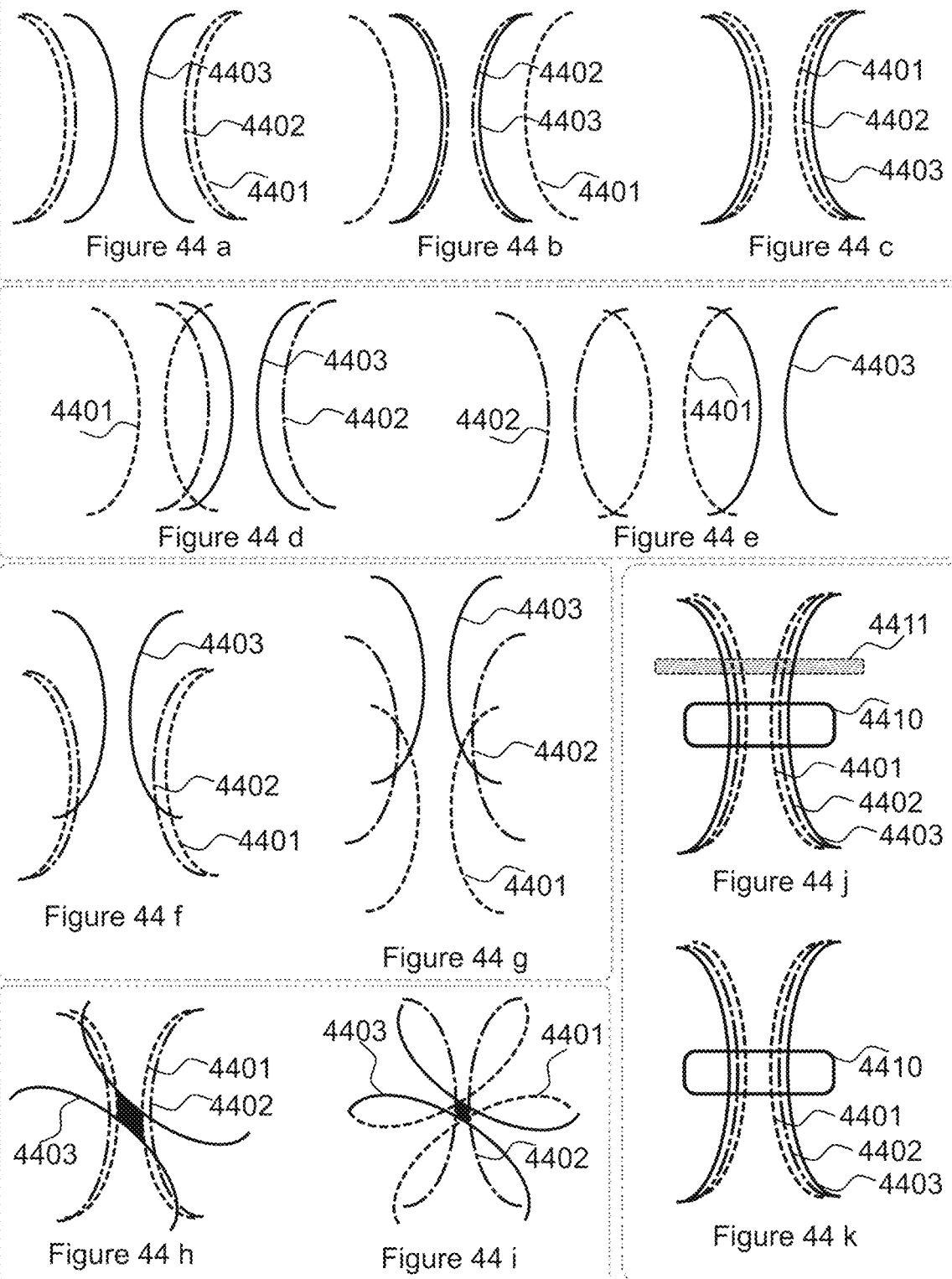
FIGS. 44a-k Show different spot arrangements for a PARS-OCT system.

FIG. 44 shows an example of several local spot positioning conditions for a PARS-OCT. Each of the respective beams (4401), (4402), (4403) may represent any the excitation, detection, signal enhancement or OCT beams. FIG. 44a highlights an orientation where one of the PARS or OCT excitation, detection, and signal enhancement beams forms a smaller focal spot as compared to the other two beams. Likewise, FIG. 44b highlights an alternate case wherein two of the excitation, detection, and signal enhancement beams form smaller focal spots than the third beam. FIG. 44b exemplifies a third case where in each of the PARS or OCT excitation, detection and signal enhancement beams form nearly equivalent focal spots. FIGS. 44d and 44e, show focal conditions where in the spots of the constituent beams do not perfectly overlap at the focal spot but are displaced in the lateral direction. In the first case (FIG. 44d) a singular beam is displaced while the other two remain overlapped, in the second case (FIG. 44e) all three beams are displaced relative to each other. Similar to FIGS. 44d and 44e, FIGS. 44f and 44g, show focal conditions where the spots of the constituent beams do not overlap at the focal spot but are displaced in the axial direction. In the first case (FIG. 44f) a singular beam is displaced while the other two remain overlapped, in the second case (FIG. 44g) all three beams are displaced relative to each other. These displacements may be any reasonable value depending on the requirements of the imaging session. FIG. 44h and FIG. 44i highlight conditions where the central beam axes form an angle between themselves and between the sample, where this angle may commonly range between 5 and 90 degrees with the sample surface. FIG. 44h highlights the case where two of the beams remain co-aligned while the angle of the third beam is modified. FIG. 44i shows the case where each of the beams holds an independent angle relative to the others. Finally, FIG. 44j and FIG. 44k show two different cases for scanning a sample (4410). In FIG. 44k the sample is placed directly within the path of the beams, alternatively in FIG. 44j there is some scattering media or optical window (4411) located in the beam path prior to the sample, an example of a common media within the beam path before the sample would be a glass slide or cover slip to contain the sample. This diagram is not meant to be limiting and has obvious extensions where the system comprises more than three beams.

Figure 45:
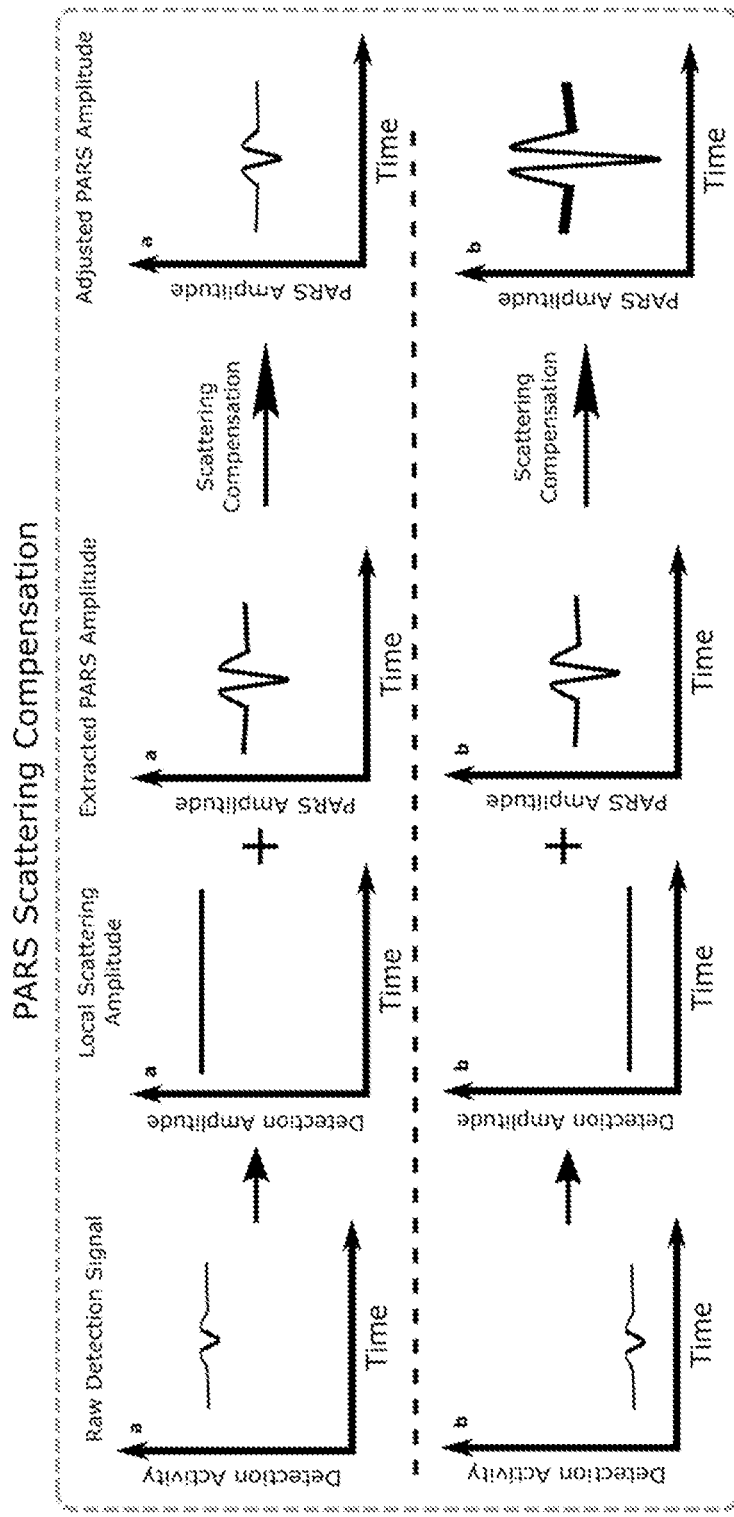
FIG. 45 Shows another example of a scattering subtraction processing pathway.

FIG. 45 shows another high-level example of a PARS signal augmentation. As the PARS signal has a strong dependence on the backscattered light and therefore local scattering properties of a sample, this information can information can be leveraged to reproduce more accurate visualizations of optical absorption contrast by removing remaining scattering contrast inherent in the standard PARS acquisition. In some applications, the scattering content from detection, signal enhancement or excitation lasers may be collected separately. These signals may get subtracted or added to the PARS signals and may analyzed separately based on their amplitude, phase, polarization, and frequency content to provide additional information regarding the sample. In the example shown, in order to decouple the PARS signal amplitude from the local scattering efficiency the local backscattering amplitude is extracted independently of the PARS signal. In this example, both PARS signals appear to have the same amplitude though there is significantly less backscattering in the "b" instance. To reduce the local scattering effects, the PARS signals are normalized relative to their measured local scattering amplitude. As exemplified here this serves to amplify signals with low scattering amplitude and reduce signals with strong scattering amplitude. Optical properties of any of the detection, signal enhancement, or excitation may be collected including the polarization, frequency, phase content, fluorescence etc. This information may be mixed, subtracted, added or otherwise augmented with the PARS signal to achieve the desired signal modification result.

It will be apparent that other examples may be designed with different fiber-based or free-space components to achieve similar results. Other alternatives may include various coherence length sources, use of balanced photodetectors, interrogation-beam modulation, incorporation of optical amplifiers in the return signal path, etc.

During in vivo imaging experiments, no agent or ultrasound coupling medium are required. However, the target can be prepared with water or any liquid such as oil before non-contact imaging session. As well, in some instances an intermediate window such as a cover slip or glass window may be placed between the imaging system and the sample.

All optical sources including but not limited to PARS excitations, PARS detections, PARS signal enhancements, and OCT sources may be implemented as continuous beams, modulated continuous beams, or short pulsed lasers in which pulse widths may range from attoseconds to milliseconds. These may be set to any wavelength suitable for taking advantage of optical (or other electromagnetic) properties of the sample, such as scattering and absorption. Wavelengths may also be selected to purposefully enhance or suppress detection or excitation photons from different absorbers. Wavelengths may range from nanometer to micron scales. Continuous-wave beam powers may be set to any suitable power range such as from attowatts to watts. Pulsed sources may use pulse energies appropriate for the specific sample under test such as within the range from attojoules to joules. Various coherence lengths may be implemented to take advantage of interferometric effects. These coherence lengths may range from nanometers to kilometers. As well, pulsed sources may use any repetition rate deemed appropriate for the sample under test such as from continuous-wave to the gigahertz regime. The sources may be tunable, monochromatic or polychromatic.

The SD-PARS may use a detection wavelength purposefully selected such that it suppresses generated PARS signals from a particular region. For example, if a desired target is positioned next to a large blood vessel which might otherwise overwhelm the signal from the desired target, the detection wavelength may be selected as to suppress signal from the blood vessel by populating absorption energy levels prior to detection.

The TE-PARS, TS-PARS, SR-PARS, SE-PARS, SD-PARS, PARS-OCT or EPARS-OCT subsystems may use any interferometry designs such as a common path interferometer (using specially designed interferometer objective lenses), Michelson interferometer, Fizeau interferometer, Ramsey interferometer, Fabry-Perot interferometer, Mach-Zehnder interferometer, and optical-quadrature detection. Interferometers may be free-space or fiber-based or some combination. The basic principle is that phase and amplitude oscillations in the probing receiver beam can be detected using interferometry and detected at AC, RF or ultrasonic frequencies using various detectors.

The TE-PARS, TS-PARS, SR-PARS, SE-PARS or SD-PARS subsystems may use and implement a non-interferometry detection design to detect amplitude modulation within the signal. The non-interferometry detection system may be free-space or fiber-based or some combination therein.

The TE-PARS, TS-PARS, SD-PARS, SR-PARS, SE-PARS, PARS-OCT or EPARS-OCT subsystems may use a variety of optical fibers such as photonic crystal fibers, image guide fibers, double-clad fibers etc.

The PARS subsystems may be implemented as a conventional photoacoustic remote sensing (PARS), non-interferometric photoacoustic remote sensing (NI-PARS), camera-based photoacoustic remote sensing (C-PARS), coherence-gated photoacoustic remote sensing (CG-PARS), single-source photoacoustic remote sensing (SS-PARS), or extensions thereof.

The OCT subsystem may be implemented as spectral-domain optical coherence tomography (SD-OCT), swept-source optical coherence tomography (SS-OCT), time-domain optical coherence tomography (TD-OCT), full-field optical coherence tomography (FF-OCT), line-field optical coherence tomography (LF-OCT), polarization-sensitive optical coherence tomography (PS-OCT), Gabor-domain optical coherence tomography (GD-OCT), etc.

In the PARS-OCT and EPARS-OCT, the PARS and OCT subsystems may operate individually as a single imaging system and acquire images independently as a standalone imaging device.

In one example, all beams may be combined and scanned. In this way, PARS excitations may be sensed in the same area as they are generated and where they are the largest. OCT detection may also be performed in the same location as the PARS to aid in registration. Other arrangements may also be used, including keeping one or more of the beams fixed while scanning the others or vice versa.

Optical scanning may be performed by galvanometer mirrors, MEMS mirrors, polygon scanners, stepper/DC motors, etc.

Mechanical scanning of the sample may be performed by stepper stages, DC motor stages, linear drive stages, piezo drive stages, piezo stages, etc.

Both the optical scanning and mechanical scanning approaches may be leveraged to produce one-dimensional, two-dimensional, or three-dimensional scans about the sample. Adaptive optics such as TAG lenses and deformable mirrors may be used to perform axial scanning within the sample.

Both optical scanning and mechanical scanning may be combined to form a hybrid scanner. This hybrid scanner may employ one-axis or two-axis optical scanning to capture large areas or strips in a short amount of time. The mirrors can potentially be controlled using custom control hardware to have customized scan patterns to increase scanning efficiency in terms of speed and quality. For example, one optical axis can be used to scan rapidly and simultaneously one mechanical axis can be used to move the sample. This may render a ramp-like scan pattern which can then be interpolation. Another example, using custom control hardware, would be to step the mechanical stage only when the fast-axis has finished moving yielding a cartesian-like grid which may not need any interpolation.

PARS may provide 3D imaging by optical or mechanical scanning of the beams or mechanical scanning of the samples or the imaging head or the combination of mechanical and optical scanning of the beams, optics and the samples. This may allow rapid structural and function en-face or 3D imaging.

One or multiple pinholes may be employed to reject out of focus light when optically or mechanically scanning the beams or mechanical scanning of the samples or the imaging head or the combination of mechanical and optical scanning of the beams, optics and samples. They may improve the signal to noise ratio of the resulting images.

Beam combiners may be implemented using dichroic mirrors, prisms, beamsplitters, polarizing beamsplitters, WDMs etc.

Beam paths may be focused on to the sample using different optical paths. Each of the single or multiple PARS excitation, detection, signal enhancement etc. paths and OCT paths may use an independent focusing element onto the sample, or all share a single path or any combination. Beam paths may return from the sample using unique optical paths which are different from those optical paths used to focus on to the sample. These unique optical paths may interact with the sample at normal incidence, or may interact at some angle where the central beam axis forms an angle with the sample surface ranging from 5 degrees to 90 degrees.

The beam configurations shown in FIGS. 19e and 19f may provide added spatial rejection of undesired randomly scattered photons, and detect only photons that have been modulated by the excitation or signal enhancement laser. Since the PARS imaging region is defined by the overlap of the excitation beam, detection beam and, in the case of TE-PARS, the thermal enhancement beam and backwards detection/reflected beam path, if these paths are all co-aligned, the interrogated region on the sample may be defined by a lateral radial distribution which is commonly shorter than the axial distribution. By angling the beams relative to each other, shown in FIGS. 19e and 19f the overlap may now be defined between the combination of two or more radial distributions. This allows for the lateral resolution of one of the beams to improve upon the axial performance provided by another beam. To maximize this effect, it may be most advantageous to have the beams evenly distributed in the azimuth and with around 45 degrees each to the sample surface. In some embodiments the altitude angles may vary amongst the beam paths.

For some applications such as in ophthalmic imaging, the imaging head may not implement any primary focusing element such as an objective lens to tightly focus the light onto the sample. Instead, the beams may be collimated, or loosely focused (as to create a spot size much larger than the optical diffraction limit) while being directed at the sample. For example, ophthalmic imaging devices made direct a collimated beam into the eye allowing the eye's lens to focus the beam on to the retina.

The imaging head may focus the beams into the sample at least to a depth of 50 nm. The imaging head may focus the beams into the sample at most to a depth of 10 mm. The added depth over previous PARS arises from the novel use of deeply-penetrating detection wavelengths as described above.

Light may be amplified by an optical amplifier prior to interacting with a sample or prior to detection.

Light may be collected by photodiodes, avalanche photodiodes, phototubes, photomultipliers, CMOS cameras, CCD cameras (including EM-CCD, intensified-CCDs, back-thinned and cooled CCDs), spectrometers, etc.

The detected signals may be amplified by an RF amplifier, lock-in amplifier, trans-impedance amplifier, or other amplifier configuration.

Modalities may be used for A-, B- or C-scan images for in vivo, ex vivo or phantom studies.

The TE-PARS, TS-PARS, SD-PARS, SR-PARS, SE-PARS, PARS-OCT or EPARS-OCT may take the form of any embodiment common to microscopic and biological imaging techniques. Some of these may include but are not limited to devices implemented as a table-top microscope, inverted microscope, handheld microscope, surgical microscope, endoscope, or ophthalmic devise, etc. These may be constructed based on principles known in the art.

The TE-PARS, TS-PARS, SD-PARS, SR-PARS, SE-PARS, PARS-OCT or EPARS-OCT may be optimized in order to take advantage of a multi-focus design for improving the depth-of-focus of 2D and 3D imaging. The chromatic aberration in the collimating and objective lens pair may be harnessed to refocus light from a fiber into the object so that each wavelength is focused at a slightly different depth location. These chromatic aberrations may be used to encode depth information into the recovered PARS signals which may be later recovered using wavelength specific analysis approaches. Using these wavelengths simultaneously may also be used to improve the depth of field and signal to noise ratio (SNR) of the PARS images. During imaging, depth scanning by wavelength tuning may be performed.

PARS methods may provide lateral or axial discrimination on the sample by spatially encoding detection regions, such as by using several pinholes, or by the spectral content of a broadband beam.

The TE-PARS, TS-PARS, SR-PARS, SE-PARS, SD-PARS, PARS-OCT or EPARS-OCT systems may be combined with other imaging modalities such as stimulated Raman microscopy, fluorescence microscopy, two-photon and confocal fluorescence microscopy, Coherent-Anti-Raman-Stokes microscopy, Raman microscopy, other photoacoustic and ultrasound systems, etc. This could permit imaging of the microcirculation, blood oxygenation parameter imaging, and imaging of other molecularly-specific targets simultaneously, a potentially important task that is difficult to implement with only fluorescence based microscopy methods. A multi-wavelength visible laser source may also be implemented to generate photoacoustic signals for functional or structural imaging.

Polarization analyzers may be used to decompose detected light into respective polarization states. The light detected in each polarization state may provide information about the sample.

Phase analyzers may be used to decompose detected light into phase components. This may provide information about the sample.

The PARS, TE-PARS, TS-PARS, SR-PARS, SE-PARS or SD-PARS systems may detect generated signals in the detection beam(s) returning from the sample. These perturbations may include but are not limited to changes in intensity, polarization, frequency, phase, absorption, nonlinear scattering, and nonlinear absorption and could be brought on by a variety of factors such as pressure, thermal effects, etc.

Analog-based signal extraction may be performed along electrical signal pathways. Some examples of such analog devices may include but are not limited to lock-in amplifiers, peak-detections circuits, etc.

The PARS subsystem may detect temporal information encoded in the back-reflected detection beam. This information may be used to discriminate chromophores, enhance contrast, improve signal extraction, etc. This temporal information may be extracted using analog and digital processing techniques. These may include but are not limited to the use of lock-in amplifiers, Fourier transforms, wavelet transforms, intelligent algorithm extraction to name a few. In one example, lock in detection may be leveraged to extract PARS signals which are similar to known expected signals for extraction of particular chromophores such as DNA, cytochromes, red blood cells, etc.

The OCT subsystems may detect generated PARS, thermal and pressure signals as perturbations to the back-reflected detection beam. These perturbations may include changes in intensity, polarization, phase, frequency, absorption, nonlinear scattering, and nonlinear absorption. The OCT subsystem may detect these perturbations by tracking changes over consecutive OCT scans. The OCT subsystems may also detect the vibration or surface oscillations generated by PARS systems.

The OCT and PARS subsystems may be used for detecting sample absorption properties through spectroscopic approaches. It can be used for detecting either PARS induced absorptions, OCT induced absorption or both.

The imaging head of the system may include close-loop or open-loop adaptive optic components including but not limited to wave-front sensors, deformable mirrors, TAG lenses, etc. for wave-front and aberration correction. Aberrations may include de-focus, astigmatism, coma, distortion, 3rd-order effects, etc.

The signal enhancement beam may also be used to suppress signals from undesired chromophores by purposely inducing a saturation effect such as photobleaching.

Various types of optics may be utilized to leverage their respective advantages. For example, axicons may be used as a primary objective to produce Bessel beams with a larger depth of focus as compared to that available by standard gaussian beam optics. Such optics may also be used in other locations within beam paths as deemed appropriate. Reflective optics may also take the place of their respective refractive elements. Such as the use of a reflective objective lens rather than a standard compound objective lens.

Optical pathways may include nonlinear optical elements for various related purposes such as wavelength generation and wavelength shifting.

Beam foci may overlap at the sample but may also be laterally and axially offset from each other when appropriate by a small amount.

The PARS, TE-PARS, TS-PARS, SR-PARS, SE-PARS or SD-PARS systems may be used as a spectrometer for sample analysis.

Other advantages that are inherent to the structure will be apparent to those skilled in the art. The embodiments described herein are illustrative and not intended to limit the scope of the claims, which are to be interpreted in light of the specification as a whole.

Applications

It will be understood that the system described herein may be used in various ways, such as those purposes described in the prior art, and also may be used in other ways to take advantage of the aspects described above. A non-exhaustive list of applications are discussed below.

The system may be used for imaging angiogenesis for different pre-clinical tumor models.

The system may be used for unmixing targets based on their absorption, scattering or frequency contents by taking advantage of different wavelengths, different pulse widths, different coherence lengths, repetition rates, exposure time, etc.

The system may be used to image with resolution up to and exceeding the diffraction limit.

The system may be used to image anything that absorbs light, including exogenous and endogenous targets and biomarkers.

The system may have some surgical applications, such as functional and structural imaging during brain surgery, use for assessment of internal bleeding and cauterization verification, imaging perfusion sufficiency of organs and organ transplants, imaging angiogenesis around islet transplants, imaging of skin-grafts, imaging of tissue scaffolds and biomaterials to evaluate vascularization and immune rejection, imaging to aid microsurgery, guidance to avoid cutting critical blood vessels and nerves.

The system may also have some gastroenterological applications, such as imaging vascular beds and depth of invasion in Barrett's esophagus and colorectal cancers. Depth of invasion, in at least some embodiments, is key to prognosis and metabolic potential. This may be used for virtual biopsy, crohn's diseases, monitoring of IBS, inspection of carotid artery. Gastroenterological applications may be combined or piggy-backed off of a clinical endoscope and the miniaturized PARS system may be designed either as a standalone endoscope or fit within the accessory channel of a clinical endoscope.

The system may also be used for clinical imaging of micro- and macro-circulation and pigmented cells, which may find use for applications such as in (1) the eye, potentially augmenting or replacing fluorescein angiography; (2) imaging dermatological lesions including melanoma, basal cell carcinoma, hemangioma, psoriasis, eczema, dermatitis, imaging Mohs surgery, imaging to verify tumor margin resections; (3) peripheral vascular disease; (4) diabetic and pressure ulcers; (5) burn imaging; (6) plastic surgery and microsurgery; (7) imaging of circulating tumor cells, especially melanoma cells; (8) imaging lymph node angiogenesis; (9) imaging response to photodynamic therapies including those with vascular ablative mechanisms; (10) imaging response to chemotherapeutics including antiangiogenic drugs; (11) imaging response to radiotherapy.

The system may also be used for some histopathology imaging applications, such as frozen pathology, creating H&E-like images from tissue samples, virtual biopsy, etc. It may be used on various issues corporations such as formalin-fixed paraffin-embedded tissue blocks, formalin-fixed paraffin-embedded tissue slides, frozen pathology sections, freshly resected specimen, etc. Within these samples visualization of macromolecules such as DNA, RNA, cytochromes, lipids, proteins, etc. may be performed.

The system may be useful in estimating oxygen saturation using multi-wavelength PARS excitation in applications including: (1) estimating venous oxygen saturation where pulse oximetry cannot be used including estimating cerebrovenous oxygen saturation and central venous oxygen saturation. This could potentially replace catheterization procedures which can be risky, especially in small children and infants.

Oxygen flux and oxygen consumption may also be estimated by using PARS imaging to estimate oxygen saturation, and to estimate blood flow in vessels flowing into and out of a region of tissue.

The system may be useful in separating salient histological chromophores such as cell nuclei and the surrounding cytoplasm by leveraging their respective absorption spectra.

The systems may be used for unmixing targets using their absorption contents, scattering, phase, polarization or frequency contents by taking advantage of different wavelengths, different pulse widths, different coherence lengths, repetition rates, fluence, exposure time, etc.

Other examples of applications may include imaging of contrast agents in clinical or pre-clinical applications; identification of sentinel lymph nodes; non-or minimally-invasive identification of tumors in lymph nodes; imaging of genetically-encoded reporters such as tyrosinase, chromoproteins, fluorescent proteins for pre-clinical or clinical molecular imaging applications; imaging actively or passively targeted optically absorbing nanoparticles for molecular imaging; and imaging of blood clots and potentially staging the age of the clots.

Other examples of applications may include clinical and pre-clinical ophthalmic applications; oxygen saturation measurement and retinal metabolic rate in diseases such as age related macular degeneration, diabetic retinopathy and glaucoma, limbal vasculature and stem cells imaging, corneal nerve and neovascularization imaging, evaluating Schlemm canal changes in glaucoma patients, choroidal neovascularization imaging, anterior and posterior segments blood flow imaging and blood flow state.

The system may be used for measurement and estimation of metabolism within a biological sample leveraging the capabilities of both PARS and OCT. In this example the OCT may be used to estimate volumetric blood flow within a region of interest, and the PARS systems may be used to measure oxygen saturation within blood vessels of interest. The combination of these measurements then provide estimation of metabolism within the region.

The system may be used for head and neck cancer types and skin cancer types, functional brain activities, Inspecting stroke patient's vasculature to help locate clots, monitoring changes in neuronal and brain function/development as a result of changing gut bacteria composition, atherosclerotic plaques, monitoring oxygen sufficiency following flap reconstruction, profusion sufficiency following plastic or cosmetic surgery and imaging the cosmetic injectables.

The system may be used for topology tracking of surface deformations. For example, the OCT may be used to track the location of the sample surface. Then corrections may be applied to a tightly focused PARS device using mechanisms such as adaptive optics to maintain alignment to that surface as scanning proceeds.

The system may be implemented in various different form factors appropriate to these applications such as a tabletop microscope, inverted microscope, handheld microscope, surgical microscope, ophthalmic microscope, endoscope, etc.

Embodiments

A photoacoustic remote sensing and optical coherence tomography system for functional, structural, and multiplex visualization of subsurface structures in a sample, comprising:

One or more optical sources configured to generate pressure and thermal signals in the sample at an excitation location;

One or more optical sources configured to generate an interrogation beam or collection of interrogation beams incident on the sample at the excitation location, a portion of the interrogation beam or collection of interrogation beams returning from the sample that are indicative of the generated pressure and thermal signals;

One or more optical sources configured to generate an interrogation beam or collection of interrogation beams incident on the sample at the excitation location, a portion of the interrogation beam or collection of interrogation beams returning from the sample that are indicative of the optical scattering;

A detector or collection of detectors configured to detect the returning portion of the interrogation beam or collection of interrogation beams;

An optical system configured to focus the beams into the sample;

A processor configured to calculate an image of the sample based on the detected portions of the returning portions of the interrogation beams from the sample.

The system including a non-linear optical element configured to generate or modify beam characteristics.

The system wherein one or more of the PARS excitation/interrogation and OCT interrogation use the same optical source.

The system with different embodiments such as tabletop, handheld, surgical microscope, ophthalmic microscope, endoscope.

The system wherein optical sources may be any continuous, pulsed or modulated source of electromagnetic radiation with wavelengths ranging from approximately 50 nm to 100 μm.

The system including a non-linear optical element configured to generate or modify beam characteristics.

The system wherein one or more of the PARS excitation/interrogation/signal enhancement beams use the same optical source.

The system with different embodiments such as tabletop, handheld, surgical microscope, ophthalmic microscope, endoscope.

For some applications the imaging head may not include any focusing elements.

The system wherein the first, second, and third focal points are at a depth below the surface of the sample that is from 50 nm to 10 mm.

The system wherein all of the beams are focused into the sample and collected from the sample using the same focusing optics.

The system wherein beams are focused into the sample and beams collected from the sample use different focusing optics.

The system wherein focusing optics are normal to the surface.

The system wherein the central axis of the focusing optics form an angle with the surface normal that is between 0 degrees and 85 degrees.

The system wherein the beam combiner is implemented using free-space optics.

The system wherein the beam complainers implemented using fiber-based devices.

The system wherein the imaging head provides optical scanning by galvanometer mirrors, MEMS mirrors, polygon scanners, stepper/DC motors, etc.

The system wherein a mechanical scanner such as stepper stages, DC motor stages, linear drive stages, piezo drive stages, piezo stages, etc. is used to scan the sample about the imaging head, the imaging head about the sample, or to scan both at the same time.

The system wherein the detector is an interferometer.

The system wherein the detector is a non-interferometric detector

The system wherein the portion of the beams returning from the sample encode generated pressure and thermal signals as [intensity, polarization, frequency, phase, fluorescence, non-linear scattering, non-linear absorption] variations.

The system wherein the portion of the beams returning from the sample are amplified by an optical amplifier.

The system wherein adaptive optics elements are used to adjust beam properties such as aberrations, focus, and to compensate for surface roughness.

The system wherein the system is configured to generate the structure of the sample through [a glass window, air, water, vacuum, other material]

The system wherein the OCT detection is configured to detect the PARS modulations within the sample. OCT detection in this case may act as a short-coherence PARS interferometric detection. This may facilitate the omission of the PARS detection all together or allow for depth-sensitive optical absorption recovery from within a sample. This system will detect PARS initial pressure signals at the origin to provide unique information about the optical absorption of the sample.

The system wherein the OCT detection is configured to detect the vibration and oscillations generated by PARS signals. This system will detect the vibrations caused by PARS pressure propagation at the surface and subsurface of the samples to provide unique information about the optical absorption of the sample.

The system wherein the OCT detection is configured to detect the topology of the sample.

The system wherein the OCT detection is configured to detect the surface roughness of the sample.

A dual-modality photoacoustic remote sensing combined with optical coherence tomography (PARS-OCT) system for visualizing details in a sample, the system comprising: one or more light sources configured to generate (1) one or more excitation beams configured to generate signals in the sample at one or more first locations below a surface of the sample; (2) one or more interrogation beams incident on the sample at one or more second locations; (3) a sample beam; and (4) a reference beam; wherein a portion of the one or more interrogation beams returning from the sample is indicative of the generated signals; one or more first optical detectors configured to detect a returning portion or portions of the one or more interrogation beams; one or more interferometers, each with a sample arm and a reference arm, wherein the sample arm is configured to direct the sample beam from the one or more light sources to a third location and the reference arm is configured to direct the reference beam from the one or more light sources into a path; wherein a portion of the sample beam returning from the sample arm is indicative of scattering collected by the sample arm; wherein a portion of the reference beam returning from the reference arm is indicative of scattering collected by the reference arm; and wherein the interferometer is configured to detect returning portions from the one or more sample arms and one or more reference arms.

The PARS-OCT system, wherein the signals generated by the one or more excitation beams include ultrasonic signals, thermal signals, photoacoustic signals, and/or pressure signals, and the returning portion or portions of the one or more interrogation beams are indicative of the generated ultrasonic signals, thermal signals, photoacoustic signals, and/or pressure signals.

The PARS-OCT system, further including one or more beam combiners configured to combine at least one excitation beam, at least one interrogation beam, and/or the sample beam before delivery to the sample.

The PARS-OCT system, wherein the one or more beam combiners are configured to direct a returning portion of the at least one interrogation beam to the one or more first optical detectors, and also is configured to direct a returning portion of the sample beam to the interferometer.

The PARS-OCT system, further including a bright field microscopy light source, wherein the one or more beam combiners are configured to combine light from the bright field microscopy light source with the at least one excitation beam, at least one interrogation beam, and the sample beam before delivery to the sample.

The PARS-OCT system, wherein the system is configured to provide absorption and scattering contrast of the sample.

The PARS-OCT system, further including a scope, wherein the scope includes a collimator and imaging optics, wherein the one or more excitation beams, the one or more interrogation beams, and/or the sample beam are passed through the scope before delivery to the sample.

The PARS-OCT system, wherein the one or more light sources includes a first light source configured to generate the one or more excitation beams, the sample beam, and the reference beam.

The PARS-OCT system, wherein the one or more light sources includes a second light source configured to generate the one or more interrogation beams.

The PARS-OCT system, wherein the one or more light sources includes a first light source configured to generate the one or more interrogation beams, the sample beam, and the reference beam.

The PARS-OCT system, further including one or more optical systems configured to focus or direct (1) the one or more excitation beams to one or more first focal points, and (2) the one or more interrogation beams at one or more second focal points, the one or more first and second focal points being below the surface of the sample.

The PARS-OCT system, wherein: the one or more light sources are configured to generate one or more signal enhancement beams, incident on the sample at the one or more first locations; the one or more first optical detectors are configured to detect a returning portion of the one or more signal enhancement beams; and the returning portion of the one or more signal enhancement beams returning from the sample is indicative of generated PARS signals.

The PARS-OCT system, wherein the one or more excitation beams include exactly one wavelength, and the one or more signal enhancement beams include a plurality of wavelengths.

The PARS-OCT system, further including a controller configured to determine a temperature of the sample based on an intensity of a feedback from the one or more optical detectors.

The PARS-OCT system, further including a processing unit configured to provide an image with a resolution greater than an optical diffraction limit by leveraging nonlinear optical absorption contrast effects within the sample, wherein the effects include optical intensity-induced optical absorption attenuation or photobleaching, and nonlinear thermal dependencies of material properties including the thermal expansion coefficient, wherein the processing unit is configured use as inputs several scans of a sample such that non-linear PARS signal generation occurs across acquisitions allowing for the application of a Vandermonde matrix-based process for separating N'th order power relationships.

The PARS-OCT system, further including one or more optical systems configured to disperse the one or more interrogation beams based on wavelength or spatial positioning of the one or more interrogation beams; wherein the one or more optical systems are configured to recombine the one or more interrogation beams based on the wavelength or spatial positioning of the one or more interrogation beams.

The PARS-OCT system, further including one or more pinholes or apertures configured to map desired light to the one or more first optical detectors when optically or mechanically scanning the beams, or when mechanically scanning the sample or an image head.

The PARS-OCT system, wherein the interferometer is configured to detect PARS modulations within the sample, or vibration and oscillations generated by the one or more excitation beams such that the OCT may in turn provide optical absorption contrast.

A dual-modality photoacoustic remote sensing combined with optical coherence tomography (PARS-OCT) system for visualizing details in a sample, the system providing absorption and scattering contrast of tissue, the system comprising: a PARS subsystem including: one or more light sources configured to generate (1) one or more excitation beams configured to generate ultrasonic signals, thermal signals, photoacoustic signals, and/or pressure signals in the sample at one or more excitation locations; (2) one or more interrogation beams incident on the sample at one or more interrogation locations; one or more optical systems configured to focus or direct the one or more excitation beams at the one or more first focal points, and the one or more interrogation beams at one or more second focal points, the one or more first and second focal points being below the surface of the sample; a portion of one or more interrogation beams returning from the sample that is indicative of the generated ultrasonic signals, thermal signals, photoacoustic signals, and/or pressure signals; and one or more optical detectors configured to detect the returning portion or portions of the one or more interrogation beams; and an OCT subsystem including: one or more light sources; and one or more interferometers, each with a sample arm and a reference arm, where the sample arm directs a sample portion of the one or more light sources to a third focal point, and the reference arm directs a reference portion of the one or more light sources into a path of known length; a portion of light returning from the sample arm is indicative of the scattering collected by the sample arm; a portion of the light returning from the reference arm is indicative of the scattering collected by the reference arm; wherein the one or more interferometers are configured to detect returning portions from the sample arm and the reference arm wherein (1) the PARS subsystem and the OCT subsystem share at least one light source, or (2) the PARS subsystem and the OCT subsystem have only separate light sources.

The following applications: imaging histological samples; imaging cell nuclei; imaging proteins; imaging DNA; imaging RNA; imaging lipids; imaging of blood oxygen saturation; imaging of tumor hypoxia; imaging of wound healing, burn diagnostics, or surgery; imaging of microcirculation; blood oxygenation parameter imaging; estimating blood flow in vessels flowing into and out of a region of tissue; imaging of molecularly-specific targets; imaging angiogenesis for pre-clinical tumor models; clinical imaging of micro- and macro-circulation and pigmented cells; imaging of the eye; augmenting or replacing fluorescein angiography; imaging dermatological lesions; imaging melanoma; imaging basal cell carcinoma; imaging hemangioma; imaging psoriasis; imaging eczema; imaging dermatitis; imaging Mohs surgery; imaging to verify tumor margin resections; imaging peripheral vascular disease; imaging diabetic and/or pressure ulcers; burn imaging; plastic surgery; microsurgery; imaging of circulating tumor cells; imaging melanoma cells; imaging lymph node angiogenesis; imaging response to photodynamic therapies; imaging response to photodynamic therapies having vascular ablative mechanisms; imaging response to chemotherapeutics; imaging frozen pathology samples; imaging paraffin embedded tissues; imaging H&E-like images; imaging oxygen metabolic changes; imaging response to anti-angiogenic drugs; imaging response to radiotherapy; estimating oxygen saturation using multi-wavelength PARS excitation; estimating venous oxygen saturation where pulse oximetry cannot be used; estimating cerebrovenous oxygen saturation and/or central venous oxygen saturation; estimating oxygen flux and/or oxygen consumption; imaging vascular beds and depth of invasion in Barrett's esophagus and/or colorectal cancers; functional and structural imaging during brain surgery; assessment of internal bleeding and/or cauterization verification; imaging perfusion sufficiency of organs and/or organ transplants; imaging angiogenesis around islet transplants; imaging of skin-grafts; imaging of tissue scaffolds and/or biomaterials to evaluate vascularization and/or immune rejection; imaging to aid microsurgery; guidance to avoid cutting blood vessels and/or nerves; imaging of contrast agents in clinical or pre-clinical applications; identification of sentinel lymph nodes; non-or minimally-invasive identification of tumors in lymph nodes; imaging of genetically-encoded reporters, wherein the genetically-encoded reporters include tyrosinase, chromoproteins, and/or fluorescent proteins for pre-clinical or clinical molecular imaging applications; imaging actively or passively targeted optically absorbing nanoparticles for molecular imaging; imaging of blood clots; staging an age of blood clots; remote or non-invasive intratumoural assessment of glucose concentration by detection of endogenous glucose absorption peeks; assessment of organoid growth; monitoring of developing embryos; assessment of biofilm composition; assessment of tooth decay; assessment of non-living structures; evaluating the composition of paintings for non-invasive confirmation of authenticity; evaluation of archeological artifacts; manufacturing quality control; manufacturing quality assurance; replacing a catheterization procedure; gastroenterological applications; single-excitation pulse imaging over an entire field of view; imaging of tissue; imaging of cells; imaging of scattered light from object surfaces; imaging of absorption-induced changes of scattered light; or non-contact imaging of optical absorption.

The invention claimed is:

1. A dual-modality photoacoustic remote sensing combined with optical coherence tomography (PARS-OCT) system for visualizing details in a sample, the system comprising:
   one or more light sources configured to generate (1) one or more excitation beams configured to generate signals in the sample at one or more first locations below a surface of the sample; (2) one or more interrogation beams incident on the sample at one or more second locations; (3) a sample beam; and (4) a reference beam;
   a second light source, separate from the one or more light sources, the second light source configured to generate one or more signal enhancement beams incident on the sample at the one or more first locations, wherein the one or more signal enhancement beams are configured to raise a temperature of the sample within a focal point of the one or more interrogation beams, and wherein any of the one or more signal enhancement beams have a lower intensity than each of the one or more excitation beams;
   wherein a portion or portions of the one or more interrogation beams returning from the sample is indicative of the generated signals;
   one or more first optical detectors configured to detect the portion or portions of the one or more interrogation beams returning from the sample;
   one or more interferometers, each with a sample arm and a reference arm, wherein the sample arm is configured to direct the sample beam from the one or more light sources to a third location and the reference arm is configured to direct the reference beam from the one or more light sources into a path;
   wherein a portion of the sample beam returning from the sample arm is indicative of signal collected by the sample arm;
   wherein a portion of the reference beam returning from the reference arm is indicative of signal collected by the reference arm; and
   wherein the one or more detector are configured to detect the portion of the sample beam returning from the sample arm and the portion of the reference beam returning from the reference arm, wherein the system further includes a processor configured to calculate an image of the sample based on the portion or portions of the one or more interrogation beams returning from the sample, wherein an intensity modulation of the portion or portions of the one or more interrogation beams returning from the sample is increased by the one or more signal enhancement beams, due to the raised temperature of the sample within the focal point of the one or more interrogation beams, which modifies a local refractive index of the sample, compared to an intensity modulation of the portion or portions of the one or more interrogation beams returning from the sample that would have been generated without the one or more signal enhancement beams;
   wherein the signals generated by the one or more excitation beams include ultrasonic signals, thermal signals, photoacoustic signals, fluorescence signals, and/or pressure signals, and the returning portion or portions of the one or more interrogation beams are indicative of the generated ultrasonic signals, thermal signals, photoacoustic signals, and/or pressure signals.

2. The system of claim 1, further including one or more beam combiners configured to combine at least one excitation beam, at least one interrogation beam, and/or the sample beam before delivery to the sample, wherein the scattering and emission due to the excitation beam will be collected independent of interrogation beam.

3. The system of claim 2, wherein the one or more beam combiners are configured to direct the portion or portions of the one or more interrogation beams returning from the sample to the one or more first optical detectors, and also is configured to direct the portion of the sample beam returning from the sample arm to the one or more interferometers.

4. The system of claim 2, further including a bright field microscopy light source, wherein the one or more beam combiners are configured to combine light from the bright field microscopy light source with the at least one excitation beam, at least one interrogation beam, and the sample beam before delivery to the sample.

5. The system of claim 1, wherein the system is configured to provide absorption and scattering contrast of the sample.

6. The system of claim 1, further including an endoscope, wherein the endoscope includes a collimator and imaging optics, wherein the one or more excitation beams, the one or more interrogation beams, and/or the sample beam are passed through the endoscope before delivery to the sample.

7. The system of claim 1, wherein the one or more light sources includes a first light source configured to generate the one or more excitation beams, the sample beam, and the reference beam, wherein the one or more light sources includes a second light source configured to generate the one or more interrogation beams.

8. The system of claim 1, wherein the one or more light sources includes a first light source configured to generate the one or more interrogation beams, the sample beam, and the reference beam.

9. The system of claim 1, wherein the one or more first locations include one or more first focal points, and the one or more second locations include one or more second focal points, and the system further including one or more optical systems configured to focus or direct (1) the one or more excitation beams to one or more first focal points, and (2) the one or more interrogation beams at one or more second focal points, the one or more first and second focal points being below the surface of the sample.

10. The system of claim 1, wherein the one or more excitation beams include a plurality of wavelengths, and the one or more signal enhancement beams include exactly one wavelength.

11. The system of claim 1, further including a controller configured to determine a temperature of the sample based on an intensity of a feedback from the one or more optical detectors.

12. The system of claim 1, further including:
one or more optical systems configured to disperse the one or more interrogation beams based on wavelength or spatial positioning of the one or more interrogation beams;
wherein the one or more optical systems are configured to recombine the one or more interrogation beams based on the wavelength or spatial positioning of the one or more interrogation beams.

13. The system of claim 1, further including one or more pinholes or apertures configured to map desired light to the one or more first optical detectors when optically or mechanically scanning the beams, or when mechanically scanning the sample or an image head.

14. The system of claim 1, wherein the one or more interferometers are configured to detect PARS modulations within the sample, or vibration and oscillations generated by the one or more excitation beams such that the OCT may in turn provide optical absorption contrast.

15. The system of claim 1, wherein the one or more signal enhancement beams is configured to raise a temperature of the sample by up to 30 Kelvin.

16. A dual-modality photoacoustic remote sensing combined with optical coherence tomography (PARS-OCT) system for visualizing details in a sample, the system comprising:
one or more light sources configured to generate (1) one or more excitation beams configured to generate signals in the sample at one or more first locations below a surface of the sample; (2) one or more interrogation beams incident on the sample at one or more second locations; (3) a sample beam; (4) a reference beam;
wherein a portion or portions of the one or more interrogation beams returning from the sample is indicative of the generated signals;
one or more first optical detectors configured to detect the portion or portions of the one or more interrogation beams returning from the sample;
one or more interferometers, each with a sample arm and a reference arm, wherein the sample arm is configured to direct the sample beam from the one or more light sources to a third location and the reference arm is configured to direct the reference beam from the one or more light sources into a path;
wherein a portion of the sample beam returning from the sample arm is indicative of scattering collected by the sample arm;
wherein a portion of the reference beam returning from the reference arm is indicative of scattering collected by the reference arm; and
wherein the one or more interferometers are configured to detect the portion of the sample beam returning from the sample arm and the portion of the reference beam returning from the reference arm,
further including a processing unit configured to provide an image with a resolution greater than an optical diffraction limit by leveraging nonlinear optical absorption contrast effects within the sample, wherein the effects include optical intensity-induced optical absorption attenuation or photobleaching, and nonlinear thermal dependencies of material properties including the thermal expansion coefficient, wherein the processing unit is configured to use as inputs several scans of the sample such that non-linear PARS signal generation occurs across acquisitions allowing for the application of a Vandermonde matrix-based process for separating N'th order power relationships.

17. A dual-modality photoacoustic remote sensing combined with optical coherence tomography (PARS-OCT) system for visualizing details in a sample, the system providing absorption and scattering contrast of tissue, the system comprising:
a PARS subsystem including:
one or more light sources configured to generate (1) one or more excitation beams configured to generate ultrasonic signals, fluorescence signals, thermal signals, photoacoustic signals, and/or pressure signals in at least a first target within the sample at one or more excitation locations; (2) one or more interrogation beams incident on the sample at one or more interrogation locations, the one or more interrogation beams having a different wavelength than the one or more excitation beams, wherein the wavelength of the one or more interrogation beams is configured to suppress any ultrasonic signals, thermal signals, fluorescence signals, photoacoustic signals, and/or pressure signals that would be generated by a second target within the sample due to the one or more excitation beams being applied to the sample, by populating absorption energy levels of the second target, wherein the first target and the second target have different chromophores; and one or more optical systems configured to focus or direct the one or more excitation beams at one or more first focal points, and the one or more interrogation beams at one or more second focal points, the one or more first and second focal points being below a surface of the sample; wherein a portion of one or more interrogation beams returning from the sample that is indicative of the generated ultrasonic signals, thermal signals, photoacoustic signals, fluorescence signals, and/or pressure signals; and wherein a portion of one or more excitation beams returning from the sample is indicative of the generated ultrasonic signals, thermal signals, photoacoustic signals, fluorescence signals, and/or pressure signals; and one or more optical detectors configured to detect the returning portion or portions of the one or more interrogation or excitation beams; and an OCT subsystem including:
one or more light sources; and
one or more interferometers, each with a sample arm and a reference arm, where the sample arm directs a sample portion of the one or more light sources to a third focal point, and the reference arm directs a reference portion of the one or more light sources into a path of known length; wherein 1) a portion of light returning from the sample arm is indicative of scattering collected by the sample arm; and 2) a portion of the light returning from the reference arm is indicative of scattering collected by the reference arm;

wherein the one or more interferometers are configured to detect returning portions from the sample arm and the reference arm; and wherein (1) the PARS subsystem and the OCT subsystem share at least one light source, or (2) the PARS subsystem and the OCT subsystem have only separate light sources; and a processor configured to:
unmix the first target and the second target within the sample from one another and assign the first target and the second target a different color based on optical properties of the first target and optical properties of the second target, and
cause the different colors to be shown simultaneously on a single image, wherein the first target and the second target each include endogenous and/or exogenous chromophores, wherein the processor is configured to unmix the first target and the second target after scanning the sample with the one or more light sources.

18. The system of claim 17, wherein the processor is configured to unmix a size and a shape of the first target and the second target within the sample based on absorption, temperature, and/or scattering of the first target and the second target, and additionally based on one or more of polarization, frequency, phase, and/or fluorescence of the first target and the second target.

19. The system of claim 18, further including a separate light source configured to generate one or more signal enhancement beams incident on the sample at the one or more first locations, wherein the one or more excitation beams, the one or more interrogation beams, and the one or more signal enhancement beams are co-focused, wherein the processor is further configured to:

calculate the image of the sample based on the portion or portions of the one or more interrogation beams returning from the sample, wherein an intensity modulation of the portion or portions of the one or more interrogation beams returning from the sample is increased by the one or more signal enhancement beams compared to an intensity modulation of the portion or portions of the one or more interrogation beams returning from the sample that would have been generated without the one or more signal enhancement beams.

20. The system of claim 17, wherein the first target includes hemoglobin, cytoplasm, nucleic material, or lipids, and the second target includes a different selection of hemoglobin, cytoplasm, nucleic material, or lipids.

* * * * *

UNITED STATES PATENT AND TRADEMARK OFFICE
CERTIFICATE OF CORRECTION

PATENT NO. : 11,122,978 B1  
APPLICATION NO. : 17/010500  
DATED : September 21, 2021  
INVENTOR(S) : Parsin Haji Reza et al.

Page 1 of 1

It is certified that error appears in the above-identified patent and that said Letters Patent is hereby corrected as shown below:

On the Title Page

Item (72) (Inventors), delete "Reza, Edmonton" and insert --Reza, Waterloo--

Item (72) (Inventors), delete "Hosseinaee, Edmonton" and insert --Hosseinaee, Waterloo--

Item (72) (Inventors), delete "Bell, Edmonton" and insert --Bell, Waterloo--

Item (72) (Inventors), delete "Abbasi, Edmonton" and insert --Abbasi, Waterloo--

Item (72) (Inventors), delete "Eccelstone, Edmonton" and insert --Eccelstone, Waterloo--

Item (73) Line 1 (Residence of Assignee), delete "Inc." and insert --Inc., 22 King Street South, Suite 300, Waterloo, ON N2J 1N8--

Signed and Sealed this  
Twenty-eighth Day of December, 2021

Drew Hirshfeld  
*Performing the Functions and Duties of the*  
*Under Secretary of Commerce for Intellectual Property and*  
*Director of the United States Patent and Trademark Office*